United States Patent [19]
Vakharia et al.

[11] Patent Number: 6,017,759
[45] Date of Patent: Jan. 25, 2000

[54] CHIMERIC INFECTIOUS BURSAL DISEASE VIRUS CDNA CLONES, EXPRESSION PRODUCTS AND VACCINES BASED THEREON

[75] Inventors: Vikram Vakharia; David B. Snyder, both of Bowie; Stephanie A. Mengel-Whersat, Hyattsville, all of Md.

[73] Assignee: University of Maryland College Park, College Park, Md.

[21] Appl. No.: 09/031,655

[22] Filed: Feb. 27, 1998

Related U.S. Application Data

[62] Division of application No. 08/219,262, Mar. 29, 1994, Pat. No. 5,788,970.

[51] Int. Cl.[7] .......... A61K 39/295; C12N 15/40; C07K 14/08
[52] U.S. Cl. .......... 435/325; 435/69.1; 435/91.4; 435/235.1; 435/320.1; 424/186.1; 424/199.1; 424/202.1; 424/204.1; 424/192.1; 514/44; 530/300; 530/350; 530/389.4; 536/23.1; 536/23.72
[58] Field of Search .......... 424/186.1, 199.1, 424/202.1, 204.1, 192.1; 435/69.1, 91.4, 235.1, 320.1, 325; 514/44; 530/300, 350, 389.4; 536/23.1, 23.72

[56] References Cited

FOREIGN PATENT DOCUMENTS

WO91/16925  11/1991  WIPO .

OTHER PUBLICATIONS

Journal of General Virology, vol. 70, pp. 1473–1481, 1989, K.J. Fahey, et al., "A Conformation Immunogen on VP–2 of Infectious Bursal Disease Virus That Induces Virus–Neutralizing Antibodies That Passively Protect Chickens".
Archives of Virology, vol. 120, pp. 193–205, 1991, C.D. Bayless, et al., "A Recombinant Fowlpox Virus That Expresses The VP2 Antigen of Infectious Disease Virus Induces Protection Against Mortality Caused By The Virus".
Journal of General Virology, vol. 74, pp. 1201–1206, 1993, V.N. Vakharia, et al., "Infectious Bursal Disease Virus Structural Proteins Expressed in a Baculovirus Recombinant Confer Protection in Chickens".

*Primary Examiner*—Jeffrey Stucker
*Assistant Examiner*—Phuong T Bui
*Attorney, Agent, or Firm*—Oblon, Spivak, McClelland, Maier & Neustadt, P.C.

[57] ABSTRACT

Chimeric cDNA for the expression of immunogenic polypeptides include the genetic epitopic determinants for a base infectious bursal disease virus strain and at least one other infectious bursal disease virus strain. The genetic epitopic determinants encode amino acids or amino acid sequences which define epitopes bound to by previously established monoclonal antibodies. The immunogens expressed by the cDNA may be employed to provide a vaccine against a plurality of IBDV strains. The epitopic determinant of IBDV lethal strains has been detected, and an immunogen for conferring immunity with respect thereto is disclosed. Similarly, a monoclonal antibody specific for IBDV lethal strains is identified, and a vaccine for passive immunization therewith is also disclosed. Immunogens exhibiting conformational epitopes, in the form of virus-like particles, are effective in the preparation of vaccines.

9 Claims, 38 Drawing Sheets

Fig. 3B

```
              10         20         30         40         50         60
              |          |          |          |          |          |
GLS    NGTINAVTFQ GSLSELTDVS YNGLMSATAN INDKIGNVLV GEGVTVLSLP TSYDLGYVRL
DS326  ---------- ---------- ---------- ---------- ---------- ----------
E/Del  ---------- ---------- ---------- ---------- ---------- ----------
D78    ---------- ---------- ---------- ---------- ---------- ----------
Cu-1   ---------- ---------- ---------- ---------- ---------- ----------
PBG98  ---------- ---------- ---------- ---------- ---------- ----------
52/70  ---------- ---------- ---------- ---------- ---------- ----------
STC    ---------- ---------- ---------- ---------- ---------- ----------
002-73 ---------- ---------- ---------- ---------- ---------- ----------
OH     ---------- -------Y-- ---------- ---------- ---------- --S-------

70         80         90        100        110
              |          |          |          |          |
       GDPIPAIGLD PKMVATCDSS DRPRVYTITA ADDYQFSSQY QTGGVTITLF SANIDAITSL - 240
       ---------- ---------- ---------- ---------- ----S----- ----------
       ---------- ---------- ---------- ---N------ ---------- ----------
       ---------- ---------- ---------- ---------- ---P------ ----------
       ---------- ---------- ---------- ---------- ---P------ ----------
       ---------- ---------- ---------- ---------- ---P------ ----------
       ---------- ---------- ---------- ---------- ---P------ ----------
       ---------- ---------- ---------- ---------- ---P------ ----------
       ---------- ---------- ----V----- ---E------ ---P------ -------N--
       ---A------ --LM------ ---------- ---------- -L IPS-KT- T----L----
```

FIG. 3C

```
              10         20         30         40         50         60
              |          |          |          |          |          |
GLS      SVGGELVF KTSVHSLVLGAT IYLIGFDGSA VITRAVAANN GLTTGTDNLM PFNLVIPTNE
DS326    -------- ---Q-------- -------T-- ---------- ----A----- ----------
E/Del    -------- ---Q-------- -------T-- ---------- --A-I----- ----------
D78      -------- -------G---- ------TT-- ---------- ---------- ----------
Cu-1     -------- Q------G---- ------TT-- -------T-- ---------- ----------
PBG98    --I----- R------G---- ------TT-- ---------- ---------- ----------
52/70    -------- Q------G---- ------TA-- ----D----- ---A------ ----------
STC      -------- Q---QG------ ------TT-- ----D----- ---A------ ----------
002-73   -------- Q---QG--N--- --V---TT-- ----G----- ---A------ -------S--
OH       ------I- SQVTI-SIEVDV ---F----TE -TVK---TDF ----N---V- ----GG--S-

70         80         90         100        110
              |          |          |          |          |
ITQPITSIKL EIVTSKSGGQ EGDQMSWSAS GSLAVTIHGG NYPGALRPVT LVAYERVATG - 360
---K------ ---L------ --A-E----- ---------- ---------- ---------- 
----I----- ------D--- -A-------R ---------- ---------- ---------- 
---------- ---------- -A-------K ---------- ---------- ---------- 
---------- ---------- -A----L--R ---------- ---------- ---------- 
---------- ---------- -A-------- ---------- ---------- ---------- 
-----V---- ---------- -A-------- ---------- ---------- ---------- 
---------- ---------- -A----L--N ---------- ---------- ---------- 
---------- ---------- -A--PI--TV -T------V- ---------- ----A----- - 361
----M----- --V--Y-R-T A-------TV ---------- ---------- ----A-----
```

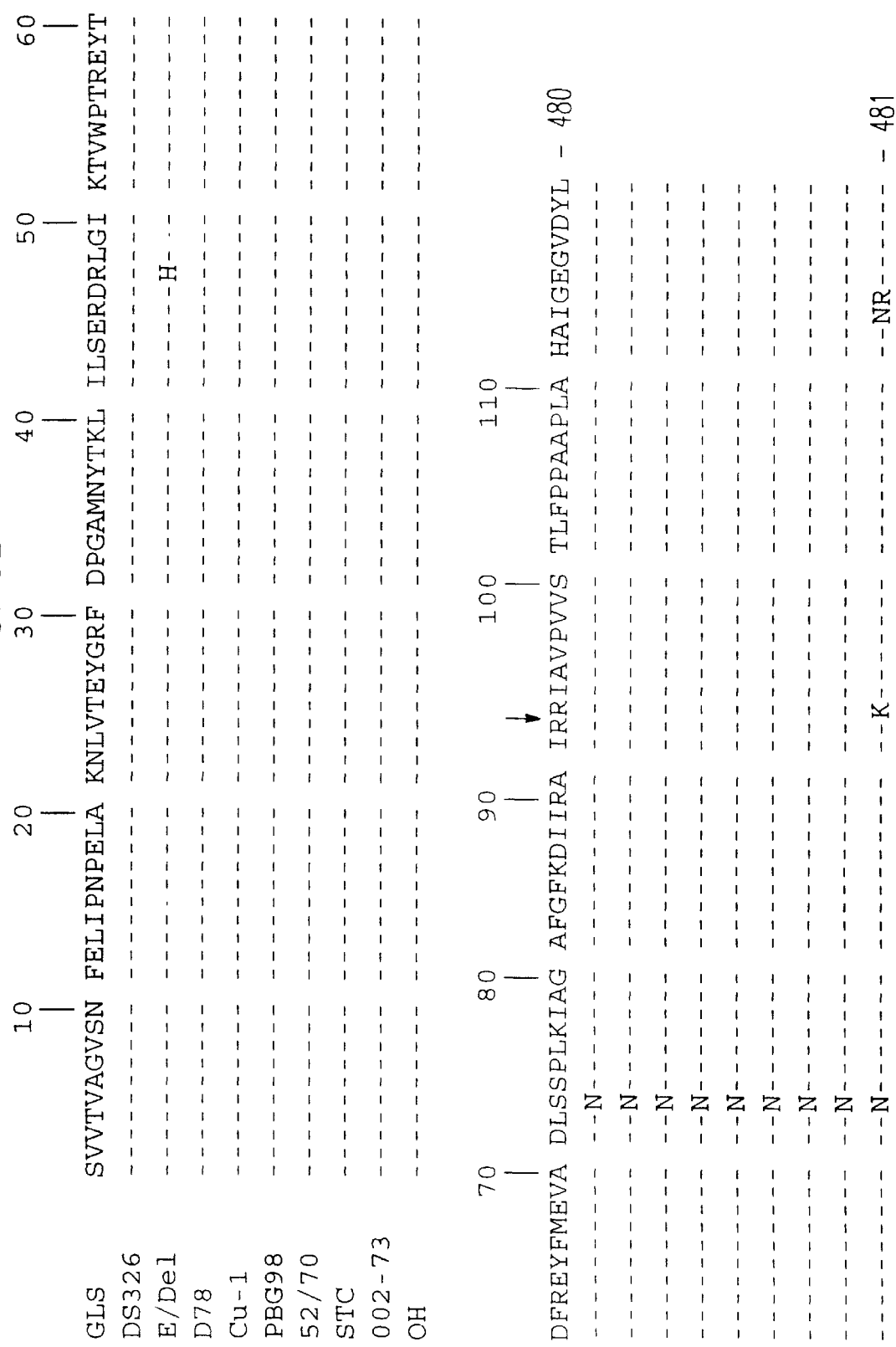

```
            10         20         30         40         50         60
            |          |          |          |          |          |
         LGDEAQAASG TARAASGKAR AASGRIRQLT LAADKGYEVV ANLFQVPQNP VVDGILASPG
GLS      ---------- ---------- ---------- ---------- ---------- ----------
DS326    ---------- ---------- ---------- ---------- ---------- ----------
E/Del    ---------- ---------- ---------- ---------- ---------- ----------
D78      ---------- ---------- ---------- ---------- ---------- ----------
Cu-1     ---------- ---------- ---------- ---------- ---------- ----------
PBG98    ---------- ---------- ---------- ---------- ---------- ----------
52/70    ---------- ---------- ---------- ---------- ---------- ----------
STC      ---------- ---------- ---------- ---------- ---------- ----------
002-73   ---------- --------G- ---------- ---------- ------M--- ----------
OH       ---------- ---------- ---------- ---------- ---------- -------I--

70         80         90         100        110
            |          |          |          |          |
         ILRGAHNLDC VLREGATLFP VVITTVEDAM TPKALNSKMF AVIEGVREDL QPPSQRGSFI - 600
         ---------- ---------- ---------- ---------- ---------- ----------
         ---------- ---------- ---------- ---------- ---------- ----------
         ---V------ ---------- ---------- ---------- ----A----- ----------
         ---V------ ---------- ---------- ---------- ---------- ----------
         ---V------ ---------- ---------- ---------- ---------- ----------
         ---V------ ---------- ---------- --------I- ---------- ----------
         ---V------ ---------- ---------- ---------- ---------- ----------
         ---V------ ---------- ---------- ---------- ---------- ----------
         ---V------ ---------- ---------- ---------- ----A----- ----------
         ------SK-- ---------- ---L--EL-- ---------- ---------- ---------- - 601
```

```
                 10         20         30         40         50         60
                 |          |          |          |          |          |
GLS     EARGPTPEEA QREKDTRISK KMETMGIYFA TPEWVALNGH RGPSPGQLKY WQNTREIPDP
DS326   ---------- ---------- ---------- ---------- ---------- ----------
E/Del   ---------- ---------- ---------- ---------- ---------- ----------
D78     ---------- ---------- ---------- ---------- ---------- ----------
Cu-1    ---------- ---------K ---------- ---------- ---------- ----------
PBG98   ---------- -----A---- ---------- ---------- ---------- ----------
52/70   ---------- ---------- --------A- ---------- -------A-- ----------
STC     ---------- ---------- ---------- ---------- ---------- ----------
002-73  ---------- --A--A---- ---------- ---------- ---------- ----------
OH      ---------- ---------- ---------- ---------- ---------- ---E------

70         80         90        100        110
                 |          |          |          |          |
        NEDYLDYVHA EKSRLASEEQ ILRAATSIYG APGQAEPPQA FIDEVAKVYE INHGRGPNQE - 960
        ---------- ---------- -----K---- ---------- ---------- ----------
        ---------- ---------- ---------- ---------- ---------- ----------
        ---------- ----D----- ---------- ---------- ---------- --------G-
        ---------- ---------- ---------- ---------- ---------- ----------
        ---------- ---------- ---------- ---------- ---------- ----------
        ---------- -----K---- ---------- ---------- ---------- ----------
        ---------- ---------- ---------- ---------- ---------- ----------
        ---------- ---------- ---------- ---------- ---------- ----------
        ----P----- ---------- ---------- ---------- --R---T--- -----V----
```

FIG. 3I

```
                10         20         30         40         50
                 |          |          |          |          |
GLS       QMKDLLLTAM EMKHRNPRRA PPKPKPRPNA PTQRPPGRLG RWIRTVSDED LE  -1012
DS326     ---------- ---------- ----K----- ---------- ---------- --
E/Del     ---------- ---------- ----K----- ---------- ---------- --
D78       ---------- ---------- L---K----- ---------- ---------- --
Cu-1      ---------- ---------- L---K----- ---------- ---------- --
PBG98     ---------- ---------- L---K----- ---------- ---------- --
52/70     ---------- ---------- ----K----- ---------- ---------- --
STC       ---------- --L------- ----K----- ---------- ---------- --
002-73    ---------- ---------- ----K----- -S-------- ---------- --
OH        ---------- ---------- ----K----- -S-------- ---------- --
```

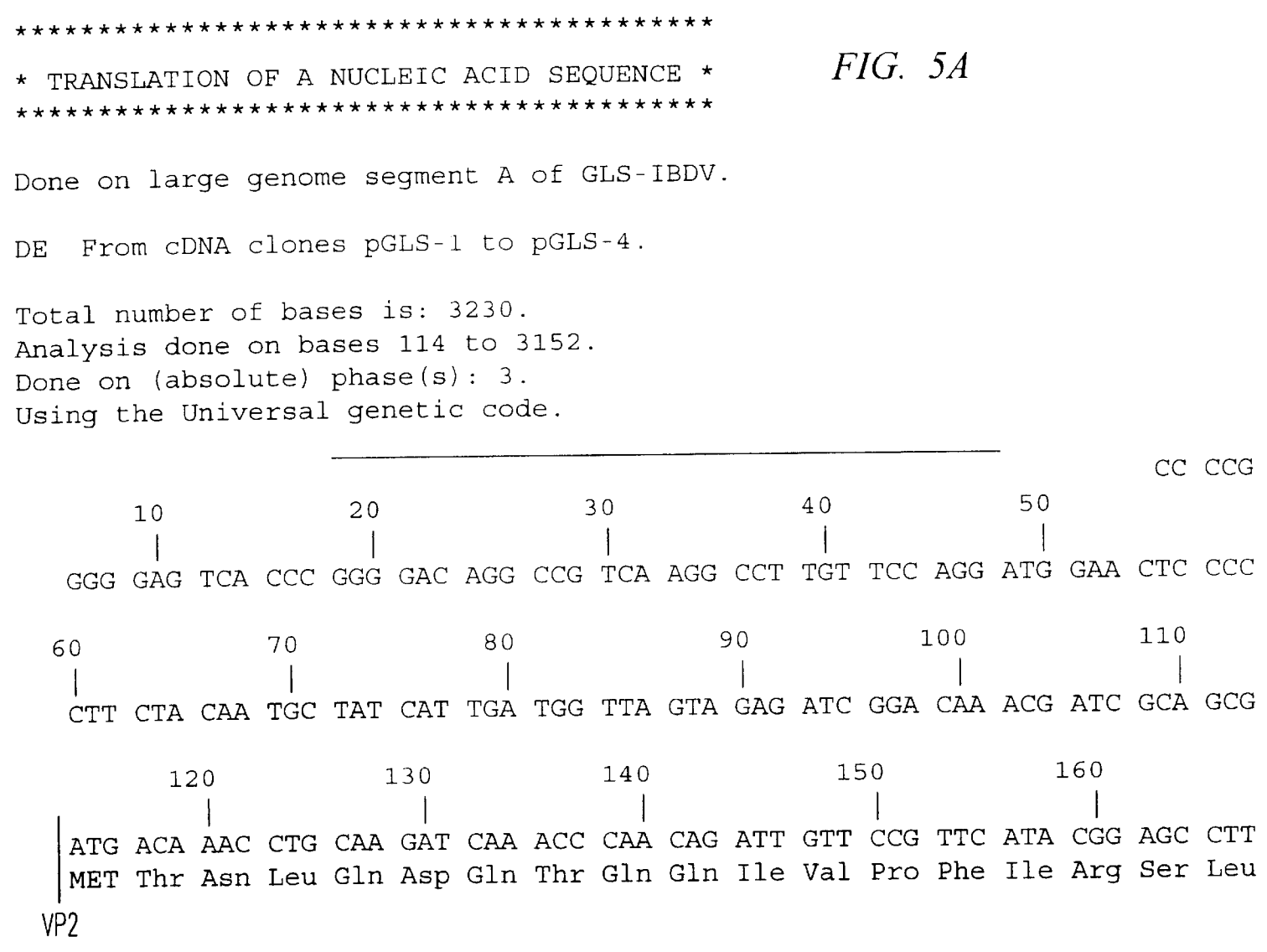

FIG. 5A

```
***************************************
* TRANSLATION OF A NUCLEIC ACID SEQUENCE *
***************************************

Done on large genome segment A of GLS-IBDV.

DE  From cDNA clones pGLS-1 to pGLS-4.

Total number of bases is: 3230.
Analysis done on bases 114 to 3152.
Done on (absolute) phase(s): 3.
Using the Universal genetic code.

CC CCG
       10        20         30         40         50
        |         |          |          |          |
  GGG GAG TCA CCC GGG GAC AGG CCG TCA AGG CCT TGT TCC AGG ATG GAA CTC CCC 60        70         80         90        100        110
  |         |          |          |          |          |
  CTT CTA CAA TGC TAT CAT TGA TGG TTA GTA GAG ATC GGA CAA ACG ATC GCA GCG 120        130        140        150        160
           |          |          |          |          |
 |ATG ACA AAC CTG CAA GAT CAA ACC CAA CAG ATT GTT CCG TTC ATA CGG AGC CTT
 |MET Thr Asn Leu Gln Asp Gln Thr Gln Gln Ile Val Pro Phe Ile Arg Ser Leu
VP2
```

CTG ATG CCA ACA ACC GGA CCG GCG TCC ATT CCG GAC GAC ACC CTG GAG AAG CAC
Leu MET Pro Thr Thr Gly Pro Ala Ser Ile Pro Asp Asp Thr Leu Glu Lys His

ACT CTC AGG TCA GAG ACC TCG ACC TAC AAT TTG ACT GTG GGG GAC ACA GGG TCA
Thr Leu Arg Ser Glu Thr Ser Thr Tyr Asn Leu Thr Val Gly Asp Thr Gly Ser

GGG CTA ATT GTC TTT TTC CCT GGA TTC CCT GGC TCA ATT GTG GGT GCT CAC TAC
Gly Leu Ile Val Phe Phe Pro Gly Phe Pro Gly Ser Ile Val Gly Ala His Tyr

ACA CTG CAG AGC AAT GGG TAC AAC TAC AAG TTC GAT CAG ATG CTG ACT GCC CAG
Thr Leu Gln Ser Asn Gly Tyr Asn Tyr Lys Phe Asp Gln MET Leu Leu Thr Ala Gln

AAC CTA CCG GCC AGC CTC CCT GGT GTT TAT GCA CTA AAC GGC ACC ATA AAC GCC
Asn Leu Pro Ala Ser Leu Pro Gly Val Tyr Ala Leu Asn Gly Thr Ile Asn Ala

AGG TCA AGC ACA CTC CCT GGT GGC GTT TAT GCA CTA AAC GGC AGT CTC ACA GTA
Arg Ser Ser Thr Leu Pro Gly Gly Val Tyr Ala Leu Asn Gly Ser Leu Thr Val

FIG. 5B

```
                                      500                 510                 520                 530                 540
                                       |                   |                   |                   |                   |
              GTG ACC TTC CAA GGA AGC CTG AGT GAA CTG ACA GAT GTT AGC TAC AAT GGG TTG
              Val Thr Phe Gln Gly Ser Leu Ser Glu Leu Thr Asp Val Ser Tyr Asn Gly Leu 550                 560                 570                 580                 590
           |                   |                   |                   |                   |
       ATG TCT GCA ACA GCC AAC ATC AAC GAC AAA ATT GGG AAC GTC CTA GTA GGG GAA
       MET Ser Ala Thr Ala Asn Ile Asn Asp Lys Ile Gly Asn Val Leu Val Gly Glu 600                 610                 620                 630                 640                 650
   |                   |                   |                   |                   |                   |
 GGG GTT ACT GTC CTC AGC TTA CCC ACA TCA TAT GAT CTT GGG TAT GTG AGG CTT
 Gly Val Thr Val Leu Ser Leu Pro Thr Ser Tyr Asp Leu Gly Tyr Val Arg Leu 660                 670                 680                 690                 700
               |                   |                   |                   |                   |
          GGT GAC CCC ATA CCC GCT ATA GGG CTT GAC CCA AAA ATG GTA GCA ACA TGT GAC
          Gly Asp Pro Ile Pro Ala Ile Gly Leu Asp Pro Lys MET Val Ala Thr Cys Asp 710                 720                 730                 740                 750                 760
       |                   |                   |                   |                   |                   |
   AGC AGT GAC AGG CCC AGA GTC TAC ACC ATA ACT GCA GCT GAT GAT TAC CAA TTC
   Ser Ser Asp Arg Pro Arg Val Tyr Thr Ile Thr Ala Ala Asp Asp Tyr Gln Phe 770                 780                 790                 800                 810
           |                   |                   |                   |                   |
       TCA TCA CAG TAC CAA ACA GGT GGG GTA ACA ATC ACC CTG TTC TCA GCC AAC ATT
       Ser Ser Gln Tyr Gln Thr Gly Gly Val Thr Ile Thr Leu Phe Ser Ala Asn Ile
```

FIG. 5C

```
      820         830         840         850         860
       |           |           |           |           |
GAT GCC ATC ACA AGC CTC AGC GTT GGG GGA GAG CTC GTG TTT AAA ACA AGC GTC
Asp Ala Ile Thr Ser Leu Ser Val Gly Gly Glu Leu Val Phe Lys Thr Ser Val 870         880         890         900         910         920
       |           |           |           |           |           |
CAC AGC CTT GTA CTG GGC ACC ATC TAC CTT ATA GGC TTT GAT GGG TCT GCG
His Ser Leu Val Leu Gly Thr Ile Tyr Leu Ile Gly Phe Asp Gly Ser Ala 930         940         950         960         970
       |           |           |           |           |
GTA ATC ACT AGA GCT GTG GCC GCA AAC AAT GGG CTG ACG ACC GGC ACC GAC AAT
Val Ile Thr Arg Ala Val Ala Ala Asn Asn Gly Leu Thr Thr Gly Thr Asp Asn 980         990        1000        1010        1020        1030
       |           |           |           |           |           |
CTT ATG CCA TTC AAT CTT GTG ATT CCA ACC AAC GAG ATA ACC CAG CCA ATC ACA
Leu MET Pro Phe Asn Leu Val Ile Pro Thr Asn Glu Ile Thr Gln Pro Ile Thr 1040        1050        1060        1070        1080
       |           |           |           |           |
TCC ATC AAA CTG GAG ATA GTG ACC TCC AAA AGT GGT GGG CAG GAA GGG GAC CAG
Ser Ile Lys Leu Glu Ile Val Thr Ser Lys Ser Gly Gly Gln Glu Gly Asp Gln 1090        1100        1110        1120        1130
       |           |           |           |           |
ATG TCA TGG TCG GCA AGT GGG AGC CTA GCA GTG ACG ATT CAT GGT GGC AAC TAT
MET Ser Trp Ser Ala Ser Gly Ser Leu Ala Val Thr Ile His Gly Gly Asn Tyr
```

```
1140        1150        1160        1170        1180        1190
 |           |           |           |           |           |
CCA GGG GCC CTC CGT CCC GTC ACA CTA GTA GCC TAC GAA AGA GTG GCA ACA GGA
Pro Gly Ala Leu Arg Pro Val Thr Leu Val Ala Tyr Glu Arg Val Ala Thr Gly 1200        1210        1220        1230        1240
 |           |           |           |           |
TCT GTC GTT ACG GTC GCT GGG GTG AGC AAC TTC GAG CTG ATC CCA AAT CCT GAA
Ser Val Val Thr Val Ala Gly Val Ser Asn Phe Glu Leu Ile Pro Asn Pro Glu 1250        1260        1270        1280        1290        1300
 |           |           |           |           |           |
CTA GCA AAG AAC CTG GTT ACA GAA TAC GGC CGA TTT GAC CCA GGA GCC ATG AAC
Leu Ala Lys Asn Leu Val Thr Glu Tyr Gly Arg Phe Asp Pro Gly Ala MET Asn 1310        1320        1330        1340        1350
 |           |           |           |           |
TAC ACA AAA TTG ATA CTG AGT GAG GAC CGC CTT GGC ATC AAG ACA GTC TGG
Tyr Thr Lys Leu Ile Leu Ser Glu Asp Arg Leu Gly Ile Lys Thr Val Trp 1360        1370        1380        1390        1400
 |           |           |           |           |
CCG ACA AGG GAG TAC ACC GAC TTT CGT GAG TAC TTC ATG GAG GTG GCC GAC CTC
Pro Thr Arg Glu Tyr Thr Asp Phe Arg Glu Tyr Phe MET Glu Val Ala Asp Leu 1410        1420        1430        1440        1450        1460
 |           |           |           |           |           |
AGC TCT CCC CTG AAG ATT GCA GGA GCA TTT GGC TTC AAA GAC ATA ATC CGG GCC
Ser Ser Pro Leu Lys Ile Ala Gly Ala Phe Gly Phe Lys Asp Ile Ile Arg Ala
```

FIG.5F

```
     1470                1480           1490              1500              1510
ATA AGG AGG ATA GCT GTG CCG GTG GTC TCC ACA TTG TTC CCA CCT GCC GCT CCC
Ile Arg Arg Ile Ala Val Pro Val Val Ser Thr Leu Phe Pro Pro Ala Ala Pro
         VP4

1520           1530              1540              1550              1560              1570
CTG GCC CAT GCA ATT GGG GAA GGT GTA GAC TAC CTG CTG GGT GAT GAG GCA CAG
Leu Ala His Ala Ile Gly Glu Gly Val Asp Tyr Leu Leu Gly Asp Glu Ala Gln 1580              1590              1600              1610              1620
GCT GCT TCA GGA ACT GCT CGA GCC GCG TCA GGA AAA GCA AGG GCT GCC TCA GGC
Ala Ala Ser Gly Thr Ala Arg Ala Ala Ser Gly Lys Ala Arg Ala Ala Ser Gly 1630              1640              1650              1660              1670
CGC ATA AGG CAG CTG ACT CTC GCC GCC GAC AAG GGG TAC GAG GTA GTC GCG AAT
Arg Ile Arg Gln Leu Thr Leu Ala Ala Asp Lys Gly Tyr Glu Val Val Ala Asn 1680              1690              1700              1710              1720              1730
CTA TTC CAG GTG CCC CAG AAT CCC GTA GTC GAC GGG ATT CTT GCT TCA CCC GGG
Leu Phe Gln Val Pro Gln Asn Pro Val Val Asp Gly Ile Leu Ala Ser Pro Gly 1740              1750              1760              1770              1780
ATA CTC CGC GGT GCA CAC AAC CTC GAC TGC GTG TTA AGA GAG GGC GCC ACG CTA
Ile Leu Arg Gly Ala His Asn Leu Asp Cys Val Leu Arg Glu Gly Ala Thr Leu
```

```
1790            1800            1810            1820            1830            1840
 |               |               |               |               |               |
TTC CCT GTG GTC ATC ACG ACA GTG GAA GAC GCC ATG ACA CCC AAA GCA CTA AAC
Phe Pro Val Val Ile Thr Thr Val Glu Asp Ala MET Thr Pro Lys Ala Leu Asn 1850            1860            1870            1880            1890
        |               |               |               |               |
AGC AAA ATG TTT GCT GTC ATT GAA GGC GTG CGA GAG GAC CTC CAA CCT CCA TCT
Ser Lys MET Phe Ala Val Ile Gly Gly Val Arg Glu Asp Leu Gln Pro Pro Ser 1900            1910            1920            1930            1940
        |               |               |               |               |
CAA AGA GGA TCC TTC ATA CGA ACT CTC TCC GGA CAC AGA GTC TAT GGA TAT GCT
Gln Arg Gly Ser Phe Ile Arg Thr Leu Ser Gly His Arg Val Tyr Gly Tyr Ala 1950            1960            1970            1980            1990            2000
  |               |               |               |               |               |
CCA GAT GGG GTA CTT CCA CTG GAG ACT GGG AGA GAC TAC ACC GTT GTC CCA ATA
Pro Asp Gly Val Leu Pro Leu Glu Thr Gly Arg Asp Tyr Thr Val Val Pro Ile 2010            2020            2030            2040            2050
        |               |               |               |               |
GAT GAT GTC TGG GAC GAC AGC ATT ATG CTG TCC AAA GAC CCC ATA CCT CCT ATT
Asp Asp Val Trp Asp Asp Ser Ile MET Leu Ser Lys Asp Pro Ile Pro Pro Ile 2060            2070            2080            2090            2100            2110
  |               |               |               |               |               |
GTG GGA AAC AGT GGA AAC CTA GCC ATA GCT TAC ATG GAT GTG TTT CGA CCC AAA
Val Gly Asn Ser Gly Asn Leu Ala Ile Ala Tyr MET Asp Val Phe Arg Pro Lys
```

```
                2120          2130          2140          2150          2160
                 |             |             |             |             |
GTC CCC ATC CAT GTG GCC ATG ACG GGA GCC CTC AAC GCT TGT GGC GAG ATT GAG
Val Pro Ile His Val Ala MET Thr Gly Ala Leu Asn Ala Cys Gly Glu Ile Glu 2170          2180          2190          2200          2210          2270
       |             |             |             |             |             |
AAA ATA AGC TTT AGA AGC ACC AAG GCC CTC ACC GCA CAC CGG CTT GGC CTC AAG
Lys Ile Ser Phe Arg Ser Thr Lys Leu Ala Thr Ala His Arg Leu Gly Leu Lys 2220          2230          2240          2250          2260
  |             |             |             |             |
TTG GCT GGT CCC GGA GCA TTT GAT GTA AAC ACC GGG CCC AAC TGG GCA ACG TTC
Leu Ala Gly Pro Gly Ala Phe Asp Val Asn Thr Gly Pro Asn Trp Ala Thr Phe 2280          2290          2300          2310          2320
           |             |             |             |             |
ATC AAA CGT TTC CCT CAC AAT CCA CGC GAC TGG GAC AGG CTC CCC TAC CTC AAC
Ile Lys Arg Phe Pro His Asn Pro Arg Asp Trp Asp Arg Leu Pro Tyr Leu Asn
         VP3

2330          2340          2350          2360          2370          2380
  |             |             |             |             |             |
CTT CCA TAC CTT CCA CCC AAT GCA GGA CTC CAG TAC CAC CTC GCC ATG GCC GCA
Leu Pro Tyr Leu Pro Pro Asn Ala Gly Leu Gln Tyr His Leu Ala MET Ala Ala 2390          2400          2410          2420          2430
       |             |             |             |             |
TCA GAG TTC AAG GAG ACC CCT GAA CTC GAG AGC GCC GTC AGG GCC ATG GAA GCA
Ser Glu Phe Lys Glu Thr Pro Glu Leu Glu Ser Ala Val Arg Ala MET Glu Ala
```

```
2440            2450            2460            2470            2480
 |               |               |               |               |
GCA GCC AGT GTA GAC CCA CTG TTC CAA TCT GCA CTC AGT GTG TTC ATG TGG CTG
Ala Ala Ser Val Asp Pro Leu Phe Gln Ser Ala Leu Ser Val Phe MET Trp Leu 2490            2500            2510            2520            2530            2540
 |               |               |               |               |               |
GAA GAG AAT GGG ATT GTG ACT GAC ATG GCC AAC TTC GCA CTC AGC GAC CCG AAC
Glu Glu Asn Gly Ile Val Thr Asp MET Ala Asn Phe Ala Leu Ser Asp Pro Asn 2550            2560            2570            2580            2590
 |               |               |               |               |
GCC CAT CGG ATG CGA AAC TTT CTT GCA AAC CAA CCA GGT AGC AAG TCT
Ala His Arg MET Arg Asn Phe Leu Ala Asn Gln Pro Gly Ser Lys Ser 2600            2610            2620            2630            2640            2650
 |               |               |               |               |               |
CAA AGG GCC AAA TAC GGG ACA GCA GGA GTG GAG GCC CGG GGC CCC ACA
Gln Arg Ala Lys Tyr Gly Thr Ala Gly Val Glu Ala Arg Gly Pro Thr 2660            2670            2680            2690            2700
 |               |               |               |               |
CCA GAA GAA GCA CAG AGG GAA AAA GAC ACA CGG ATC TCA AAG AAG ATG GAG ACC
Pro Glu Glu Ala Gln Arg Glu Lys Asp Thr Arg Ile Ser Lys Lys MET Glu Thr 2710            2720            2730            2740            2750
 |               |               |               |               |
ATG GGC ATC TAC TTT GCA ACA CCA GAA TGG GTA GCA CTC AAT GGG CAC CGA GGG
MET Gly Ile Tyr Phe Ala Thr Pro Glu Trp Val Ala Leu Asn Gly His Arg Gly
```

*FIG. 5I*

```
2760
  |
CCA AGC CCC GGC CAG CTA AAG TAC TGG CAG AAC ACA CGA GAA ATA CCG GAC CCA
Pro Ser Pro Gly Gln Leu Lys Tyr Trp Gln Asn Thr Arg Glu Ile Pro Asp Pro
         2770       2780        2790       2800       2810

2820
  |
AAC GAG GAC TAT CTA GAC TAC GTG CAT GCA GAG AAG AGC CGG TTG GCA TCA GAA
Asn Glu Asp Tyr Leu Asp Tyr Val His Ala Glu Lys Ser Arg Leu Ala Ser Glu
         2830       2840        2850       2860

2870
  |
GAA CAA ATC CTA AGG GCA GCT ACG TCG ATC TAC GGG GCT CCA GGA CAG GCA GAG
Glu Gln Ile Leu Arg Ala Ala Thr ser Ile Tyr Gly Ala Pro Gly Gln Ala Glu
         2880       2890        2900       2910       2920

2930
  |
CCA CCC CAA GCT TTC ATA GAC GAA CAG GTT GCC AAA GTC TAT GAA ATC AAC CAT GGA
Pro Pro Gln Ala Phe Ile Asp Glu Gln Val Ala Lys Val Tyr Glu Ile Asn His Gly
         2940       2950        2960       2970

2980
  |
CGT GGC CCA AAC CAA GAA CAA ATG CAG ATG AAA GAT CTG CTC TTG ACT GCG ATG GAG ATG
Arg Gly Pro Asn Gln Glu Gln MET Gln MET Lys Asp Leu Leu Leu Thr Ala MET Glu MET
         2990       3000        3010       3020

3030
  |
AAG CAT CGC AAT CCC AGG CGG GCT CCA CCA AAG CCC AAG CCC AGA CCC AAC GCT
Lys His Arg Asn Pro Arg Arg Ala Pro Pro Lys Pro Lys Pro Arg Pro Asn Ala
         3040       3050        3060       3070       3080
```

FIG. 5J

```
                    3090              3100              3110              3120              3130
                     |                 |                 |                 |                 |
              CCA ACG CAG AGA CCC CCT GGT CGG CTG GGC CGC TGG ATC AGG ACT GTC TCT GAT
              Pro Thr Gln Arg Pro Pro Gly Arg Leu Gly Arg Trp Ile Arg Thr Val Ser Asp 3140              3150              3160              3170              3180              3190
               |                 |                 |                 |                 |                 |
              GAG GAC CTT GAG TGA GGC TCC TGG GAG TCT CCC GAC ACC ACC CGC GCA GGC GTG
              Glu Asp Leu Glu - - -

3200              3210              3220              3230
                     |                 |                 |                 |
              GAC ACC AAT TCG GCC TTA CAA CAT CCC AAA TTG GAT CCG
              ---2 Aug - 1990 -----------------------------------------PC/Gene---
```

```
****************************************
* TRANSLATION OF A NUCLEIC ACID SEQUENCE *
****************************************

Done on DNA sequence EDEL22.

DE      E/DEL virus, vero cells adapted

Total number of bases is: 3180.
Analysis done on the complete sequence.
Done on (absolute) phase(s): 1.
Using the Universal genetic code.
```

```
                10          20          30          40          50
                 |           |           |           |           |
GAA TTC CTC CTT CTA CAA CGC TAT CAT TGA TGG TTA GTA GAG ATC AGA CAA ACG
--- --- --- --- --- --- --- --- --- --- --- --- --- --- --- --- --- ---

60          70          80          90         100
        |           |           |           |           |
ATC GCA GCG|ATG ACA AAC CTG CAA GAT CAA ACC CAC CAG ATT GTT CCG TTC ATA
--- --- ---|MET Thr Asn Leu Gln Asp Gln Thr His Gln Ile Val Pro Phe Ile
          VP2
110         120         130         140         150         160
 |           |           |           |           |           |
CGG AGC CTT CTG ATG CCA ACA ACC GGA CCG GCG TCC ATT CCG GAC GAC ACC CTG
Arg Ser Leu Leu MET Pro Thr Thr Gly Pro Ala Ser Ile Pro Asp Asp Thr Leu

```
            170                 180                 190                 200                 210
             |                   |                   |                   |                   |
GAG AAG CAC ACT CTC AGG TCA GAG ACC TCG ACC TAC AAT TTG ACT GTG GGG GAC
Glu Lys His Thr Leu Arg Ser Glu Thr Ser Thr Tyr Asn Leu Thr Val Gly Asp 220                 230                 240                 250                 260                 270
             |                   |                   |                   |                   |                   |
ACA GGG TCA GGG CTA ATT GTC TTT TTC CCT GGA TTC CCT GGC TCA ATT GTG GGT
Thr Gly Ser Gly Leu Ile Val Phe Phe Pro Gly Phe Pro Gly Ser Ile Val Gly 280                 290                 300                 310                 320
             |                   |                   |                   |                   |
GCT CAC TAC ACA CTG CAG AGC AGT GGG AAC TAC AAG TTC GAT CAG ATG CTC CTG
Ala His Tyr Thr Leu Gln Ser Ser Gly Asn Tyr Lys Phe Asp Gln MET Leu Leu 330                 340                 350                 360                 370
             |                   |                   |                   |                   |
ACT GCC CAG AAC CTA CCG GCC AGC TAC AAC TAC TGC AGG CTA GTG AGT CGG AGT
Thr Ala Gln Asn Leu Pro Ala Ser Tyr Asn Tyr Cys Arg Leu Val Ser Arg Ser 380                 390                 400                 410                 420                 430
             |                   |                   |                   |                   |                   |
CTC ACA GTA AGG TCA AGC ACA CTC CCT GGT GGC GTT TAT GCA CTA AAC GGC ACC
Leu Thr Val Arg Ser Ser Thr Leu Pro Gly Gly Val Tyr Ala Leu Asn Gly Thr
```

*FIG. 6B*

```
440                450                460                470                480
 —                  —                  —                  —                  —
ATA AAC GCC GTG ACC TTC CAA GGA AGC CTG AGT GAA CTG ACA GAT GTT AGC TAC
Ile Asn Ala Val Thr Phe Gln Gly Ser Leu Ser Glu Leu Thr Asp Val Ser Tyr 490                500                510                520                530                540
 —                  —                  —                  —                  —                  —
AAC GGG TTG ATG TCT GCA ACA GCC AAC ATC AAC GAC AAA ATT GGG AAC GTC CTA
Asn Gly Leu MET Ser Ala Thr Ala Asn Ile Asn Asp Lys Ile Gly Asn Val Leu 550                560                570                580                590
 —                  —                  —                  —                  —
GTA GGG GAA GGG GTA ACC GTC CTC AGC TTA CCC ACA TCA TAT GAT CTT GGG TAT
Val Gly Glu Gly Val Thr Val Leu Ser Leu Pro Thr Ser Tyr Asp Leu Gly Tyr 600                610                620                630                640
 —                  —                  —                  —                  —
GTG AGG CTT GGT GAC AGT GAC CCC ATA CCC GCT ATA GGG CTT GAC CCA AAA ATG GTA GCA
Val Arg Leu Gly Asp Ser Asp Pro Ile Pro Ala Ile Gly Leu Asp Pro Lys MET Val Ala 650                660                670                680                690                700
 —                  —                  —                  —                  —                  —
ACA TGT GAC AGC AGT GAC AGG CCC AGA GTC TAC ACC ATA ACT GCA GCC GAT AAT
Thr Cys Asp Ser Ser Asp Arg Pro Arg Val Tyr Thr Ile Thr Ala Ala Asp Asn
```

*FIG. 6C*

TAC CAA TTC TCA TCA CAG TAC CAA ACA GGT GGG GTA ACA ATC ACA CTG TTC TCA
Tyr Gln Phe Ser Ser Gln Tyr Gln Thr Gly Gly Val Thr Ile Thr Leu Phe Ser

GCC AAC ATT GAT GCC ATC ACA AGT CTC AGC GTT GGG GGA GAG CTC GTG TTC AAA
Ala Asn Ile Asp Ala Ile Thr Ser Leu Ser Val Gly Gly Glu Leu Val Phe Lys

ACA AGC GTC CAA AGC CTT GTA CTG GGC GCC ACC ATC TAC CTT ATA GGC TTT GAT
Thr Ser Val Gln Ser Leu Val Leu Gly Ala Thr Ile Tyr Leu Ile Gly Phe Asp

GGG ACT GCG GTA ATC ACC AGA GCT GTG GCC GCA AAC AAT GGG CTG ACG GCC GGC
Gly Thr Ala Val Ile Thr Arg Ala Val Ala Ala Asn Asn Gly Leu Thr Ala Gly

ATC GAC AAT CTT ATG CCA TTC AAT CTT GTG ATT CCA ACC AAT GAG ATA ACC CAG
Ile Asp Asn Leu MET Pro Phe Asn Leu Val Ile Pro Thr Asn Glu Ile Thr Gln

FIG. 6D

```
     980            990           1000           1010           1020
      |              |              |              |              |
CCA ATC ACA TCC ATC ATA CTG GAG ATA GTG ACC TCC AAA AGT GAT GGT CAG GCA
Pro Ile Thr Ser Ile Ile Leu Glu Ile Val Thr Ser Lys Ser Asp Gly Gln Ala 1030           1040           1050           1060           1070           1080
      |              |              |              |              |              |
GGG GAA CAG ATG TCA TGG TCG GCA AGT GGG AGC CTA GCA GTG ACG ATC CAT GGT
Gly Glu Gln MET Ser Trp Ser Ala Ser Gly Ser Leu Ala Val Thr Ile His Gly 1090           1100           1110           1120           1130
      |              |              |              |              |
GGC AAC TAT CCA GGA GCC CTC CGT CCC GTC ACA CTA GTG GCC TAC GAA AGA GTG
Gly Asn Tyr Pro Gly Ala Leu Arg Pro Val Thr Leu Val Ala Tyr Glu Arg Val 1140           1150           1160           1170           1180
      |              |              |              |              |
GCA ACA GGA TCT GTC GTT ACG GTC GCT GGG GTG AGC AAC TTC GAG CTG ATC CCA
Ala Thr Gly Ser Val Val Thr Val Ala Gly Val Ser Asn Phe Glu Leu Ile Pro 1190           1200           1210           1220           1230           1240
      |              |              |              |              |              |
AAT CCT GAA CTA GCA AAG AAC CTG GTT ACA GAA TAC GGC CGA TTT GAC CCA GGA
Asn Pro Glu Leu Ala Lys Asn Leu Val Thr Glu Tyr Gly Arg Phe Asp Pro Gly
```

```
                1250            1260            1270            1280            1290
                 |               |               |               |               |
GCC ATG AAC TAC ACG AAA TTG ATA CTG AGT GAG AGG GAC CAC CTT GGC ATC AAG
Ala MET Asn Tyr Thr Lys Leu Ile Leu Ser Glu Arg Asp His Leu Gly Ile Lys 1300            1310            1320            1330            1340            1350
                 |               |               |               |               |               |
ACC GTC TGG CCA ACA AGG GAG TAC ACT GAC TTT CGT GAG TAC TTC ATG GAG GTG
Thr Val Trp Pro Thr Arg Glu Tyr Thr Asp Phe Arg Glu Tyr Phe MET Glu Val 1360            1370            1380            1390            1400
                 |               |               |               |               |
GCC GAC CTC AAC TCT CCC CTG AAG ATT GCA GGA GCA TTT GGC TTC AAA GAG ATA
Als Asp Leu Asn Ser Pro Leu Lys Ile Ala Gly Ala Phe Gly Phe Lys Asp Ile 1410            1420            1430            1440            1450
                 |               |               |               |               |
ATC CGG GCC ATA AGG|AGG ATA GCT GTA CCG GTG TCT ACA TTG TTC CCA CCT
Iel Arg Ala Ile Arg|Arg Ile Ala Val Pro Val Ser Thr Leu Phe Pro Pro
                   VP4

1460            1470            1480            1490            1500            1510
                 |               |               |               |               |               |
GCC GCT CCT CTA GCC CAT GCA ATT GGG GAA GGT GTA GAC TAC CTA CTG GGC GAT
Ala Ala Pro Leu Ala His Ala Ile Gly Glu Gly Val Asp Tyr Leu Leu Gly Asp
```

```
      1520                1530                1540                 1550                 1560
       |                   |                   |                    |                    |
GAG GCA CAG GCT GCT TCA GGA ACC GCT CGA GCC GCG TCA GGA AAA GCA AGG GCT
Glu Ala Gln Ala Ala Ser Gly Thr Ala Arg Ala Ala Ser Gly Lys Ala Arg Ala 1570                1580                1590                 1600                 1610                 1620
       |                   |                   |                    |                    |                    |
GCC TCA GGC CGC ATA AGG CAG CTG ACT CTC GCC GCC GAC AAG GGG TAC GAG GTA
Ala Ser Gly Arg Ile Arg Gln Leu Thr Leu Ala Ala Asp Lys Gly Tyr Glu Val 1630                1640                1650                 1660                 1670
       |                   |                   |                    |                    |
GTC GCG AAT CTA TTC CAG GTG CCC CAG AAT CCC GTA GTC GAC GGG ATT CTT GCT
Val Ala Asn Leu Phe Gln Val Pro Gln Asn Pro Val Val Asp Gly Ile Leu Ala 1680                1690                1700                 1710                 1720
       |                   |                   |                    |                    |
TCA CCC GGG ATA CTT CGC GGT GCA CAC AAC CTC GAC TGC GTG CTA AGA GAG GGT
Ser Pro Gly Ile Leu Arg Gly Ala His Asn Leu Asp Cys Val Leu Arg Glu Gly 1730                1740                1750                 1760                 1770                 1780
       |                   |                   |                    |                    |                    |
GCC ACG CTA TTC CCT GTG GTC ATT ACG ACA GTG GAA GAC GCC ATG ACA CCC AAA
Ala Thr Leu Phe Pro Val Val Ile Thr Thr Val Glu Asp Ala MET Thr Pro Lys
```

*FIG. 6G*

```
                     1790                1800                1810                1820                1830
                      |                   |                   |                   |                   |
GCA CTG AAC AGC AAA ATG TTT GCT GTC ATT GAA GGC GTG CGA GAA GAC CTC CAA
Ala Leu Asn Ser Lys MET Phe Ala Val Ile Glu Gly Val Arg Glu Asp Leu Gln 1840                1850                1860                1870                1880                1890
          |                   |                   |                   |                   |                   |
CCT CCA TCT CAA AGA GGA TCC TTC ATA CGA ACT CTC TCC GGA CAC AGA GTC TAT
Pro Pro Ser Gln Arg Gly Ser Phe Ile Arg Thr Leu Ser Gly His Arg Val Tyr 1900                1910                1920                1930                1940
          |                   |                   |                   |                   |
GGA TAT GCT CCA GAT GGG GTA CTT CCA CTG GAG ACT GGG AGA GAC TAC ACC GTT
Gly Tyr Ala Pro Asp Gly Val Leu Pro Leu Glu Thr Gly Arg Asp Tyr Thr Val 1950                1960                1970                1980                1990
          |                   |                   |                   |                   |
GTC CCA ATA GAT GAT CCA GAT GTC TGG GAC GAC AGC ATT ATG CTG TCC AAG GAC CCC ATA
Val Pro Ile Asp Asp Pro Asp Val Trp Asp Asp Ser Ile MET Leu Ser Lys Asp Pro Ile 2000                2010                2020                2030                2040                2050
 |                   |                   |                   |                   |                   |
CCT CCT ATT GTG GGA AAC AGT GGA AAC CTA GCC ATA GCT TAC ATG GAT GTG TTT
pro Pro Ile Val Gly Asn Ser Gly Asn Leu Ala Ile Ala Tyr MET Asp Val Phe
```

```
     2060              2070              2080              2090              2100
      |                 |                 |                 |                 |
CGA CCC AAA GTC CCC ATC CAT GTG GCC ATG ACG GGA GCC CTC AAC GCT TGT GGC
Arg Pro Lys Val Pro Ile His Val Ala Met Thr Gly Ala Leu Asn Ala Cys Gly 2110              2120              2130              2140              2150              2160
      |                 |                 |                 |                 |                 |
GAG ATT GAG AAA ATA AGC TTC AGA AGC ACC AAG CTC GCC ACC GCA CAC CGG CTT
Glu Ile Glu Lys Ile Ser Phe Arg Ser Thr Lys Leu Ala Thr Ala His Arg Leu 2170              2180              2190              2200              2210
      |                 |                 |                 |                 |
GGC CTC AAG TTG GCT GGT CCC GGA GCA TTC GAT GTA AAC ACC GGG CCC AAC TGG
Gly Leu Lys Leu Ala Gly Pro Gly Ala Phe Asp Val Asn Thr Gly Pro Asn Trp 2220              2230              2240              2250              2260
      |                 |                 |                 |                 |
GCA ACG TTC ATC AAA CGT TTC CCT CAC AAT CCA CGC GAC TGG GAC AGG CTC CCC
Ala Thr Phe Ile Lys Arg Phe Pro His Asn Pro Arg Asp Trp Asp Arg Leu Pro
                        VP3

2270              2280              2290              2300              2310              2320
      |                 |                 |                 |                 |                 |
TAC CTC AAC CTT CCA TAC CTT CCA CCC AAT GCA GGA CGC CAG TAC CAC CTT GCC
Tyr Leu Asn Leu Pro Tyr Leu Pro Pro Asn Ala Gly Arg Gln Tyr His Leu Ala
```

```
     2330            2340            2350            2360            2370
      |               |               |               |               |
ATG GCT GCA TCA GAG TTT AAA GAG ACC CCT GAA CTC GAG AGC GCC GTC AGA GCC
MET Ala Ala Ser Glu Phe Lys Glu Thr Pro Glu Leu Glu Ser Ala Val Arg Ala 2380            2390            2400            2410            2420            2430
      |               |               |               |               |               |
ATG GAA GCA GCA GCC AAT GTG GAC CCA CTG TTC CAA TCT GCA CTC AGT GTG TTC
MET Glu Ala Ala Ala Asn Val Asp Pro Leu Phe Gln Ser Ala Leu Ser Val Phe 2440            2450            2460            2470            2480
      |               |               |               |               |
ATG TGG CTG GAA GAG AAT GGG ATT GTG GCT GAC ATG GCC AAT TTC GCA CTC AGC
MET Trp Leu Glu Glu Asn Gly Ile Val Ala Asp MET Ala Asn Phe Ala Leu Ser 2490            2500            2510            2520            2530
      |               |               |               |               |
GAC CCG AAC GCC CAT CGG ATG CGA AAT TTT CTT GCA AAC GCA CCA CAA GCA GGC
Asp Pro Asn Ala His Arg MET Arg Asn Phe Leu Ala Asn Ala Pro Gln Ala Gly 2540            2550            2560            2570            2580            2590
      |               |               |               |               |               |
AGC AAG TCG CAA AGG GCC AAG TAC GGG ACA GCA GGC TAC GGA TGT GAG GCC CGG
Ser Lys Ser Gln Arg Ala Lys Tyr Gly Thr Ala Gly Tyr Gly Val Glu Ala Arg
```

FIG. 6J

```
                2600            2610            2620            2630            2640
                  |               |               |               |               |
GGC CCC ACA CCA GAG GAA GCA CAG AGG GAA AAA GAC ACA CGG ATC TCA AAG AAG
Gly Pro Thr Pro Glu Glu Ala Gln Arg Glu Lys Asp Thr Arg Ile Ser Lys Lys 2650            2660            2670            2680            2690            2700
                  |               |               |               |               |               |
ATG GAG ACC ATG GGC ATC TAC TTT GCA ACA CCA GAA TGG GTA GCA CTC AAT GGG
MET Glu Thr MET Gly Ile Tyr Phe Ala Thr Pro Glu Trp Val Ala Leu Asn Gly 2710            2720            2730            2740            2750
                  |               |               |               |               |
CAC CGA GGG CCA AGC CCC GGC CAG CTA AAG TAC TGG CAG AAC ACA CGA GAA ATA
His Arg Gly Pro Ser Pro Gly Gln Leu Lys Tyr Trp Gln Asn Thr Arg Glu Ile 2760            2770            2780            2790            2800
                  |               |               |               |               |
CCG GAC CCA AAC GAG GAC TAT CTA GAC TAC GTG CAT GCA GAG AAG AGC CGG TTG
Pro Asp Pro Asn Glu Asp Tyr Leu Asp Tyr Val His Ala Glu Lys Ser Arg Leu 2810            2820            2830            2840            2850            2860
                  |               |               |               |               |               |
GCA TCA GAA GAA CAA ATC CTA AAG GCA GCT ACG TCG ATC TAC GGG GCT CCA GGA
Ala Ser Glu Glu Gln Ile Leu Lys Ala Ala Thr Ser Ile Tyr Gly Ala Pro Gly
```

*FIG. 6K*

```
              2870                2880                2890                2900                2910
               |                   |                   |                   |                   |
CAG GCA GAG CCA CCC CAA GCT TTC ATA GAC GAA GTT GCC AAA GTC TAT GAA ATC
Gln Ala Glu Pro Pro Gln Ala Phe Ile Asp Glu Val Ala Lys Val Tye Glu Ile 2920                2930                2940                2950                2960                2970
      |                   |                   |                   |                   |                   |
AAC CAT GGA CGT GGC CCT AAC CAA GAA CAG ATG AAA GAT CTG CTC TTG ACT GCA
Asn His Gly Arg Gly Pro Asn Gln Glu Gln MET Lys Asp Leu Leu Leu Thr Ala 2980                2990                3000                3010                3020
               |                   |                   |                   |                   |
ATG GAG ATG AAG CAT CGC AAC CCC AGG CGG GCT CCA CCA AAG CCC AAA CCA AAA
MET Glu MET Lys His Arg Asn Pro Arg Arg Ala Pro Pro Lys Pro Lys Pro Lys 3030                3040                3050                3060                3070
      |                   |                   |                   |                   |
CCC AAT GCT CCA ACA CAG AGA CCC CCT GGT CGG CTG GGC CGC TGG ATC AGG ACC
Pro Asn Ala Pro Thr Gln Arg Pro Pro Gly Arg Leu Gly Arg Trp Ile Arg Thr 3080                3090                3100                3110                3120                3130
               |                   |                   |                   |                   |                   |
GTC TCT GAT GAG GAC CTT GAG TGA GGC CCC TGG GGG TCT CCC GAC ACC ACC CGC
Val Ser Asp Glu Asp Leu Glu --- --- --- --- --- --- --- --- --- --- ---
```

*FIG. 6L*

```
       3140          3150          3160          3170          3180
        |             |             |             |             |
GCA GGC GTG GAC ACC AAT TCG GCC TTA CAA CAT CCC AAA TTG GAT CCG
 |   |   |   |   |   |   |   |   |   |   |   |   |   |   |   |
===24-AUG-1992======================================PC/GENE===
```

*FIG. 6M*

AMINO ACID CHANGES IN VP2 VARIOUS IBDV STRAINS

AMINO ACID RESIDUE NUMBER IN VP2

FIG. 7A

| VIRUSES | 5 | 74 | 76 | 80 | 213 | 222 | 239 | 242 | 249 | 253 | 254 | 258 | 263 | 264 | 269 | 270 | 272 | 279 |
|---|---|---|---|---|---|---|---|---|---|---|---|---|---|---|---|---|---|---|
| GLS | Gln | Leu | Ser | Tyr | Asp | Thr | Ser | Val | Lys | His | Ser | Gly | Leu | Ile | Ser | Ala | Ile | Asn |
| DS326 | " | " | " | " | " | Ser | " | " | " | Gln | " | " | " | " | Thr | " | " | " |
| E/DEL | " | " | " | " | Asn | Thr | " | " | " | " | " | " | " | " | " | Thr | " | " |
| D78 | " | " | Gly | " | Asp | Pro | " | " | Gln | His | Gly | " | " | " | " | " | " | " |
| Cu-1 | " | " | Ser | " | " | " | " | " | Arg | " | " | " | " | " | " | " | " | " |
| PBG98 | " | " | " | " | " | " | " | Ile | Gln | Gln | " | " | " | " | " | " | " | " |
| 52/70 | " | " | " | " | " | " | " | Val | " | " | " | " | Phe | " | " | Ala | " | Asp |
| STC | " | " | " | Leu | " | " | " | " | " | " | " | Asn | Leu | Val | " | Thr | Thr | " |
| 002-73 | Ser | Met | " | Tyr | " | " | Asn | " | " | " | " | " | " | " | " | " | Thr | Gly |

FIG. 7B

| VIRUSES | 280 | 284 | 286 | 279 | 299 | 305 | 311 | 312 | 318 | 320 | 321 | 323 | 326 | 328 | 330 | 332 | 433 |
|---|---|---|---|---|---|---|---|---|---|---|---|---|---|---|---|---|---|
| GLS | Asn | Thr | Thr | Pro | Asn | Ile | Glu | Ile | Gly | Gln | Glu | Asp | Ser | Ser | Ser | Ser | Ser |
| DS326 | " | Ala | " | " | " | " | Lys | " | " | " | " | " | " | " | " | " | Asn |
| E/DEL | " | " | Ile | " | " | " | Glu | " | Asp | Leu | " | Glu | " | " | Arg | " | " |
| D78 | " | Thr | Thr | " | " | " | " | " | Gly | Gln | Ala | Asp | " | " | Lys | " | " |
| Cu-1 | " | " | " | Ser | " | " | " | " | " | " | " | " | " | " | Arg | " | " |
| PBG98 | Thr | " | " | Pro | " | " | " | " | " | " | " | " | Leu | " | Ser | " | " |
| 52/70 | Asn | Ala | " | " | " | " | " | " | " | " | " | " | Ser | " | " | " | " |
| STC | " | " | " | " | " | " | " | Lys | " | " | " | " | " | Leu | " | Asn | " |
| 002-73 | " | " | " | " | " | Val | " | Glu | " | " | " | " | " | " | " | " | " |

1

CHIMERIC INFECTIOUS BURSAL DISEASE VIRUS CDNA CLONES, EXPRESSION PRODUCTS AND VACCINES BASED THEREON

This application is a division and claims priority of U.S. patent application Ser. No. 08/219,262, filed Mar. 29, 1994, now U.S. Pat. No. 5,788,970, and this entire disclosure is incorporated herein by reference.

BACKGROUND OF THE INVENTION

1. Field of the Invention

The present invention provides chimeric IBDV immunogens which actively protect against virulent and lethal challenge by Classic and variant IBDV strains, and methods for obtaining vaccines containing these chimeric immunogens and vaccines.

2. Discussion of the Background

Infectious bursal disease virus (IBDV) is responsible for a highly contagious immunosuppressive disease in young chickens which causes significant losses to the poultry industry worldwide (reviewed in Kibenge (1988) "J. Gen. Virol.", 69:1757–1775). Infection of susceptible chickens with virulent IBDV strains can lead to a highly contagious immunosuppressive condition known as infectious bursal disease (IBD). Damage caused to the lymphoid follicles of the bursa of Fabricius and spleen can exacerbate infections caused by other agents and reduce a chicken's ability to respond to vaccination as well (Cosgrove (1962) "Avian Dis.", 6:385–3894).

There are two serotypes of IBDV (McFerran et al (1980) "Avian Path.", 9:395–404). Serotype 1 viruses are pathogenic to chickens and differ markedly in their virulence (Winterfield et al (1978) "Avian Dis.", 5:253–260), whereas serotype 2 viruses, isolated from turkeys, are avirulent for chickens (Ismail et al (1988) "Avian Dis.", 32:757–759; Kibenge (1991) "Virology", 184:437–440).

IBDV is a member of the Birnaviridae family and its genome consists of two segments of double-stranded RNA (Dobos et al (1979) "J. Virol.", 32:593–605). The smaller segment B (~2800 bp) encodes VP1, the dsRNA polymerase. The larger genomic segment A (~3000 bp) encodes a 110 kDa precursor polyprotein in a single open reading frame (ORF) that is processed into mature VP2, VP3 and VP4 (Azad et al (1985) "Virology", 143:35–44). From a small ORF partly overlapping with the polyprotein ORF, segment A can also encode VP5, a 17 kDa protein of unknown function (Kibenge et al (1991) "J. Gen. Virol.", 71:569–577).

While VP2 and VP3 are the major structural proteins of the virion, VP2 is the major host-protective immunogen and causes induction of neutralizing antibodies (Becht et al (1988) "J. Gen. Virol.", 69:631–640; Fahey et al (1989) "J. Gen. Virol.", 70:1473–1481). VP3 is considered to be a group-specific antigen because it is recognized by monoclonal antibodies (Mabs) directed against VP3 from strains of both serotype 1 and 2 (Becht et al (1988) "J. Gen. Virol.", 69:631–640). VP4 is a virus-coded protease and is involved in the processing of the precursor protein (Jagadish et al (1988) "J. Virol.", 62:1084–1087).

In the past, control of IBDV infection in young chickens has been achieved by live vaccination with avirulent strains, or principally by the transfer of maternal antibody induced by the administration of live and killed IBDV vaccines to breeder hens. Unfortunately, in recent years, virulent variant strains of IBDV have been isolated from vaccinated flocks in the United States (Snyder et al (1988b) "Avian Dis.", 32:535–539; Van der Marel et al (1990) "Dtsch. Tierarztl. Wschr.", 97:81–83). The use of a select panel of Mabs, raised against various strains of IBDV, has led to the identification of naturally occurring GLS, DS326, RS593 and Delaware variant viruses in the United States. Substantial economic losses have been sustained due to the emergence of these antigenic variants (Delaware and GLS) in the field (Snyder et al (1992) "Arch. Virol.", 127:89–101, copending U.S. application Ser. No. 08/216,841, filed Mar. 24, 1994, Attorney Docket No. 2747-053-27, Snyder, copending herewith). These variant strains are antigenically different from the Classic strains of IBDV most typically isolated before 1985, and lack epitope(s) defined by neutralizing monoclonal antibodies (Mabs) B69 and R63 (Snyder et al (1988a) "Avian Dis.", 32:527–534; Snyder et al (1998b) "Avian Dis.", 32:535–539; Snyder et al (1992) "Arch. Virol.", 127:89–101). Since the appearance of these variant strains in the field, many commercially available live and killed vaccines for IBDV have been reformulated in an attempt to better match the greater antigenic spectrum of viruses recognized to be circulating in the field.

Efforts to develop a recombinant vaccine for IBDV have been made, and the genome of IBDV has been cloned (Azad et al (1985) "Virology", 143:35–44). The VP2 gene of IBDV has been cloned and expressed in yeast (Macreadie et al (1990) "Vaccine", 8:549–552), as well as in a recombinant fowlpox virus (Bayliss et al (1991) "Arch. Virol.", 120:193–205). When chickens were immunized with the VP2 antigen expressed from yeast, antisera afforded passive protection in chickens against IBDV infection. When used in active immunization studies, the fowlpox virus-vectored VP2 antigen afforded protection against mortality, but not against damage to the bursa of Fabricius.

Recently, the synthesis of VP2, VP3 and VP4 structural proteins of the variant GLS IBDV strain in a baculovirus expression system has been described (Vakharia et al (1993) "J. Gen. Virol.", 74:1201–1206). In an initial two dose active immunity study in SPF chickens, baculovirus expressed GLS proteins were able to confer 79% protection against virulent GLS challenge (Vakharia et al (1993) "J. Gen. Virol.", 74:1201–1206). In a subsequent extended study of active cross-immunity, by increasing the antigenic mass of the baculovirus expressed CLS protein, complete protection against the variant GLS and E/Del strains was obtained with a single dose, but only partial protection was afforded against the Classic STC strain unless two doses were administered.

In recent years, the complete, nucleotide sequences of the large segment A of five serotype 1 IBDV strains; 002-73 (Hudson et al (1986) "Nucleic Acids Res.", 14:001–5012), Cu-1, PBG98, 52/70 (Bayliss et al (1990) "J. Gen. Virol.", 71:1303–1312), STC (Kibenge (1990) "J. Gen. Virol.", 71:569–577), and serotype 2 OH strain (Kibenge (1991) "Virology", 184:437–440) have been determined. In addition, the VP2 gene of virulent Japanese IBDV strains (Lin et al (1993) "Avian Dis.", 37:315–323) and Delaware variants A and E (Lana et al (1992) "Virus Genes", 6:247–259; Heine et al (1991) "J. Gen. Virol.", 22:1835–1843) have been sequenced. However, noone has completely cloned and characterized the entire long segment of any United States IBDV variant.

SUMMARY OF THE INVENTION

The inventors have now identified the region of the IBDV genome which is responsible for antigenic variation. A DNA sequence containing the central variable region of VP2 protein, as well as a plasmid incorporating the same, have been constructed. This DNA sequence can be manipulated to generate desired virus neutralizing epitopes or immunogenic polypeptides of any IBDV strain. In turn, these immunogenic segments can be incorporated into new recombinant IBDV vaccines.

BRIEF DESCRIPTION OF THE DRAWINGS

FIG. 5 reflects the DNA (SEQ ID NO:11) and amino acid sequence (SEQ ID NO:12) for the GLS virus structural protein fragment VP2/VP4/VP3. A vertical line indicates the start/stop points for the VP2, VP4 and VP3 regions.

FIG. 6 reflects the DNA (SEQ ID NO:13) and amino acid sequence (SEQ ID NO:14) for the E/Del 22 virus structural protein fragment VP2/VP4/VP3.

FIG. 7 is a table of the amino acid identities for key locations (epitopic determinants) of eight different IBDV.

DEFINITIONS

IBD—infectious bursal disease as described above.

IBDV—infectious bursal disease virus, a virus capable of, at a minimum, inducing lesions in the bursa of Fabricius in infected poultry.

Epitopic Determinants—amino acids or amino acid sequences which correspond to epitopes recognized by one or more monoclonal antibodies. Presence of the amino acid or amino acid sequence at the proper ORF location causes the polypeptide to exhibit the corresponding epitope. An epitopic determinant is identified by amino acid(s) identity and sequence location.

Genetic Epitopic Determinants—nucleotide sequences of the ORF which encode epitopic determinants.

Conformational Epitopes—epitopes induced, in part or in whole, by the quaternary (three-dimensional) structure of an IBDV polypeptide. Conformational epitopes may strengthen binding between an IBDV and a monoclonal antibody, or induce binding whereas the same sequence, lacking the conformational epitope, would not induce binding between the antibody and the IBDV polypeptide at all.

Virus-Like Particles—three-dimensional particles of natural or recombinant amino acid sequences mimicking the three-dimensional structure of IBDV (encoded by the large genome segment A) but lacking viral RNA. Virus-like particles exhibit conformational epitopes exhibited by native viruses of similar sequence. Virus-like particles are created by the proper expression of DNA encoding VP2, VP4, VP3 structural proteins in a proper ORF.

Epitopic Determinant Region—Limited region of amino acid sequence of VP2 of IBDV that is replete with epitopic determinants, variation among amino acids of this limited region giving rise to a high number of epitopes recognized by different monoclonal antibodies.

DETAILED DESCRIPTION OF THE PREFERRED EMBODIMENTS

Figure 1A:
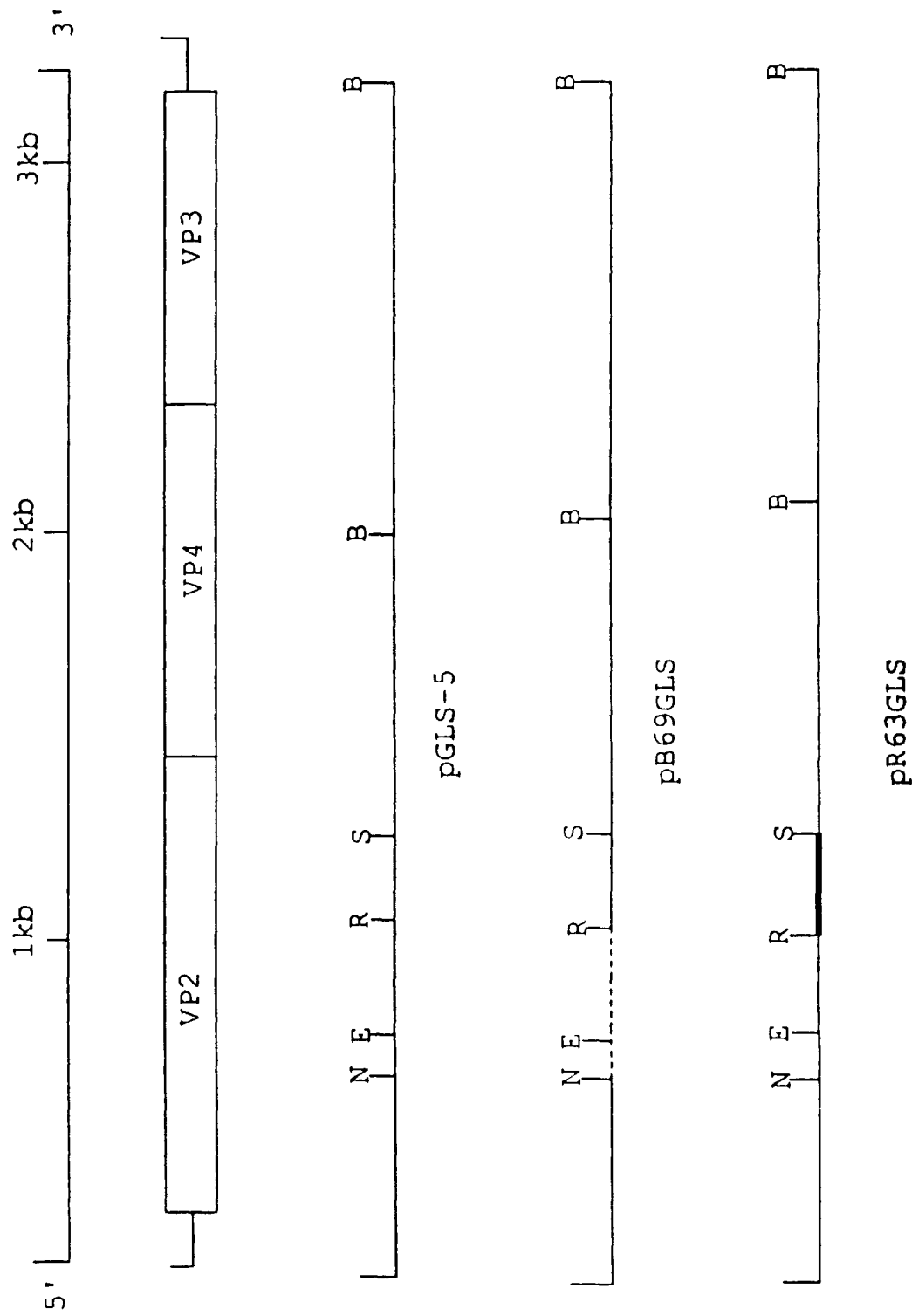
FIG. 1 illustrates the construction of various chimeric plasmids encoding IBDV-specific polyproteins. A map of the IBDV genome with its coding regions is shown at the top of the Figure. Selected restriction sites are incorporated in the Figure: B, BamHI; E, BstEII; N, NdeI; R, NarI; S, SpeI. Dashes indicate the substitution of the D78 sequence (NdeI-NarI fragment) into the GLS sequence to restore the B69 epitope region. Solid line and dotted line indicate the substitution of the E/Del-22 and DS326 sequences, respectively, into the GLS sequence to restore the B63 epitope region or to delete the 179 epitope region, respectively.
Figure 1B:
Figure 1B:

Recombinant, immunogenic polypeptides exhibiting the epitopes of two or more native IBDV, as well as recombinant virus-like particles exhibiting the epitopes of two or more native IBDV and conformational epitopes are effective immunogens for vaccines which can be used to confer protection against a wide variety of IBDV challenge in inoculated poultry. The recombinant polypeptides and virus-like particles are obtained by the expression of chimeric DNA prepared by the insertion, in the VP2 region of a base IBDV, of epitopic determinants for at least a second IBDV. This is most easily done by substitution of the genetic epitopic determinants for the amino acids identities and locations reflected in FIG. 7. Thus, where the epitopic determinant of the second IBDV differs from that of the base IBDV, the genetic epitopic determinant for the differing second IBDV is inserted in place of the genetic epitopic determinant at that location of the base IBDV. An example, combining epitopic determinants from the D78, E/Del 22 and DS326 IBDV into the base GLS IBDV is set forth in FIG. 1. Thus, one DNA sequence can be prepared with genetic epitopic determinants for a plurality of native IBDV. These recombinant plasmids can be inserted into a variety of packaging/expression vector, including baculovirus, fowlpox virus, Herpes virus of turkeys, adenovirus and similar transfection vectors. The vectors can be used to infect conventional expression cells, such as SF9 cells, chicken embryo fibroblast cell lines, chicken embryo kidney cells, vero cells and similar expression vehicles. Methods of transfection, and methods of expression, as well as plasmid insertion into transfection vehicles, are well known and do not constitute an aspect of the invention, per se.

The expression of the chimeric cDNA of the invention generate immunogenic polypeptides which reflect epitopes of a plurality of native IBDV, and the expression of a recombinant VP2, VP4, VP3 cDNA segment, with the VP2 region again comprising genetic epitopic determinants for at least two native IBDV give rise to immunogenic virus-like particles.

The immunogenic polypeptides and virus-like particles can be harvested using conventional techniques (Dobos et al, "J. Virol.", 32:593–605 (1979)). The polypeptides and virus-like particles can be used to prepare vaccines which will confer protection on inoculated poultry, in particular, chickens, and in a preferred embodiment, broiler chickens, protection against challenge from each IBDV bearing an epitope reflected in the plurality of epitopic determinants present in the inoculum. Thus, a single immunogen gives rise to immunity against a variety of IBDV, each IBDV whose genetic epitopic determinant has been incorporated in the chimeric cDNA.

The administration of the vaccines can be effectively done according to well-established procedures. In U.S. Pat. No. 5,064,646, which is incorporated herein by reference, methods are described for the effective inoculation of chicks based on the then novel isolation of GLS IBDV. Similar administration and dosage regimens can be employed herein. Since the polypeptides and virus-like particles lack viral RNA, they are avirulent. The vaccines may therefor be prepared by simple incorporation of the immunogenic polypeptides and virus-like particles in a pharmaceutical carrier, typically a suspension or mixture. Appropriate dosage values are best determined through routine trial and error techniques, given the different antibody titers induced and/or the quantity of different epitopes present which will induce complete cross-immunity to virulent challenge. In general, pharmacologically acceptable carriers such as a phosphate buffered saline, cell culture medium, Marek's virus vaccine diluent oil adjuvants and other adjuvants, etc., can be used. Administration is preferablly done to hens entering egg laying periods which provides induction of antibody which is passively transferred through the egg to the chick to prevent early invention by virulent field strength IBDV. Conversely, the recombinant vaccine may be delivered in a replicating vector at any time in a chicken's life span, preferably at one day of age. Experience has demonstrated that, generally, that the level of protection may be improved by a second inoculation.

This invention may be further understood by reference to the specific examples set forth below.

EXAMPLES

Background Methodology

To determine the molecular basis of antigenic variation in IBDV, the genomic segment A of four IBDV strains: GLS, DS326, Delaware variant E (E/Del) and D78 was cloned and characterized by sequencing. By comparing the deduced amino acid sequences of these strains with other serotype 1 and 2 sequences published previously, the putative amino acid residues involved in the binding with various neutralizing Mabs were identified, and the phylogenetic relationship of IBDV structural proteins was examined.

GLS, DS326 and STC strains of IBDV were propagated in the bursa of specific-pathogen-free chickens (SPAFAS, Inc., Norwich, Conn., U.S.A.). Tissue culture adapted E/Del-22, D78 and OH (serotype 2) strains of IBDV were propagated in primary chicken embryo fibroblast cells derived from 10-day-old embryonated eggs (SPAFAS, Inc.) and purified as described (Snyder et al (1988a) "Avian Dis.", 32:527–534). The Mabs against various strains of IBDV were produced and characterized using protocols previously outlined (Snyder et al (1988a) "Avian Dis.", 32:527–534; Snyder et al (1988b) "Avian Dis.", 32:535–539). Mabs B69 and R63 were prepared against D78 strain, whereas Mabs 8, 10, 57 and 179 were prepared against GLS strain. In addition, a new Mab 67 was prepared which was neutralizing and specific for the E/Del strain. Identification of IBDV antigens by modified antigen capture ELISA (AC-ELISA) was carried out as described (Snyder et al (1992) "Arch. Virol.", 127:89–101).

Various strains of IBDV were characterized by their reactivities with a panel of neutralizing Mabs, as shown in Table 1.

TABLE 1

Antigenic characterization of various IBDV strains by their reactivities with a panel of neutralizaing MAbs

| Virus Strains | Classificiation | Reactivities with MAbs | | | | | | |
|---|---|---|---|---|---|---|---|---|
| | | B69 | R63 | 179 | 8 | 10 | 57 | 67 |
| D78 | Classic | + | + | + | + | + | − | − |
| PBG98 | Classic | − | + | + | + | + | − | − |
| STC | Classic | + | + | + | + | + | − | − |
| 52/70 | Classic | + | + | + | + | − | − | − |
| OH (serotype 2) | Classic | + | + | + | + | − | − | − |
| E/Del | Variant | − | + | + | + | − | − | + |
| GLS | Variant | − | − | + | + | + | + | − |
| DS326 | Variant | − | − | − | + | + | + | − |

All standard serotype 1 viruses reacted with Mabs B69, R63, 179 and 8, except PBG98 (a British vaccine strain, Intervet, U. K.) which did not react with Mab B69. In contrast, all the U.S. variant viruses lack the virus-neutralizing B69 epitope. In addition, GLS and DS326 variants lack an R63 epitope but share a common epitope defined by the Mab 57. Thus, on the basis of the reactivities with various Mabs, these viruses were antigenically grouped as classic, GLS, DS326 and E/Del variants.

Complementary DNA clones, containing the entire coding region of the large RNA segment of various IBDV strains, were prepared using standard cloning procedures and methods previously described (Vakharia et al (1992) "Avian Dis.", 36:736–742; Vakharia et al (1993) "J. Gen. Virol.", 74:1201–1206). The complete nucleotide sequence of these cDNA clones was determined by the dideoxy method using a Sequenase DNA sequencing kit (U.S. Biochem. Corp., Columbus, Ohio). DNA sequences and deduced amino acid sequences were analyzed by a PC/GENE software package (Intelligenetics, Inc.). these are reflected in FIGS. 5 and 6. The nucleotide sequence data of the GLS strain has been deposited with GenBank Data Libraries and has been assigned an accession number M97346.

Figure 3A:
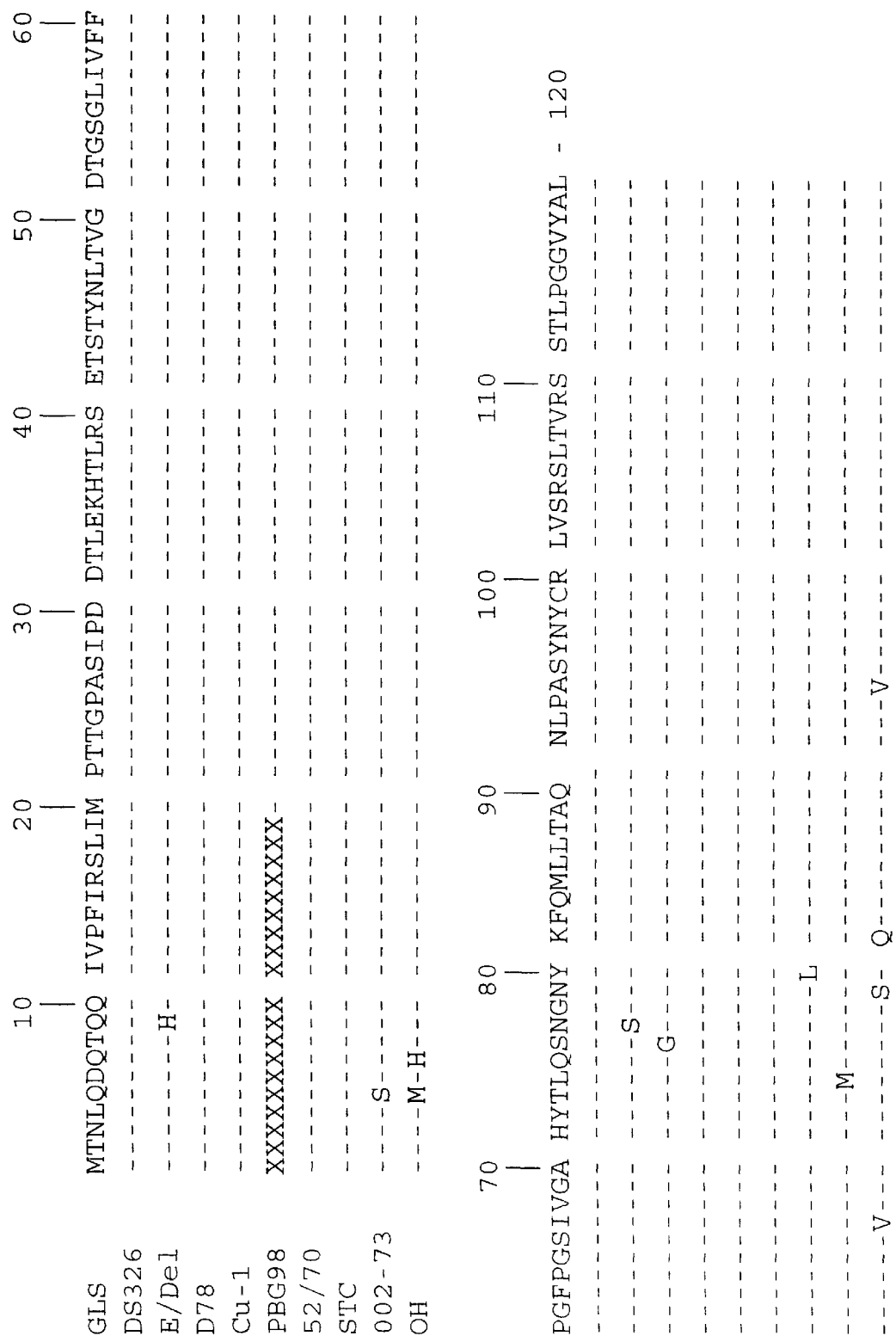
FIG. 3 is a comparison of the deduced amino acid sequences of the structural proteins (VP2, VP3 and VP4) of ten IBDV strains (SEQ ID NO:1–10). Dashes (-) indicate amino acid identity and crosses (x) denote a region where the sequence was not determined. Filled bar (■) indicates a gap in the sequence and vertical arrowheads (↓) mark the possible cleavage sites of VP2/VP4 and VP4/VP3. The two hydrophilic peaks in the variable region are overlined.
Figure 3F:
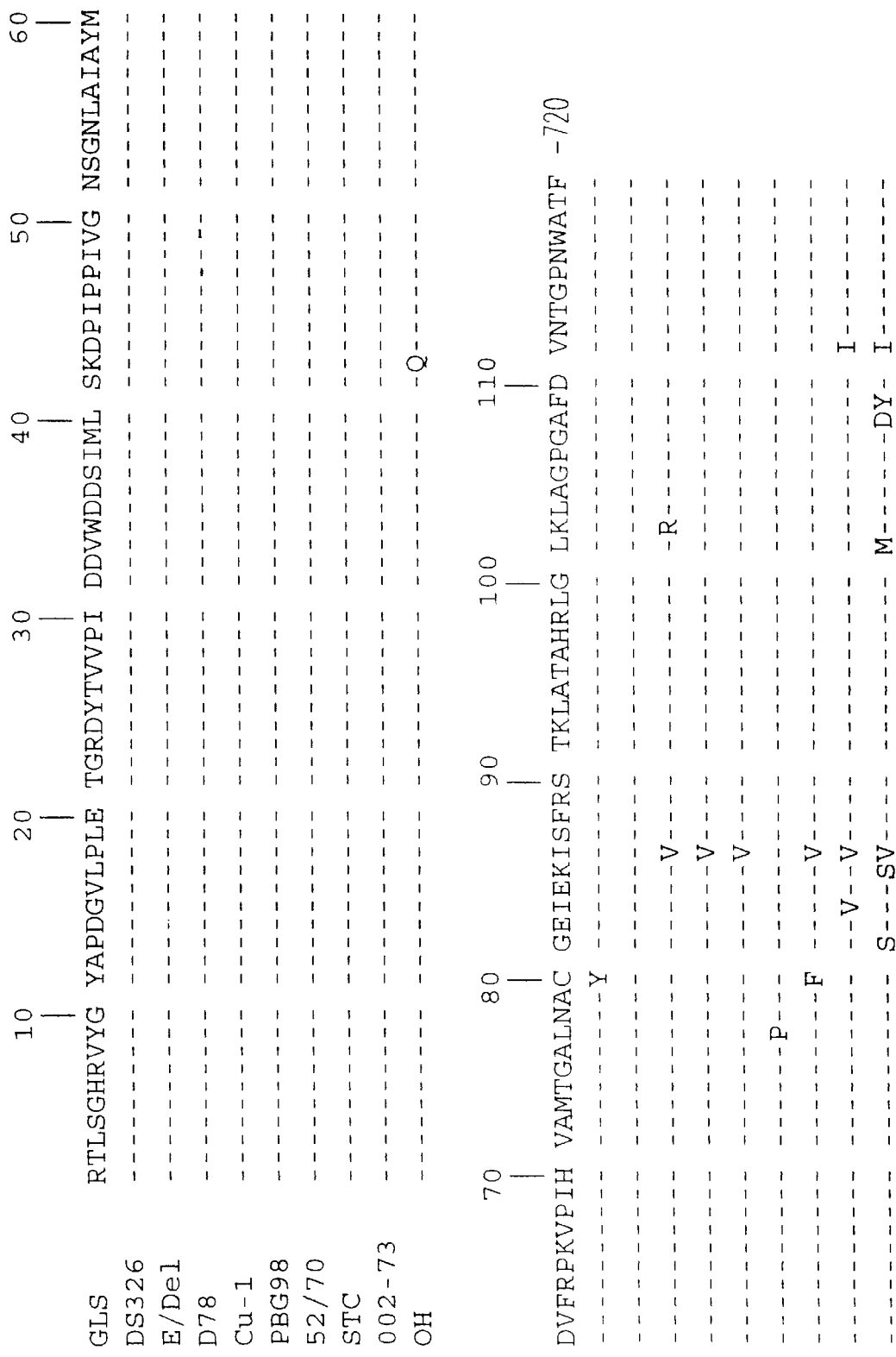
Figure 3G:
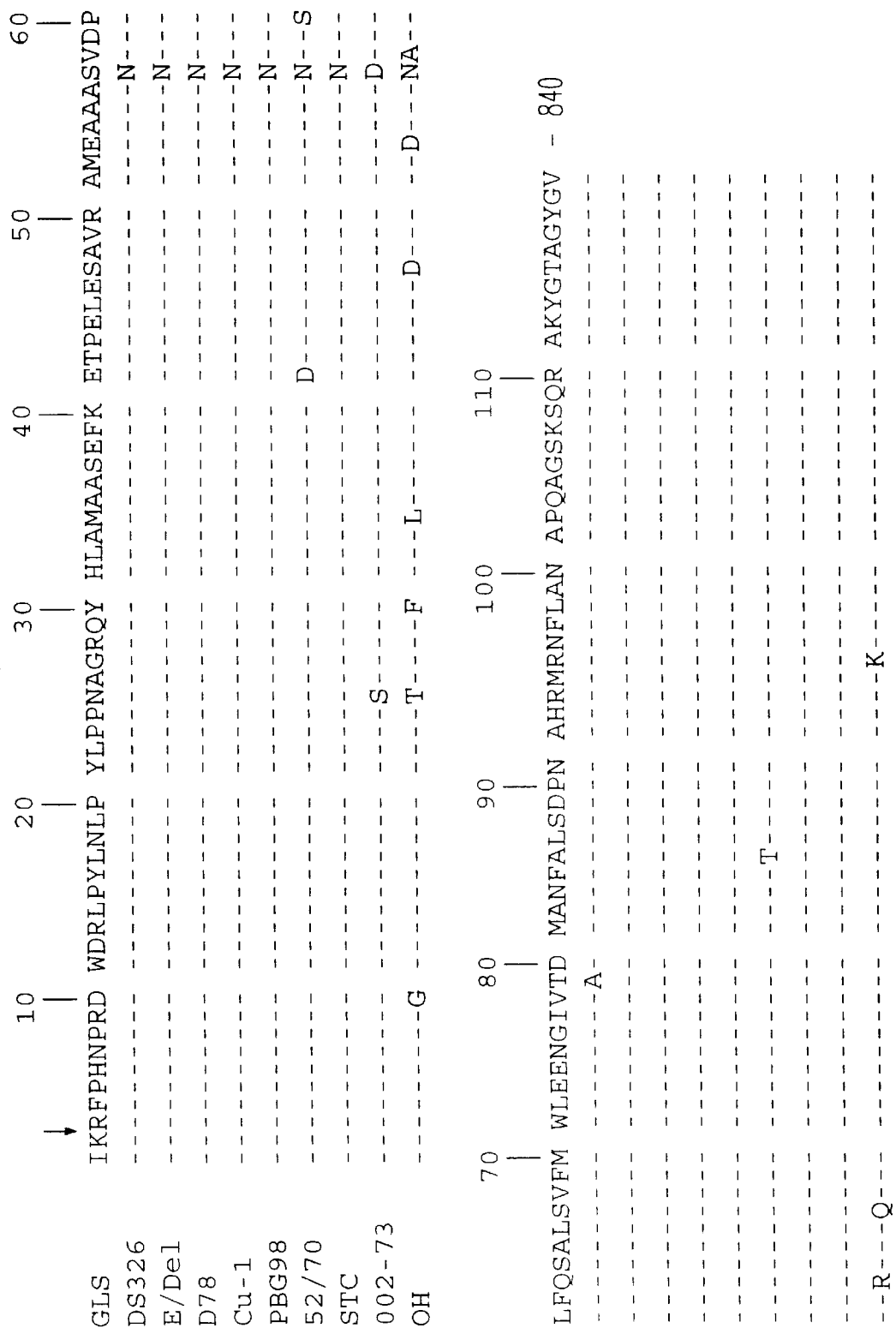

Comparisons of the nucleotide sequence of GLS strain (3230 bp long) with eight serotype 1 and one serotype 2 IBDV strains exhibit ≧92% and ≧82% sequence homology, respectively; indicating that these viruses are closely related. It is interesting to find that there are only six to nine base substitutions between D78, PBG98, and Cu1 strains which corresponds to a difference of about 0.2% to 0.3% (results not shown). FIG. 3 and Table 2 show a comparison of the deduced amino acid sequences and percent homology of the large ORF of segment A of the ten IBDV strains, including four IBDV strains used in this study.

TABLE 2

Percent amino acid sequence homology of large ORF of segment A of ten IBDV strains

| Strain | GLS | DS326 | E/Del | D78 | Cu-1 | PBG98 | 52/70 | STC | 002-73 | OH |
|---|---|---|---|---|---|---|---|---|---|---|
| GLS | | | | | | | | | | |
| DS326 | 98.7 | | | | | | | | | |
| E/Del | 98.4 | 98.3 | | | | | | | | |
| D78 | 98.5 | 98.1 | 97.9 | | | | | | | |
| Cu-1 | 98.6 | 98.2 | 98.0 | 99.6 | | | | | | |
| PBG98 | 98.5 | 98.1 | 97.9 | 99.5 | 99.5 | | | | | |
| 52/70 | 98.1 | 98.1 | 97.9 | 98.4 | 98.5 | 98.3 | | | | |
| STC | 97.7 | 98.0 | 97.5 | 98.4 | 98.5 | 98.3 | 98.3 | | | |
| 002-73 | 97.0 | 97.1 | 96.7 | 97.6 | 97.7 | 97.6 | 97.3 | 97.4 | | |
| OH | 90.0 | 90.0 | 89.7 | 90.2 | 90.3 | 90.2 | 89.8 | 90.3 | 90.1 | |

These comparisons show that the proteins are highly conserved. The degree of difference in the amino acid sequence ranges from 0.4% for the D78 versus Cu-1 comparison and 10.3% for the serotype 1 (E/Del) versus serotype 2 (OH) comparison (Table 2).

In FIG. 3, alignments of the deduced amino acid sequences of the large ORF (1012 residues) of ten IBDV strains (including four used in this study) show that most of the amino acid changes occur in the central variable region between residues 213 and 332 of VP2 protein, as shown earlier by Bayliss et al (1990) "J. Gen. Virol.", 71:1303–1312. It is interesting to note that all the U.S. variants (GLS, DS326 and E/Del) differ from the other strains in the two hydrophilic regions which are overlined in FIG. 3 (residues 212 to 223 and residues 314 to 324). These two hydrophilic regions have been shown to be important in the binding of neutralizing Mabs and hence may be involved in the formation of a virus-neutralizing epitope (Heine et al (1991) "J. Gen. Virol.", 22:1835–1843). Recently, we demonstrated that the conformation dependent Mabs B69, R63, 8, 179, 10, and 57 (see Table 2) immunoprecipitate VP2 protein (Snyder et al (1992) "Arch. Virol.", 127:89–101). In addition, E/Del specific Mab 67 also binds to VP2 protein. Therefore, to identify the amino acids involved in the formation of virus-neutralizing epitopes, and hence the antigenic variation, we compared the amino acid sequences of VP2 protein of classic and variant viruses.

Comparison of the D78 sequence with the PBG98 sequence shows only four amino acid substitutions at positions 76, 249, 280 and 326. However, STC and 52/70 strains also sequence at the D78 sequence at positions 76, 280 and 326 but these viruses do bind to Mab B69. This implies that Gln at position 249 (Gln249) may be involved in the binding with Mab B69. It should be noted that all U.S. variant viruses have a Gln→Lys substitution at this position and hence escape the binding with neutralizing Mab B69. Similarly, comparison of the GLS sequence with the DS326 sequence in the variable region shows six amino acid substitutions at positions 222, 253, 269, 274, 311 and 320. However, other strains of IBDV that do bind to Mab 179 have amino acid substitutions at positions 222, 253, 269 and 274 that are conservative in nature. Therefore, this suggests that Glu311 and Gln320 may be involved in the binding with Mab 179. Again, comparison of GLS and DS326 sequences with all other IBDV sequences shows a unique Ala→Glu substitution at position 321, suggesting the contribution of this residue in the binding with Mab 57. Since Mab 57 does not compete with Mab R63, it is conceivable that Ala321 may contribute to the binding with Mab R63. Similarly, comparison of E/Del sequence with other sequences shows five unique substitutions at positions 213, 286, 309, 318 and 323. However, comparison of this E/Del sequence (from tissue culture derived virus) with previously published VP2 A/Del and E/Del sequences (bursa derived virus) suggests the involvement of Ile286, Asp318 and Glu323 in the binding with Mab 67 since residues at positions 213 and 309 are not substituted in A/Del and E/Del sequences, respectively (Heine et al (1991) "J. Gen. Virol.", 22:1835–1843; Lana et al (1992) "Virus Genes", 6:247–259; Vakharia et al (1992) "Avian Dis.", 36:736–742).

Comparisons of the amino acid sequence also show a striking difference between serotype 1 and serotype 2 sequences. In serotype 2 OH strain, there is an insertion of an amino acid residue at position 249 (serine) and a deletion of a residue at position 680. Previously, it has been shown that serotype 2 viruses are naturally avirulent and do not cause any pathological lesions in chickens (Ismail et al (1988) "Avian Dis.", 32:757–759). Thus, these subtle changes in the structural proteins of serotype 2 OH strain may play an important role in the pathogenicity of the virus. Moreover, it has been hypothesized that an amino acid sequence motif, S-W-S-A-S-G-S, (residues 326 to 332 SEQ ID NO:15) is conserved only in virulent strains and could be involved in virulence (Heine et al (1991) "J. Gen. Virol.", 22:1835–1843). This sequence motif was also conserved in various pathogenic strains of IBDV isolated in Japan (Lin et al (1993) "Avian Dis.", 37:315–323). Comparison of the amino acid sequences in this heptapeptide region reveals that nonpathogenic serotype 2 OH strain has three substitutions, whereas mildly pathogenic strains of serotype 1 (D78, Cu-1, PBG98 and 002-73) have one or two substitutions in this region. Moreover, comparison of the hydrophilicity plots of the variable region (amino acids 213 to 332) of variant serotype 1 strains and serotype 2 OH strain indicates a drastic reduction in the second hydrophilic peak region (amino acid residues 314 to 324) for serotype 2 (results not shown). Since most of the amino acid residues causing antigenic variation reside in this region, these residues may play an important role in the formation of virus-neutralizing epitopes, as well as serotype specificity.

Figure 4:
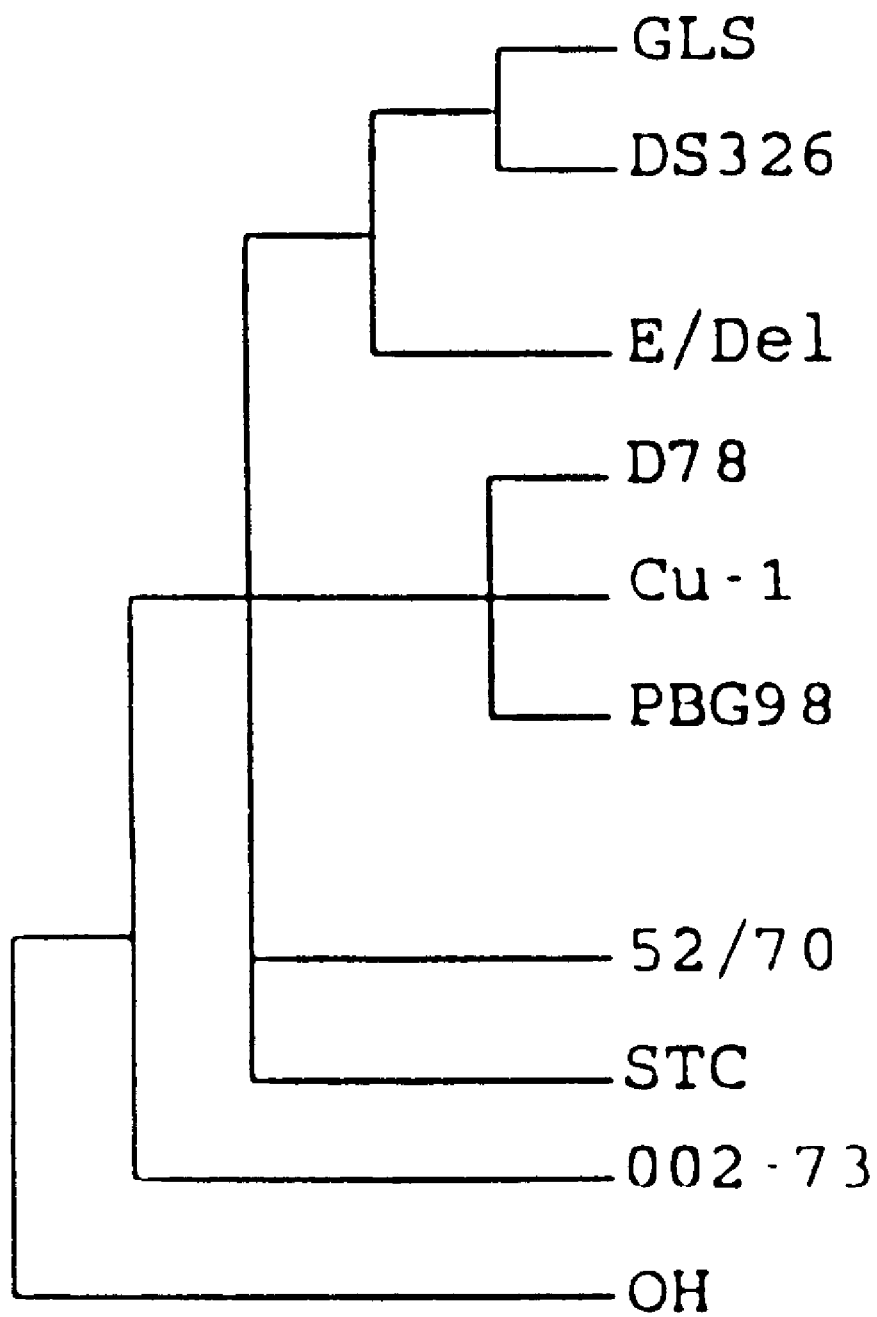
FIG. 4 is a phylogenetic tree for the IBDV structural proteins using the PAUP (phylogenetic analysis using parsimony) version 3.0 program (Illinois Natural History Survey, Champaign, Ill.).

To evaluate the antigenic relatedness of structural proteins of various IBDV strains, a phylogenetic tree was constructed, based on the large ORF sequences of ten IBDV strains, including the U.S. variant strains examined in this study (FIG. 4). Three distinguishable lineages were formed. The first one, which is most distant from the others, is serotype 2 OH strain, and the second one is the geographically distant Australian serotype 1 strain (002-73). The third lineage consists of four distinct groups. The first and second group include highly pathogenic strains, namely, standard challenge (STC) strain from U.S. and the British field strain (52/70). The third group comprises all the European strains: the vaccine strains D78 (Holland), PBG98 (U.K.), and mildly pathogenic strain Cu-1 (Germany). The fourth group consists of the U.S. variant strains in which E/Del forms a different subgroup. The groups formed by the phylogenetic analysis correlate very well with the Mabs reactivity patterns (see Table 1). As shown in FIG. 4, all the U.S. variant viruses which lack the B69 epitope form a distinct group, whereas all the classic viruses containing a B69 epitope form another group (except PBG98). In addition, closely related GLS and DS326 strains containing a common Mab 57 epitope and lacking an R63 epitope could be separated from the other variant E/Del strain.

Based on this information, a recombinant vaccine was constructed as follows:

Construction of recombinant baculovirus clones containing chimeric IBDV genes

A recombinant baculovirus which expresses a chimeric VP2, VP3 and VP4 structural proteins of the GLS strain was constructed and assessed. The recombinant baculovirus expressed a chimeric VP2 protein incorporating all Mab defined GLS neutralization sites, as well as one neutralization site (B69) which is specific for Classic strains of IBDV in the form of a VP2-VP4-VP3 segment.

Complementary DNA clones, containing the entire coding region of the large RNA segment of the GLS and D78 IBDV strains, were prepared using standard cloning procedures and methods previously described (Vakharia et al (1992) "Avian Dis.", 36:736–742; Vakharia et al (1993) "J. Gen. Virol.", 74:1201–1206). To insert the gene sequence encoding the B69 epitope of the D78 IBDV strain, plasmid pB69GLS was constructed as follows (see FIG. 1). Full-length cDNA clones of D78 and GLS (plasmids pD78 and pGLS-5) were digested with NdeI-NarI and NarI-SpeI enzymes to release a NdeI-NarI (0.26 kb) and a NarI-SpeI (0.28 kb) fragments, respectively. These two fragments were then ligated into the NdeI-SpeI cut plasmid pGLS-5 to obtain a chimeric plasmid pB69GLS. As a result of this insertion, three amino acids were substituted in the GLS VP2 protein. These substitutions were at positions 222 (Thr-Pro), 249 (Lys-Gln) and 254 (Ser-Gly) in the variable region of the VP2 protein (Vakharia et al (1992) "Avian Dis.", 36:736–742). To insert the chimeric IBDV structural genes in the Baculovirus genome, plasmid pB69GLS was completely digested with BstEII enzyme and partially with the BamHI enzyme, combined with the NheI-BstEII fragment (derived from plasmid pGLSBacI, see Vakharia et al (1993) "J. Gen. Virol.", 74:1201–1206) and then ligated to the NheI-BamHI cut transfer vector pBlueBacII (Invitrogen Corp., San Diego, Calif.). Finally, recombinant baculovirus I-7 was obtained using previously described procedures (Vakharia et al (1993) "J. Gen. Virol.", 74:1201–1206). See Table 3.

Preparation of an inoculum for immunization

*Spodoptera frugiperda* SF9 cells, infected at a multiplicity of 5 PFU per cell with the I-7 recombinant baculovirus, were propagated as suspension cultures in one liter flasks containing Hink's TNM-FH medium (JHR Biosciences, Lenxa, Kans.) supplemented with 10% fetal calf serum at 28° C. for 3 to 4 days. The infected cells were recovered by low speed centrifugation, washed two times with PBS, and resuspended in a minimum volume of PBS. The cell slurry was sonicated on and ice bath three times for 1 min, with 2 min intervals and clarified by low speed centrifugation. An aliquot of each cell lysate was tested with anti-IBDV Mabs by AC-ELISA to estimate the antigenic mass present (Snyder et al (1998b) "Avian Dis.", 32:535–539). Preparations having the highest antigenic mass were pooled and comparatively titrated in AC-ELISA against the V-IBDV-7-1 recombinant baculovirus IBDV vaccine used in a previous study (Vakharia et al (1993) "J. Gen. Virol.", 74:1201–1206). The antigenic mass of the I-7 recombinant preparation, as determined by AC-ELISA with group specific neutralizing Mab 8, was adjusted by dilution to be the same as the V-IBDV-7-1 vaccine, and then it was emulsified with an equal volume of Freund's incomplete adjuvant and used for inoculation.

Viruses

The challenge viruses: Classic strains IM and STC, and variant strains E/Del and GLS-5 were obtained from previously acknowledged sources (Snyder et al (1988a) "Avian Dis.", 32:527–534; Snyder et al (1992) "Arch. Virol.", 127:89–101). After intraocular instillation, challenge viruses were titrated in the bursae of specific-pathogen-free (SPF) chickens (SPAFAS, Inc., Storrs, Conn.). For strains STC, E/Del and GLS-5, a 100 chick infective fifty percent dose (100 $CID_{50}$) was determined based on bursa to body weight measurements. One hundred lethal doses (100 LD) of the IM strain were calculated based on mortality at 8 days post-inoculation (PI).

Chicken inoculations and IBDV challenge

White leghorn SPF chickens were hatched and reared in HEPA filtered isolation units (Monair Anderson, Peachtree City, Ga.). Eight-week old chickens were prebled, individually wing banded, divided among 10 groups of 15 chicks each and treated as follows. Chickens of groups I–V received no inoculations and served as either negative or positive challenge controls. Chickens of group V–X were inoculated intramuscularly with 0.5 ml of the 1-7 inoculum prepared above from recombinant Baculovirus infected cell lysates. At 3 weeks PI, all chickens were bled and chickens of groups II–IX were challenged with the appropriate IBDV challenge strain by ocular instillation. Four days post-challenge, 5 chickens from each group were humanely sacrificed and their cloacal bursa were removed. Each bursa was processed and subsequently evaluated for the presence of IBDV antigen by AC-ELISA as described (Snyder et al (1998b) "Avian Dis.", 32:535–539). In addition, chickens in the IM challenged groups were scored as dead, and humanely sacrificed when they became obviously moribund due to IM challenge. Eight days post-infection, the remaining chickens in all groups were sacrificed and weighed. The bursa of Fabricius from each chicken was carefully excised and also weighed. Bursa weight to body weight ratio was calculated for each chicken as described by Lucio and Hitchner (Lucio et al (1979) "Avian Dis.", 23:466–478). Any value for individually challenged chickens falling plus or minus two standard deviation units from the mean of the corresponding control group was scored as a positive indicator of IBDV infection. Opened bursae were fixed by immersion in 10% neutral buffered formalin. Transverse portions of bursae were processed through graded alcohols and xylene, embedded into paraffin, sectioned, stained with hematoxylin-eosin, and examined with a light microscope. Protection against challenge was defined as the absence of any IBDV-induced lesions in the bursa of Fabricius.

Serological evaluation

The Classic D78 strain, as well as the cell culture adapted variant GLS strain of IBDV were grown in primary chicken embryo fibroblast cells and used in virus neutralization (VN) tests to test sera from the vaccine trial essentially as described (Snyder et al (1988a) "Avian Dis.", 32:527–534). Serum from the trials was also tested for the presence of anti-IBDV antibody using a commercially available IBDV antibody ELISA kit (Kirkegaard and Perry, Gaithersburg, Md.).

Evaluation of vaccines and challenge viruses

The antigenic content of the I-7 GLS chimeric IBDV vaccine was assessed in AC-ELISA with a panel of VP2 and VP3 specific Mabs. The relative antigenic mass of each epitope expressed in the I-7 vaccine was compared to previously tested lots of Baculovirus expressed unmodified GLS subunit vaccines (Vakharia et al (1993) "J. Gen. Virol.", 74:1201–1206). The status of each Mab defined epitope on the I-7 chimeric vaccine was also compared to the status of those Mab defined epitopes occurring on wild type IBDV challenge viruses used to evaluate the efficacy of the I-7 vaccine. Table 3 shows that antigenic mass levels at the 8, 57, and B29 epitopes for the current I-7 chimeric vaccine were similar to a recently tested unmodified V-IBDV-7-1 GLS subunit vaccine, but approximately 4-fold higher than the original unmodified V-IBDV-7 vaccine.

A major difference in the unmodified and chimeric vaccines was the appearance of the Classic B69 epitope in the chimeric GLS product. The level of the B69 epitope was arbitrarily set at 9 since no comparisons could be made to the unmodified GLS subunit vaccines. By comparing the status of Mab defined epitopes on the challenge viruses with the unmodified and chimeric GLS subunit vaccines (Table 3), it could be seen that while the chimeric product had expressed the B69 epitope found on the Classic STC and IM challenge viruses, that it also retained all of the homologous GLS epitopes.

Active-cross protection

Table 4 shows the results of a cross-protection trial and serological results obtained prior to challenge.

TABLE 3

Comparative levels of IBDV, VP2, and VP3 monoclonal antibody (Mab) defined epitopes on recombinant baculovirus expressing IBDV proteins and status of Mab defined epitopes on challenge viruses used.

| Vaccine | Relative level of Mab epitope[A] | | | | | Challenge Virus | Status of Mab epitope[B] | | | | |
|---|---|---|---|---|---|---|---|---|---|---|---|
| | 8 | 57 | B69 | 67 | E29 | | 8[C] | 57[C] | B69[C] | 67[C] | E29[D] |
| V-IBD-7[E] | 1 | 1 | 0 | 0 | 1 | GLS | + | + | – | – | + |
| V-IBD-7-1[E] | 3 | 3 | 0 | 0 | 2 | STC | + | – | + | – | + |
| I-7[F] | 3 | 3 | 9 | 0 | 2 | LM | + | – | + | – | + |
| | | | | | | E/Del | + | – | – | + | + |

[A]The relative level of each Mab epitope was determined by AC-ELISA, and the level of each Mab epitope was set to 1 for the V-IBD-7 vaccine previously used (15). Maximum level is 9. Each 1.0 increment represents approximately twice the amount of the epitope present in the original V-IBD-7 vaccine. The V-IBD-7-1 vaccine was also previously reported (16).
[B]The status of Mab epitopes was determined by AC-ELISA and is presented as present (+) or absent (–).
[C]Neutralizing Mab epitope resides on VP2 of IBDV.
[D]Non-neutralizing Mab epitope resides on VP3 of IBDV.
[E]Recombinant baculovirus vaccines incorporating unmodified large segment A GLS proteins.
[F]Current recombinant baculovirus vaccine incorporating modified chimeric large segment A GLS proteins.

TABLE 4

Active cross-protection induced 2-weeks post immunization with baculovirus expressed chimerle I-7 IBDV antigens and associate prechallenge serolgy.

| Group No. | Vaccination[A] | Challenge[B] | Number Protected | | | Mean VN Titer Log | | Alena ELISA |
|---|---|---|---|---|---|---|---|---|
| | | | AC-ELISA[C] | Msto[D] | DBWR[E] | D78 | GLS | |
| I | None | None | NA | NA | NA | ≦4 | ≦4 | 0 |
| II | None | STC | 0/5 | 0/10 | 0/10 | ≦4 | ≦4 | 0 |
| III | None | IM | 0/5 | 0/5[E] | 5/5[E] | ≦4 | ≦4 | 0 |
| IV | None | E/Del | 0/5 | 0/10 | 0/10 | ≦4 | ≦4 | 0 |
| V | None | GLS-5 | 0/5 | 0/10 | 0/10 | ≦4 | ≦4 | 0 |
| VI | 1–7 | STC | 5/5 | 10/10 | 10/10 | 10.7 (1.8)[F] | 10.4(1.4)[F] | 1235 (312)[F] |
| VII | 1–7 | IM | 5/5 | 10/10 | 10/10 | 10.0 (1.4) | 10.4 (2.1) | 1201 (791) |
| VIII | 1–7 | E/Del | 5/5 | 10/10 | 10/10 | 11.4 (1.2) | 10.6 (1.9) | 1089 (409) |
| IX | 1–7 | GLS-5 | 5/5 | 10/10 | 10/10 | 11.0 (1.5) | 12.0 (2.0) | 1220 (339) |
| X | 1–7 | None | 5/5 | NA | NA | 9.9 (1.4) | 9.3 (1.4) | 1140 (473) |

[A]Vaccination was given at 8-weeks of age.
[B]Challenge virus was given by intraocular instillation 3-weeks post immunization or at 11-weeks of age for controls.
[C]Protection was determined by AC-ELISA examination of ½ of each group 4-days post-challenge.
[D]Protection was determined histologically and by bursa to body weight ratios at 8-days.
[E]Five chickens were scored as dead due to IM challenge prior to 8-days post-challenge.
[F]One standard deviation.

Groups II–V served as challenge controls and as indicated by AC-ELISA, bursa to body weight and histological assessments, all non-vaccinated chickens were fully susceptible to virulent IBDV challenge with all strains used. The IM challenge produced lethal disease in one-third of the control group chicks. In contrast, 8-week old chickens comprising Groups VI–IX were vaccinated once with the GLS chimeric vaccine, and 3-weeks PI all vaccinated chickens were completely protected from challenge by all challenge viruses, including lethal disease produced in controls by the IM strain. Serologically, titers from reciprocal-cross VN tests conducted on prechallenge sera with the D78 and GLS tissue culture viruses were essentially within 2-fold of one another. Mean ELISA titers were relatively low, but were also uniform between the vaccinated groups.

Characterization of vaccines

In initial studies with Baculovirus expressed subunit GLS vaccines, after administration of two doses, the V-IBDV-7 GLS vaccine (Table 3) could only induce active antibody levels capable of providing 79% protection against homologous GLS challenge (Vakharia et al (1993) "J. Gen. Virol.", 74:1201–1206). In a subsequent study, the antigenic mass of the original V-IBDV-7 vaccine was increased approximately 4-fold (calculated at the group specific Mab 8 site) and initiated one dose and two dose vaccination cross-challenge trials with the unmodified GLS subunit vaccine designated as V-IBDV-7-1 (Table 3). In those trials, two doses of the vaccine yielded complete cross-protection against virulent STC, E/DEL and GLS challenge. However, in the one vaccine dose trial, while complete protection was attained against challenge with variant E/DEL and GLS viruses, only 44% protection was achieved against the more distantly related Classic STC virus. Those studies could mean that simply by increasing the antigenic mass and/or doses of the vaccine that better cross-protection could be obtained. However, it was also evident in the absence of homologous vaccination that lower levels of antibody, induced by one dose of the GLS V-IBDV-7-1 subunit vaccine, were not sufficiently cross-protective against Classic IBDV challenge. This could mean that in even lower levels of antibody, such as in cases of waning maternal antibody, that cross-protection would likely be even more reduced. Indeed, although not challenged with the STC virus, in some passive maternal antibody studies conducted using another dosage of the V-1BDV-7 vaccine, while homologous GLS protection was afforded, progeny of vaccinated hens were only 57% protected against a more closely related E/DEL challenge.

In a single-dose vaccination cross-challenge trial, the chimeric GLS I-7 vaccine, which incorporated the Classic B69 neutralization epitope, was evaluated. In order to make the current trial comparable to previous trials, the I-7 vaccine was formulated such that by AC-ELISA the relative antigenic mass of the I-7 chimeric subunit vaccine was nearly identical to the unmodified V-IBDV-7-1 vaccine previously used (Table 3). Table 4 shows the results of the cross-challenge after a single dose of the I-7 vaccine was administered. Results were similar to those obtained with the unmodified V-IBDV-7-1 vaccine previously used in that protection against the GLS and E/DEL strains was complete. However, the I-7 vaccine yielded complete protection against pathogenic and lethal challenge by the Classic STC and IM strains respectively. Since the antigenic mass of the GLS and group common epitopes on V-IBDV-7 and I-7 vaccines were carefully equilibrated and equal, it is reasonable to conclude that the comparative increase in efficacy of the I-7 vaccine against challenge with Classic IBDV strains was due solely to the incorporation of the Classic IBDV B69 neutralization epitope in the GLS VP2 protein sequence.

Virus-Like Particles

As noted above, the recombinant cDNA and immunogens expressed thereby, of this invention may be confined to the VP2 immunogenic region. In other words, it may be sufficient to prepare a cDNA clone encoding epitopic determinants for a base IBDV, e.g., GLS, as well as a second IBDV epitopic determinant, such as D78. Other epitopic determinants, all in the VP2 epitopic determinant region may be incorporated, cloned and expressed as discussed above.

Figure 2A:
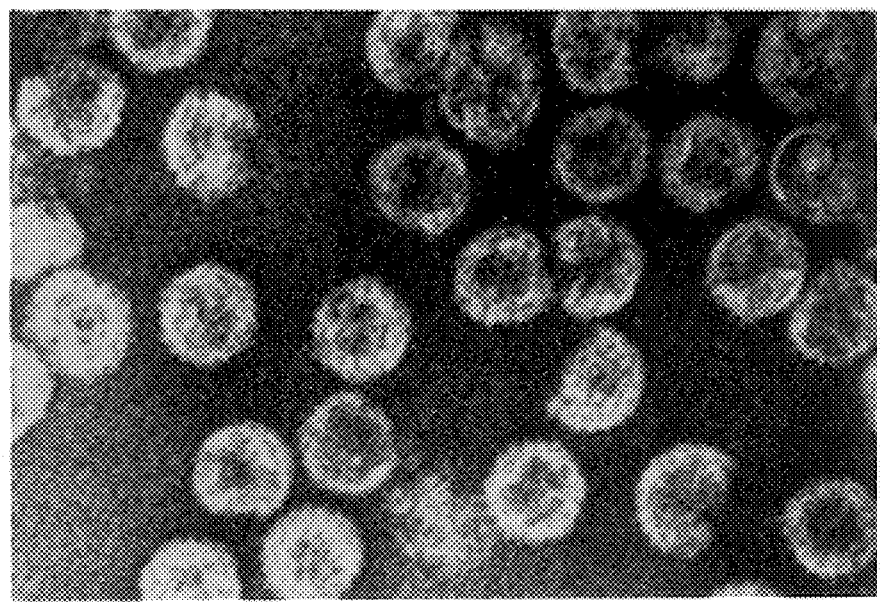
FIG. 2 is electron micrographs of IBDV virus-like particles (⊢⊣ =100 nm). A. Actual empty particles (without RNA) from purified virus. B. Virus-like particles (empty capsids) derived from a recombinant baculovirus expressing the large genome segment of IBDV in insect cells
Figure 2B:
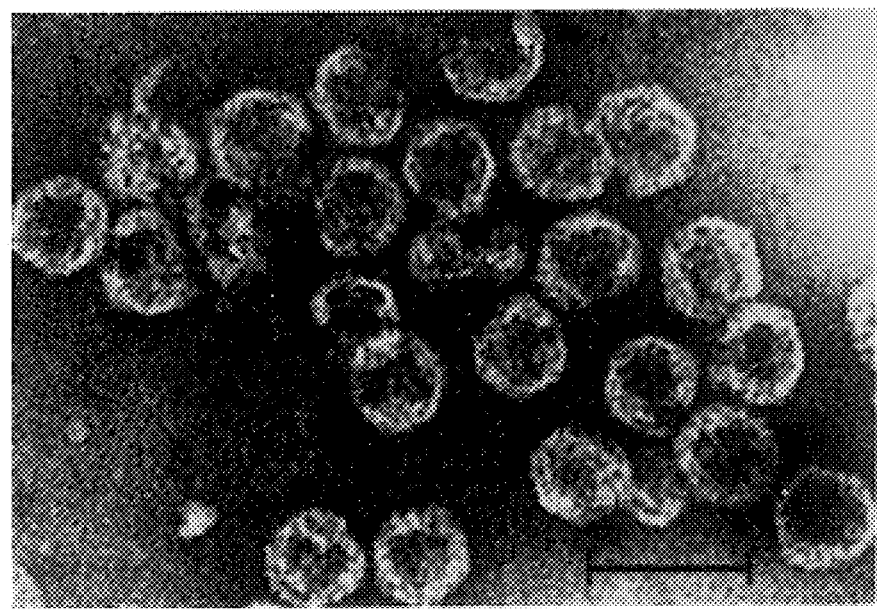

As reflected in FIG. 2, virus-like particles are generated by the expression of DNA encoding the VP2-VP4-VP3 structural protein sequences. These virus-like particle immunogens can be separated from the corresponding VP2 only immunogens, both in terms of monoclonal antibody and by conventional separation measures, such as electrophoresis and chromatography. The difference in reactivity with monoclonal antibody strongly indicates, however, that epitopes present in the VP2-VP4-VP3 structural protein sequence-induced virus-like particles are present that are not present in immunogens expressed by the identical VP2 only region. These epitopes are "both linear and conformational" epitopes. Conformational epitopes differ from linear epitopes and are reflected in the conformation, not only in amino acid sequence of the actual virus. As a result, inoculation of poultry with a recombinant virus-like particle may provide even superior protection against field challenge from IBDV than inoculation with the immunogens of the VP2 region only. This is due to the spontaneous assembly of all the structural elements of the virus.

Applicants have discovered that the expression of the VP2 region as part of the VP2-VP4-VP3 structural protein single segment generates virus-like particles such as those of FIG. 2. These particles have been demonstrated to react with antibodies which do not react similarly with the identical recombinant VP2 immunogen. Thus, the virus-like particles may give rise to higher antibody titers, and/or subtly different (broader) protection when a poultry host is inoculated therewith.

The invention herein therefore embraces (1) recombinant VP2 immunogens comprising epitopic determinants of at least two different IBDV strains and (2) virus-like particles of VP2-VP4-VP3 segments wherein the VP2 region again comprises epitopic determinants of at least two different IBDV strain, as well as the nucleotide sequences encoding both 1 and 2, and vaccines embracing the same.

Recombinant Epitopic Determinant Combinations

As reflected in the examples set forth above, genetic epitopic determinants for an IBDV strain can be inserted in the VP2 region of a different, base IBDV genetic sequence, and subsequently used to express an immunogen exhibiting epitopes for both IBDV. Indeed, the examples above demonstrate the combination of at least three different IBDV epitopic determinants. More can be combined. The resulting vaccine includes an active agent, the expressed immunogen, which provides challenge protection against a broad spectrum of IBDV, rather than prior art virus-based vaccines which give protection against a single strain, or a single family of strains.

FIG. 7 reflects the amino acid identities for the epitopic determinant region for seven different IBDV. These are not intended to be limiting, but are representative. Desirable recombinant immunogens, both VP2 only and virus-like particle VP2-VP4-VP3 immunogens are made by substituting the genetic epitopic determinants for the varying amino acids at the identified locations in FIG. 7 (locations not identified are conserved throughout the IBDV strains). This induces the expression of the inventive immunogens.

Clearly, the possible combinations, while large in number, are limited, and may be investigated with routine skill. Representative combinations will tend to reflect combinations of epitopic determinants for dominant IBDV.

A E/Del/GLS recombinant may include changes in the E/Del epitopic determinant region at position 213, Asn-Asp, 253 Gln-His and 169 Thr Ser.

A DS326/D78 recombinant may include the amino acid, and corresponding nucleotide substitutions at 76Ser-Gly, 249 Lys-Gln, 253 Gln-His and 270 Ala-Thr substitutions.

Obviously, a wide variety of combinations are possible and will occur to those of skill in the art. The epitopic determinant region, roughly including the region from amino acid 5–433 of the VP2 region, thus constitutes a recombinant "cassette" which may be tailored by site-specific mutagenesis to achieve amino acid insertion and/or deletion to provide desired recombinant cDNA clones, polypeptides, virus-like particles and vaccines with improved protection against a wide variety of IBDV.

Lethal IBDV, Monoclonal Antibody and Vaccine therefore

As noted, typically, IBDV infection creates an immunosuppressive condition, and is reflected in lesions in the bursa of Fabricius. This is typical of IBDV countered in the United States. There exist, however, lethal IBDV, that is, IBDV infections which results in chicken mortality directly as a result of IBDV infection. While vaccines have been developed on the basis of isolation of these IBDV, the resulting vaccines are "hot", that is, they themselves create or induce an immunosuppressive condition, and the inoculated chick must be bolstered with antibodies to other infectious agents. This method of protection is so undesirable as to have been discontinued in most commercial poultry houses in Europe. No adequate safe vaccine against the lethal IBDV is currently available.

The inventors have developed a monoclonal antibody, Mab 21, deposited under Budapest Treaty conditions at the American Type Culture Collection, Deposit Accession No. ATCC HB 11566. This monoclonal antibody is specific and neutralizing for lethal IBDV strains. The specificity is reflected in Table 5, which confirms that unlike other monoclonal antibody, Mab 21 is specific for an epitope exhibited only by IBDV strains having lethal potential.

TABLE 5

| Source | IBDV Strain | Comment | E29 | 8 | 179 | 10 | 63 | 69 | 28 | 67 | 57 | 58 |
|---|---|---|---|---|---|---|---|---|---|---|---|---|
| | Lethal Potential | | | | | | | | | | | |
| | IM+ | + | + | + | + | + | + | + | + | − | − | − |
| Sharma | IM | + | + | + | + | + | + | + | + | − | − | − |
| USDA | STC | + | + | + | + | + | + | + | + | − | − | − |
| Spafas | 2512 (Winterfield) | + | + | + | + | + | + | + | + | − | − | − |
| Edgar | Edgar | (vaccine hot) | + | + | + | + | + | + | + | − | − | − |
| | Pathogenic Virus | | | | | | | | | | | |
| Sterwin | Bursa Vac | (vaccine hot) | + | + | + | + | + | + | + | − | − | − |
| | Vaccine Virus | | | | | | | | | | | |
| ASL | Univax-BD | (ST 14) | + | + | + | + | + | + | − | − | − | − |
| Select | Burrell Disease Vaccine | (Luk) | + | + | + | + | + | + | − | − | − | − |
| Select | | (STD + VAR) | + | + | + | + | + | + | − | − | − | − |
| Key Vet | Bio-Burs I | (D78) | + | + | + | + | + | + | − | − | − | − |
| Key Vet | Bio-Burs W | (Luk) | + | + | + | + | + | + | − | − | − | − |
| MBL | Maryland | (Master seed) | + | + | + | + | + | + | − | − | − | − |
| Sterwin | BVM | (Baxendale) | + | + | + | + | + | +/− | − | − | − | − |
| Sterwin | 1041-E | | + | + | + | + | + | +/− | − | − | − | − |
| Lukert | BVM | (Lab Strain) | + | + | + | + | + | +/− | − | − | − | − |
| CEVA | Bursa Blend | (2512) | + | + | + | + | + | + | − | − | − | − |
| InterVet | D78 | | + | + | + | + | + | + | − | − | − | − |
| InterVet | Prime Vac | | + | + | + | + | + | + | − | + | + | − |
| InterVet | S903 | | + | + | + | − | + | − | − | + | − | − |
| Sofway | Bursine | (Luk) | + | + | + | + | + | + | − | − | − | − |
| Sofway | Bursine II | (Luke+) | + | + | + | + | + | + | − | − | − | − |
| | Lab Virus | | | | | | | | | | | |
| JKR | E/Del | | + | + | + | − | + | − | − | + | − | − |
| JKR | A/Del | | + | + | + | − | + | − | − | + | − | − |
| KKR | D/Del | | + | + | + | − | + | − | − | + | − | − |
| DBS | GLS | | + | + | + | + | − | − | − | + | + | − |
| DBS | DS326 | | + | + | − | + | − | − | − | + | + | + |
| *Skeele | S977 | | + | + | + | + | + | + | − | + | − | − |
| OH | | (Serotype II) | + | + | + | + | + | + | − | + | − | − |

*Field Strains: All classic filed strains tested to date which were isolated in the U.S. have the 21 marker.
NOTE: 1. Lukert and STC are Edgar derivatives. 2. Univax is a Bursa Vac derivative. 3. Bursa Blend is a 2512 Winterfield derivative.

It should be noted that throughout this application, reference is made to a variety of monoclonal antibody which are used to confirm the presence of epitopes of different IBDV in the inventive recombinant chimeric immunogens of the application. These monoclonal antibody have also been deposited under Budapest Treaty conditions and are freely available. They are not, however, necessary for the practice of this invention, and do not constitute an aspect thereof. This should be contrasted with Mab 21.

Like other Mab developed by the inventors herein for IBDV, passive immunization against IBDV lethal strains, particularly designed to achieve immunization in a uniform, standardized level, and to augment any maternally derived levels against lethal IBDV field infection can be obtained by vaccinating one-day old chicks with a vaccine comprising a pharmacologically acceptable carrier such as those described above, in which is present an amount of Mab 21 effective to provide enhanced protection for the inoculated chicks.

The necessary level of protection can be conferred to by a single dose of the vaccine administered in ova or to a day-old chick having a Mab 21 concentration of between 1 microgram and 1 milligram, or repeated vaccinations having a smaller effective dose, but carried out over time. If repeated vaccinations are used, the dosage levels should range between 1 microgram and 1 milligram. The concentration level needed to vaccinate older chickens increases with the weight of the bird and can be determined empirically.

Further investigation of the amino acid sequences of the lethal strains in the epitopic determinant region reflects the highly conserved 279 identity Asn at position 279 of VP2, in non-lethal strains, with a conserved Asp identity at the same position in lethal strains. Accordingly, the lethal strain epitopic determinant recognized by Mab 21, unique to the lethal strains, empirically differs from non-lethal IBDV by the substitution 279 Asp-Asn. According to the methods set forth above, a chimeric, recombinant immunogen conferring effective protection against lethal IBDV, something not possible previously with any type of vaccine without inducing an immunosuppressive condition, may be prepared by inserting the genetic epitopic determinant for 279 Asp in a non-lethal base IBDV, such as GLS. This will confer protection against the base IBDV, the lethal IBDV, as well as all other IBDV whose genetic epitopic determinants are inserted. Vaccines prepared from these immunogens, whether VP2 only, or in the form of virus-like particles of VP2-VP-VP3 segments, are used in the same fashion as discussed above.

```

What is claimed is:

1. A chimeric cDNA which, when operably inserted as a heterologous DNA in a DNA of an expression host, encodes a chimeric polypeptide immunogen comprising the VP2 amino acid sequence of a first infectious bursal disease virus (IBDV) strain except for at least one amino acid X, wherein X is an epitopic determinant from a second IBDV strain wherein said IBDV strains are selected from the group consisting of GLS, E/Del, D78, DS326, RS593, Cu-1, PBG98, 52/70, STC and 002-73, and wherein said immunogen comprises the amino acid sequence, in order, for IBDV structural proteins VP2-VP4-VP3.

2. A virus vector for the infection of an expression host, comprising the cDNA of claim 1 operably linked to the DNA of baculovirus fowlpox virus, turkey herpes virus or adenovirus.

3. A host cell for the expression of a chimeric polypeptide immunogen comprising the VP2 amino acid sequence of a first infectious bursal disease virus (IBDV) strain except for at least on amino acid X, wherein X is an epitopic determinant from a second IBDV strain, comprising an expression host selected from the group consisting of SF9 cells, chicken embryo fibroblast cells, chicken embryo kidney cells and vero cells transfected with the vector of claim 2.

4. The chimeric cDNA of claim 1, wherein said VP2 amino acid sequence comprises a plurality of different epitopic determinants X.

5. The chimeric cDNA of claim 4, wherein said plurality of epitopic determinants X are from at least two different IBDV strains.

6. The chimeric cDNA of claim 1, wherein said immunogen is in a form mimicking the three-dimensional structure of IBDV.

7. The chimeric cDNA of claim 6, wherein said immunogen exhibits at least one IBDV conformational epitope.

8. The chimeric cDNA of claim 1, wherein said amino acid sequence comprises an epitopic determinant X of a lethal IBDV strain.

9. The chimeric cDNA of claim 8, wherein said epitopic determinant of lethal IBDV strains comprises the amino acid Asp at position 279 of the VP2 sequence.

* * * * *

                        SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 1012 amino acids
        (B) TYPE: amino acid
        (C) STRANDEDNESS: unknown
        (D) TOPOLOGY: unknown (ii) MOLECULE TYPE: protein (vi) ORIGINAL SOURCE:
        (A) ORGANISM: Infectious bursal disease virus
        (B) STRAIN: GLS (xi) SEQUENCE DESCRIPTION: SEQ ID NO:1:

Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
                20                  25                  30

Leu Glu Lys His Thr Leu Arg Ser Glu Thr Ser Thr Tyr Asn Leu Thr
            35                  40                  45

Val Gly Asp Thr Gly Ser Gly Leu Ile Val Phe Phe Pro Gly Phe Pro
        50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
                100                 105                 110

Leu Pro Gly Gly Val Tyr Ala Leu Asn Gly Thr Ile Asn Ala Val Thr
            115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
```

-continued

```
                165                 170                 175
Tyr Val Arg Leu Gly Asp Pro Ile Pro Ala Ile Gly Leu Asp Pro Lys
                180                 185                 190
Met Val Ala Thr Cys Asp Ser Ser Asp Arg Pro Arg Val Tyr Thr Ile
                195                 200                 205
Thr Ala Ala Asp Asp Tyr Gln Phe Ser Ser Gln Tyr Gln Thr Gly Gly
                210                 215                 220
Val Thr Ile Thr Leu Phe Ser Ala Asn Ile Asp Ala Ile Thr Ser Leu
225                 230                 235                 240
Ser Val Gly Gly Glu Leu Val Phe Lys Thr Ser Val His Ser Leu Val
                245                 250                 255
Leu Gly Ala Thr Ile Tyr Leu Ile Gly Phe Asp Gly Ser Ala Val Ile
                260                 265                 270
Thr Arg Ala Val Ala Ala Asn Asn Gly Leu Thr Thr Gly Thr Asp Asn
                275                 280                 285
Leu Met Pro Phe Asn Leu Val Ile Pro Thr Asn Glu Ile Thr Gln Pro
                290                 295                 300
Ile Thr Ser Ile Lys Leu Glu Ile Val Thr Ser Lys Ser Gly Gly Gln
305                 310                 315                 320
Glu Gly Asp Gln Met Ser Trp Ser Ala Ser Gly Ser Leu Ala Val Thr
                325                 330                 335
Ile His Gly Gly Asn Tyr Pro Gly Ala Leu Arg Pro Val Thr Leu Val
                340                 345                 350
Ala Tyr Glu Arg Val Ala Thr Gly Ser Val Val Thr Val Ala Gly Val
                355                 360                 365
Ser Asn Phe Glu Leu Ile Pro Asn Pro Glu Leu Ala Lys Asn Leu Val
                370                 375                 380
Thr Glu Tyr Gly Arg Phe Asp Pro Gly Ala Met Asn Tyr Thr Lys Leu
385                 390                 395                 400
Ile Leu Ser Glu Arg Asp Arg Leu Gly Ile Lys Thr Val Trp Pro Thr
                405                 410                 415
Arg Glu Tyr Thr Asp Phe Arg Gly Tyr Phe Met Glu Val Ala Asp Leu
                420                 425                 430
Ser Ser Pro Leu Lys Ile Ala Gly Ala Phe Gly Phe Lys Asp Ile Ile
                435                 440                 445
Arg Ala Ile Arg Arg Ile Ala Val Pro Val Val Ser Thr Leu Phe Pro
450                 455                 460
Pro Ala Ala Pro Leu Ala His Ala Ile Gly Glu Gly Val Asp Tyr Leu
465                 470                 475                 480
Leu Gly Asp Glu Ala Gln Ala Ala Ser Gly Thr Ala Arg Ala Ala Ser
                485                 490                 495
Gly Lys Ala Arg Ala Ala Ser Gly Arg Ile Arg Gln Leu Thr Leu Ala
                500                 505                 510
Ala Asp Lys Gly Tyr Glu Val Val Ala Asn Leu Phe Gln Val Pro Gln
                515                 520                 525
Asn Pro Val Val Asp Gly Ile Leu Ala Ser Pro Gly Ile Leu Arg Gly
                530                 535                 540
Ala His Asn Leu Asp Cys Val Leu Arg Glu Gly Ala Thr Leu Phe Pro
545                 550                 555                 560
Val Val Ile Thr Thr Val Glu Asp Ala Met Thr Pro Lys Ala Leu Asn
                565                 570                 575
Ser Lys Met Phe Ala Val Ile Glu Gly Val Arg Glu Asp Leu Gln Pro
                580                 585                 590
```

-continued

Pro Ser Gln Arg Gly Ser Phe Ile Arg Thr Leu Ser Gly His Arg Val
    595                 600                 605

Tyr Gly Tyr Ala Pro Asp Gly Val Leu Pro Leu Glu Thr Gly Arg Asp
    610                 615                 620

Tyr Thr Val Val Pro Ile Asp Asp Val Trp Asp Ser Ile Met Leu
625                 630                 635                 640

Ser Lys Asp Pro Ile Pro Pro Ile Val Gly Asn Ser Gly Asn Leu Ala
                    645                 650                 655

Ile Ala Tyr Met Asp Val Phe Arg Pro Lys Val Pro Ile His Val Ala
            660                 665                 670

Met Thr Gly Ala Leu Asn Ala Cys Gly Glu Ile Glu Lys Ile Ser Phe
        675                 680                 685

Arg Ser Thr Lys Leu Ala Thr Ala His Arg Leu Gly Leu Lys Leu Ala
    690                 695                 700

Gly Pro Gly Ala Phe Asp Val Asn Thr Gly Pro Asn Trp Ala Thr Phe
705                 710                 715                 720

Ile Lys Arg Phe Pro His Asn Pro Arg Asp Trp Asp Arg Leu Pro Tyr
                    725                 730                 735

Leu Asn Leu Pro Tyr Leu Pro Pro Asn Ala Gly Arg Gln Tyr His Leu
            740                 745                 750

Ala Met Ala Ala Ser Glu Phe Lys Glu Thr Pro Glu Leu Glu Ser Ala
        755                 760                 765

Val Arg Ala Met Glu Ala Ala Ala Ser Val Asp Pro Leu Phe Gln Ser
    770                 775                 780

Ala Leu Ser Val Phe Met Trp Leu Glu Glu Asn Gly Ile Val Thr Asp
785                 790                 795                 800

Met Ala Asn Phe Ala Leu Ser Asp Pro Asn Ala His Arg Met Arg Asn
                    805                 810                 815

Phe Leu Ala Asn Ala Pro Gln Ala Gly Ser Lys Ser Gln Arg Ala Lys
            820                 825                 830

Tyr Gly Thr Ala Gly Tyr Gly Val Glu Ala Arg Gly Pro Thr Pro Glu
        835                 840                 845

Glu Ala Gln Arg Glu Lys Asp Thr Arg Ile Ser Lys Lys Met Glu Thr
    850                 855                 860

Met Gly Ile Tyr Phe Ala Thr Pro Glu Trp Val Ala Leu Asn Gly His
865                 870                 875                 880

Arg Gly Pro Ser Pro Gly Gln Leu Lys Tyr Trp Gln Asn Thr Arg Glu
                    885                 890                 895

Ile Pro Asp Pro Asn Glu Asp Tyr Leu Asp Tyr Val His Ala Glu Lys
            900                 905                 910

Ser Arg Leu Ala Ser Glu Glu Gln Ile Leu Arg Ala Ala Thr Ser Ile
        915                 920                 925

Tyr Gly Ala Pro Gly Gln Ala Glu Pro Pro Gln Ala Phe Ile Asp Glu
    930                 935                 940

Val Ala Lys Val Tyr Glu Ile Asn His Gly Arg Gly Pro Asn Gln Glu
945                 950                 955                 960

Gln Met Lys Asp Leu Leu Thr Ala Met Glu Met Lys His Arg Asn
                    965                 970                 975

Pro Arg Arg Ala Pro Pro Lys Pro Lys Pro Arg Pro Asn Ala Pro Thr
            980                 985                 990

Gln Arg Pro Pro Gly Arg Leu Gly Arg Trp Ile Arg Thr Val Ser Asp
        995                 1000                1005

Glu Asp Leu Glu
    1010

(2) INFORMATION FOR SEQ ID NO:2:

(i) SEQUENCE CHARACTERISTICS:
        (A) LENGTH: 1012 amino acids
        (B) TYPE: amino acid
        (C) STRANDEDNESS:
        (D) TOPOLOGY: unknown (ii) MOLECULE TYPE: protein (vi) ORIGINAL SOURCE:
        (A) ORGANISM: Infectious bursal disease virus
        (B) STRAIN: DS326

(xi) SEQUENCE DESCRIPTION: SEQ ID NO:2:

```
Met Thr Asn Leu Gln Asp Gln Thr Gln Gln Ile Val Pro Phe Ile Arg
 1               5                  10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Ser Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asn Asn Gly Leu Thr Ala Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Lys Ile Val Thr Ser Lys Ser Gly Gly Leu
305                 310                 315                 320

Glu Gly Asp Gln Met Ser Trp Ser Ala Ser Gly Ser Leu Ala Val Thr
                325                 330                 335
```

-continued

```
Ile His Gly Gly Asn Tyr Pro Gly Ala Leu Arg Pro Val Thr Leu Val
        340                 345                 350
Ala Tyr Glu Arg Val Ala Thr Gly Ser Val Val Thr Val Ala Gly Val
        355                 360                 365
Ser Asn Phe Glu Leu Ile Pro Asn Pro Glu Leu Ala Lys Asn Leu Val
        370                 375                 380
Thr Glu Tyr Gly Arg Phe Asp Pro Gly Ala Met Asn Tyr Thr Lys Leu
385                 390                 395                 400
Ile Leu Ser Glu Arg Asp Arg Leu Gly Ile Lys Thr Val Trp Pro Thr
                405                 410                 415
Arg Glu Tyr Thr Asp Phe Arg Glu Tyr Phe Met Glu Val Ala Asp Leu
                420                 425                 430
Asn Ser Pro Leu Lys Ile Ala Gly Ala Phe Gly Phe Lys Asp Ile Ile
            435                 440                 445
Arg Ala Ile Arg Arg Ile Ala Val Pro Val Val Ser Thr Leu Phe Pro
450                 455                 460
Pro Ala Ala Pro Leu Ala His Ala Ile Gly Glu Gly Val Asp Tyr Leu
465                 470                 475                 480
Leu Gly Asp Glu Ala Gln Ala Ala Ser Gly Thr Ala Arg Ala Ala Ser
                485                 490                 495
Gly Lys Ala Arg Ala Ala Ser Gly Arg Ile Arg Gln Leu Thr Leu Ala
                500                 505                 510
Ala Asp Lys Gly Tyr Glu Val Val Ala Asn Leu Phe Gln Val Pro Gln
            515                 520                 525
Asn Pro Val Val Asp Gly Ile Leu Ala Ser Pro Gly Ile Leu Arg Gly
530                 535                 540
Ala His Asn Leu Asp Cys Val Leu Arg Glu Gly Ala Thr Leu Phe Pro
545                 550                 555                 560
Val Val Ile Thr Thr Val Glu Asp Ala Met Thr Pro Lys Ala Leu Asn
                565                 570                 575
Ser Lys Met Phe Ala Val Ile Glu Gly Ala Arg Glu Asp Leu Gln Pro
                580                 585                 590
Pro Ser Gln Arg Gly Ser Phe Ile Arg Thr Leu Ser Gly His Arg Val
            595                 600                 605
Tyr Gly Tyr Ala Pro Asp Gly Val Leu Pro Leu Glu Thr Gly Arg Asp
        610                 615                 620
Tyr Thr Val Val Pro Ile Asp Asp Val Trp Asp Ser Ile Met Leu
625                 630                 635                 640
Ser Lys Asp Pro Ile Pro Pro Ile Val Gly Asn Ser Gly Asn Leu Ala
                645                 650                 655
Ile Ala Tyr Met Asp Val Phe Arg Pro Lys Val Pro Ile His Val Ala
                660                 665                 670
Met Thr Gly Ala Leu Asn Ala Tyr Gly Glu Ile Glu Lys Ile Ser Phe
            675                 680                 685
Arg Ser Thr Lys Leu Ala Thr Ala His Arg Leu Gly Leu Lys Leu Ala
        690                 695                 700
Gly Pro Gly Ala Phe Asp Val Asn Thr Gly Pro Asn Trp Ala Thr Phe
705                 710                 715                 720
Ile Lys Arg Phe Pro His Asn Pro Arg Asp Trp Asp Arg Leu Pro Tyr
                725                 730                 735
Leu Asn Leu Pro Tyr Leu Pro Asn Ala Gly Arg Gln Tyr His Leu
            740                 745                 750
Ala Met Ala Ala Ser Glu Phe Lys Glu Thr Pro Glu Leu Glu Ser Ala
```

```
                755                 760                 765
Val Arg Ala Met Glu Ala Ala Asn Val Asp Pro Leu Phe Gln Ser
    770                 775                 780
Ala Leu Ser Val Phe Met Trp Leu Glu Glu Asn Gly Ile Val Ala Asp
785                 790                 795                 800
Met Ala Asn Phe Ala Leu Ser Asp Pro Asn Ala His Arg Met Arg Asn
                805                 810                 815
Phe Leu Ala Asn Ala Pro Gln Ala Gly Ser Lys Ser Gln Arg Ala Lys
            820                 825                 830
Tyr Gly Thr Ala Gly Tyr Gly Val Glu Ala Arg Gly Pro Thr Pro Glu
            835                 840                 845
Glu Ala Gln Arg Glu Lys Asp Thr Arg Ile Ser Lys Lys Met Glu Thr
        850                 855                 860
Met Gly Ile Tyr Phe Ala Thr Pro Glu Trp Val Ala Leu Asn Gly His
865                 870                 875                 880
Arg Gly Pro Ser Pro Gly Gln Leu Lys Tyr Trp Gln Asn Thr Arg Glu
                885                 890                 895
Ile Pro Asp Pro Asn Glu Asp Tyr Leu Asp Tyr Val His Ala Glu Lys
            900                 905                 910
Ser Arg Leu Ala Ser Glu Glu Gln Ile Leu Lys Ala Ala Thr Ser Ile
        915                 920                 925
Tyr Gly Ala Pro Gly Gln Ala Glu Pro Pro Gln Ala Phe Ile Asp Glu
    930                 935                 940
Val Ala Lys Val Tyr Glu Ile Asn His Gly Arg Gly Pro Asn Gln Glu
945                 950                 955                 960
Gln Met Lys Asp Leu Leu Leu Thr Ala Met Glu Met Lys His Arg Asn
                965                 970                 975
Pro Arg Arg Ala Pro Pro Lys Pro Lys Pro Lys Pro Asn Ala Pro Thr
            980                 985                 990
Gln Arg Pro Pro Gly Arg Leu Gly Arg Trp Ile Arg Thr Val Ser Asp
        995                 1000                1005
Glu Asp Leu Glu
    1010

(2) INFORMATION FOR SEQ ID NO:3:

(i) SEQUENCE CHARACTERISTICS:
        (A) LENGTH: 1012 amino acids
        (B) TYPE: amino acid
        (C) STRANDEDNESS:
        (D) TOPOLOGY: unknown (ii) MOLECULE TYPE: protein (vi) ORIGINAL SOURCE:
        (A) ORGANISM: Infectious bursal disease virus
        (B) STRAIN: E/DEL (xi) SEQUENCE DESCRIPTION: SEQ ID NO:3:

Met Thr Asn Leu Gln Asp Gln Thr Gln Gln Ile Val Pro Phe Ile Arg
1               5                   10                  15
Ser Leu Leu Met Pro Thr Thr Gly Pro Ala Ser Ile Pro Asp Asp Thr
            20                  25                  30
Leu Glu Lys His Thr Leu Arg Ser Glu Thr Ser Thr Tyr Asn Leu Thr
        35                  40                  45
Val Gly Asp Thr Gly Ser Gly Leu Ile Val Phe Phe Pro Gly Phe Pro
    50                  55                  60
Gly Ser Ile Val Gly Ala His Tyr Thr Leu Gln Gly Asn Gly Asn Tyr
```

```
65                   70                   75                   80
Lys Phe Asp Gln Met Leu Leu Thr Ala Gln Asn Leu Pro Ala Ser Tyr
                 85                   90                   95
Asn Tyr Cys Arg Leu Val Ser Arg Ser Leu Thr Val Arg Ser Ser Thr
                100                  105                  110
Leu Pro Gly Gly Val Tyr Ala Leu Asn Gly Thr Ile Asn Ala Val Thr
                115                  120                  125
Phe Gln Gly Ser Leu Ser Glu Leu Thr Asp Val Ser Tyr Asn Gly Leu
            130                  135                  140
Met Ser Ala Thr Ala Asn Ile Asn Asp Lys Ile Gly Asn Val Leu Val
145                  150                  155                  160
Gly Glu Gly Val Thr Val Leu Ser Leu Pro Thr Ser Tyr Asp Leu Gly
                165                  170                  175
Tyr Val Arg Leu Gly Asp Pro Ile Pro Ala Ile Gly Leu Asp Pro Lys
                180                  185                  190
Met Val Ala Thr Cys Asp Ser Ser Asp Arg Pro Arg Val Tyr Thr Ile
                195                  200                  205
Thr Ala Ala Asp Asp Tyr Gln Phe Ser Ser Gln Tyr Gln Pro Gly Gly
            210                  215                  220
Val Thr Ile Thr Leu Phe Ser Ala Asn Ile Asp Ala Ile Thr Ser Leu
225                  230                  235                  240
Ser Val Gly Gly Glu Leu Val Phe Gln Thr Ser Val His Gly Leu Val
                245                  250                  255
Leu Gly Ala Thr Ile Tyr Leu Ile Gly Phe Asp Gly Thr Thr Val Ile
                260                  265                  270
Thr Arg Ala Val Ala Ala Asn Asn Gly Leu Thr Thr Gly Thr Asp Asn
            275                  280                  285
Leu Met Pro Phe Asn Leu Val Ile Pro Thr Asn Glu Ile Thr Gln Pro
            290                  295                  300
Ile Thr Ser Ile Lys Leu Glu Ile Val Thr Ser Lys Ser Gly Gly Gln
305                  310                  315                  320
Ala Gly Asp Gln Met Ser Trp Ser Ala Arg Gly Ser Leu Ala Val Thr
                325                  330                  335
Ile His Gly Gly Asn Tyr Pro Gly Ala Leu Arg Pro Val Thr Leu Val
                340                  345                  350
Ala Tyr Glu Arg Val Ala Thr Gly Ser Val Val Thr Val Ala Gly Val
                355                  360                  365
Ser Asn Phe Glu Leu Ile Pro Asn Pro Glu Leu Ala Lys Asn Leu Val
            370                  375                  380
Thr Glu Tyr Gly Arg Phe Asp Pro Gly Ala Met Asn Tyr Thr Lys Leu
385                  390                  395                  400
Ile Leu Ser Glu Arg Asp Arg Leu Gly Ile Lys Thr Val Trp Pro Thr
                405                  410                  415
Arg Glu Tyr Thr Asp Phe Arg Glu Tyr Phe Met Glu Val Ala Asp Leu
                420                  425                  430
Asn Ser Pro Leu Lys Ile Ala Gly Ala Phe Gly Phe Lys Asp Ile Ile
            435                  440                  445
Arg Ala Ile Arg Arg Ile Ala Val Pro Val Val Ser Thr Leu Phe Pro
450                  455                  460
Pro Ala Ala Pro Leu Ala His Ala Ile Gly Glu Gly Val Asp Tyr Leu
465                  470                  475                  480
Leu Gly Asp Glu Ala Gln Ala Ala Ser Gly Thr Ala Arg Ala Ala Ser
            485                  490                  495
```

-continued

```
Gly Lys Ala Arg Ala Ala Ser Gly Arg Ile Arg Gln Leu Thr Leu Ala
            500                 505                 510

Ala Asp Lys Gly Tyr Glu Val Val Ala Asn Leu Phe Gln Val Pro Gln
            515                 520                 525

Asn Pro Val Val Asp Gly Ile Leu Ala Ser Pro Gly Val Leu Arg Gly
            530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
                565                 570                 575

Ser Lys Met Phe Ala Val Ile Glu Gly Val Arg Glu Asp Leu Gln Pro
            580                 585                 590

Pro Ser Gln Arg Gly Ser Phe Ile Arg Thr Leu Ser Gly His Arg Val
            595                 600                 605

Tyr Gly Tyr Ala Pro Asp Gly Val Leu Pro Leu Glu Thr Gly Arg Asp
            610                 615                 620

Tyr Thr Val Val Pro Ile Asp Asp Val Trp Asp Ser Ile Met Leu
625                 630                 635                 640

Ser Lys Asp Pro Ile Pro Pro Ile Val Gly Asn Ser Gly Asn Leu Ala
            645                 650                 655

Ile Ala Tyr Met Asp Val Phe Arg Pro Lys Val Pro Ile His Val Ala
            660                 665                 670

Met Thr Gly Ala Leu Asn Ala Cys Gly Glu Ile Glu Lys Val Ser Phe
            675                 680                 685

Arg Ser Thr Lys Leu Ala Thr Ala His Arg Leu Gly Leu Arg Leu Ala
            690                 695                 700

Gly Pro Gly Ala Phe Asp Val Asn Thr Gly Pro Asn Trp Ala Thr Phe
705                 710                 715                 720

Ile Lys Arg Phe Pro His Asn Pro Arg Asp Trp Asp Arg Leu Pro Tyr
                725                 730                 735

Leu Asn Leu Pro Tyr Leu Pro Pro Asn Ala Gly Arg Gln Tyr His Leu
            740                 745                 750

Ala Met Ala Ala Ser Glu Phe Lys Glu Thr Pro Glu Leu Glu Ser Ala
            755                 760                 765

Val Arg Ala Met Glu Ala Ala Asn Val Asp Pro Leu Phe Gln Ser
            770                 775                 780

Ala Leu Ser Val Phe Met Trp Leu Glu Glu Asn Gly Ile Val Thr Asp
785                 790                 795                 800

Met Ala Asn Phe Ala Leu Ser Asp Pro Asn Ala His Arg Met Arg Asn
                805                 810                 815

Phe Leu Ala Asn Ala Pro Gln Ala Gly Ser Lys Ser Gln Arg Ala Lys
            820                 825                 830

Tyr Gly Thr Ala Gly Tyr Gly Val Glu Ala Arg Gly Pro Thr Pro Glu
            835                 840                 845

Glu Ala Gln Arg Glu Lys Asp Thr Arg Ile Ser Lys Lys Met Glu Thr
            850                 855                 860

Met Gly Ile Tyr Phe Ala Thr Pro Glu Trp Val Ala Leu Asn Gly His
865                 870                 875                 880

Arg Gly Pro Ser Pro Gly Gln Leu Lys Tyr Trp Gln Asn Thr Arg Glu
                885                 890                 895

Ile Pro Asp Pro Asn Glu Asp Tyr Leu Asp Tyr Val His Ala Glu Lys
            900                 905                 910

Ser Arg Leu Ala Ser Glu Glu Gln Ile Leu Arg Ala Ala Thr Ser Ile
            915                 920                 925
```

-continued

```
Tyr Gly Ala Pro Gly Gln Ala Glu Pro Pro Gln Ala Phe Ile Asp Glu
        930                 935                 940

Val Ala Lys Val Tyr Glu Ile Asn His Gly Arg Gly Pro Asn Gln Glu
945                 950                 955                 960

Gln Met Lys Asp Leu Leu Thr Ala Met Glu Met Lys His Arg Asn
                965                 970                 975

Pro Arg Arg Ala Leu Pro Lys Pro Lys Pro Lys Pro Asn Ala Pro Thr
                980                 985                 990

Gln Arg Pro Pro Gly Arg Leu Gly Arg Trp Ile Arg Thr Val Ser Asp
                995                 1000                1005

Glu Asp Leu Glu
    1010

(2) INFORMATION FOR SEQ ID NO:4:

(i) SEQUENCE CHARACTERISTICS:
        (A) LENGTH: 1012 amino acids
        (B) TYPE: amino acid
        (C) STRANDEDNESS:
        (D) TOPOLOGY: unknown (ii) MOLECULE TYPE: protein (vi) ORIGINAL SOURCE:
        (A) ORGANISM: Infectious bursal disease virus
        (B) STRAIN: D78

(xi) SEQUENCE DESCRIPTION: SEQ ID NO:4:

Met Thr Asn Leu Gln Asp Gln Thr His Gln Ile Val Pro Phe Ile Arg
1               5                   10                  15

Ser Leu Leu Met Pro Thr Thr Gly Pro Ala Ser Ile Pro Asp Asp Thr
                20                  25                  30

Leu Glu Lys His Thr Leu Arg Ser Glu Thr Ser Thr Tyr Asn Leu Thr
                35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Ser Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
                100                 105                 110

Leu Pro Gly Gly Val Tyr Ala Leu Asn Gly Thr Ile Asn Ala Val Thr
                115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
                180                 185                 190

Met Val Ala Thr Cys Asp Ser Ser Asp Arg Pro Arg Val Tyr Thr Ile
                195                 200                 205

Thr Ala Ala Asp Asn Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240
```

-continued

```
Ser Val Gly Gly Glu Leu Val Phe Lys Thr Ser Val Gln Ser Leu Val
                245                 250                 255
Leu Gly Ala Thr Ile Tyr Leu Ile Gly Phe Asp Gly Thr Ala Val Ile
            260                 265                 270
Thr Arg Ala Val Ala Ala Asn Asn Gly Leu Thr Ala Gly Ile Asp Asn
        275                 280                 285
Leu Met Pro Phe Asn Leu Val Ile Pro Thr Asn Glu Ile Thr Gln Pro
    290                 295                 300
Ile Thr Ser Ile Ile Leu Glu Ile Val Thr Ser Lys Ser Asp Gly Gln
305                 310                 315                 320
Ala Gly Glu Gln Met Ser Trp Ser Ala Ser Gly Ser Leu Ala Val Thr
                325                 330                 335
Ile His Gly Gly Asn Tyr Pro Gly Ala Leu Arg Pro Val Thr Leu Val
            340                 345                 350
Ala Tyr Glu Arg Val Ala Thr Gly Ser Val Val Thr Val Ala Gly Val
        355                 360                 365
Ser Asn Phe Glu Leu Ile Pro Asn Pro Glu Leu Ala Lys Asn Leu Val
    370                 375                 380
Thr Glu Tyr Gly Arg Phe Asp Pro Gly Ala Met Asn Tyr Thr Lys Leu
385                 390                 395                 400
Ile Leu Ser Glu Arg Asp His Leu Gly Ile Lys Thr Val Trp Pro Thr
                405                 410                 415
Arg Glu Tyr Thr Asp Phe Arg Glu Tyr Phe Met Glu Val Ala Asp Leu
            420                 425                 430
Asn Ser Pro Leu Lys Ile Ala Gly Ala Phe Gly Phe Lys Asp Ile Ile
        435                 440                 445
Arg Ala Ile Arg Arg Ile Ala Val Pro Val Val Ser Thr Leu Phe Pro
    450                 455                 460
Pro Ala Ala Pro Leu Ala His Ala Ile Gly Glu Gly Val Asp Tyr Leu
465                 470                 475                 480
Leu Gly Asp Glu Ala Gln Ala Ala Ser Gly Thr Ala Arg Ala Ala Ser
                485                 490                 495
Gly Lys Ala Arg Ala Ala Ser Gly Arg Ile Arg Gln Leu Thr Leu Ala
            500                 505                 510
Ala Asp Lys Gly Tyr Glu Val Val Ala Asn Leu Phe Gln Val Pro Gln
        515                 520                 525
Asn Pro Val Val Asp Gly Ile Leu Ala Ser Pro Gly Ile Leu Arg Gly
    530                 535                 540
Ala His Asn Leu Asp Cys Val Leu Arg Glu Gly Ala Thr Leu Phe Pro
545                 550                 555                 560
Val Val Ile Thr Thr Val Glu Asp Ala Met Thr Pro Lys Ala Leu Asn
                565                 570                 575
Ser Lys Met Phe Ala Val Ile Glu Gly Val Arg Glu Asp Leu Gln Pro
            580                 585                 590
Pro Ser Gln Arg Gly Ser Phe Ile Arg Thr Leu Ser Gly His Arg Val
        595                 600                 605
Tyr Gly Tyr Ala Pro Asp Gly Val Leu Pro Leu Glu Thr Gly Arg Asp
    610                 615                 620
Tyr Thr Val Val Pro Ile Asp Asp Val Trp Asp Ser Ile Met Leu
625                 630                 635                 640
Ser Lys Asp Pro Ile Pro Pro Val Gly Asn Ser Gly Asn Leu Ala
                645                 650                 655
Ile Ala Tyr Met Asp Val Phe Arg Pro Lys Val Pro Ile His Val Ala
```

-continued

```
                        660                     665                     670
    Met Thr Gly Ala Leu Asn Ala Cys Gly Glu Ile Glu Lys Ile Ser Phe
                675                     680                     685

Arg Ser Thr Lys Leu Ala Thr Ala His Arg Leu Gly Leu Lys Leu Ala
            690                     695                     700

Gly Pro Gly Ala Phe Asp Val Asn Thr Gly Pro Asn Trp Ala Thr Phe
705                     710                     715                     720

Ile Lys Arg Phe Pro His Asn Pro Arg Asp Trp Asp Arg Leu Pro Tyr
                        725                     730                     735

Leu Asn Leu Pro Tyr Leu Pro Pro Asn Ala Gly Arg Gln Tyr His Leu
                740                     745                     750

Ala Met Ala Ala Ser Glu Phe Lys Glu Thr Pro Glu Leu Glu Ser Ala
                755                     760                     765

Val Arg Ala Met Glu Ala Ala Ala Asn Val Asp Pro Leu Phe Gln Ser
770                     775                     780

Ala Leu Ser Val Phe Met Trp Leu Glu Glu Asn Gly Ile Val Thr Asp
785                     790                     795                     800

Met Ala Asn Phe Ala Leu Ser Asp Pro Asn Ala His Arg Met Arg Asn
                        805                     810                     815

Phe Leu Ala Asn Ala Pro Gln Ala Gly Ser Lys Ser Gln Arg Ala Lys
                820                     825                     830

Tyr Gly Thr Ala Gly Tyr Gly Val Glu Ala Arg Gly Pro Thr Pro Glu
                835                     840                     845

Glu Ala Gln Arg Glu Lys Asp Thr Arg Ile Ser Lys Lys Met Glu Thr
            850                     855                     860

Met Gly Ile Tyr Phe Ala Thr Pro Glu Trp Val Ala Leu Asn Gly His
865                     870                     875                     880

Arg Gly Pro Ser Pro Gly Gln Leu Lys Tyr Trp Gln Asn Thr Arg Glu
                        885                     890                     895

Ile Pro Asp Pro Asn Glu Asp Tyr Leu Asp Tyr Val His Ala Glu Lys
                900                     905                     910

Ser Arg Leu Ala Ser Glu Glu Gln Ile Leu Arg Ala Ala Thr Ser Ile
                915                     920                     925

Tyr Gly Ala Pro Gly Gln Ala Glu Pro Pro Gln Ala Phe Ile Asp Glu
            930                     935                     940

Val Ala Lys Val Tyr Glu Ile Asn His Gly Arg Gly Pro Asn Gln Gly
945                     950                     955                     960

Gln Met Lys Asp Leu Leu Leu Thr Ala Met Glu Met Lys His Arg Asn
                        965                     970                     975

Pro Arg Arg Ala Pro Pro Lys Pro Lys Pro Lys Pro Asn Ala Pro Thr
                980                     985                     990

Gln Arg Pro Pro Gly Arg Leu Gly Arg Trp Ile Arg Thr Val Ser Asp
                995                     1000                    1005

Glu Asp Leu Glu
        1010

(2) INFORMATION FOR SEQ ID NO:5:

(i) SEQUENCE CHARACTERISTICS:
        (A) LENGTH: 1012 amino acids
        (B) TYPE: amino acid
        (C) STRANDEDNESS:
        (D) TOPOLOGY: unknown (ii) MOLECULE TYPE: protein (vi) ORIGINAL SOURCE:
```

(A) ORGANISM: Infectious bursal disease virus
(B) STRAIN: CU-1

(xi) SEQUENCE DESCRIPTION: SEQ ID NO:5:

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
                20                  25                  30

Leu Glu Lys His Thr Leu Arg Ser Glu Thr Ser Thr Tyr Asn Leu Thr
            35                  40                  45

Val Gly Asp Thr Gly Ser Gly Leu Ile Val Phe Phe Pro Gly Phe Pro
        50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Gln Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Ser Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Lys Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400
```

```
Ile Leu Ser Glu Arg Asp Arg Leu Gly Ile Lys Thr Val Trp Pro Thr
            405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
            435                 440                 445

Arg Ala Ile Arg Arg Ile Ala Val Pro Val Val Ser Thr Leu Phe Pro
450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
            500                 505                 510

Ala Asp Lys Gly Tyr Glu Val Val Ala Asn Leu Phe Gln Val Pro Gln
            515                 520                 525

Asn Pro Val Val Asp Gly Ile Leu Ala Ser Pro Gly Val Leu Arg Gly
            530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
                565                 570                 575

Ser Lys Met Phe Ala Val Ile Glu Gly Val Arg Glu Asp Leu Gln Pro
            580                 585                 590

Pro Ser Gln Arg Gly Ser Phe Ile Arg Thr Leu Ser Gly His Arg Val
            595                 600                 605

Tyr Gly Tyr Ala Pro Asp Gly Val Leu Pro Leu Glu Thr Gly Arg Asp
            610                 615                 620

Tyr Thr Val Val Pro Ile Asp Asp Val Trp Asp Ser Ile Met Leu
625                 630                 635                 640

Ser Lys Asp Pro Ile Pro Pro Ile Val Gly Asn Ser Gly Asn Leu Ala
                645                 650                 655

Ile Ala Tyr Met Asp Val Phe Arg Pro Lys Val Pro Ile His Val Ala
                660                 665                 670

Met Thr Gly Ala Leu Asn Ala Cys Gly Glu Ile Glu Lys Val Ser Phe
            675                 680                 685

Arg Ser Thr Lys Leu Ala Thr Ala His Arg Leu Gly Leu Lys Leu Ala
            690                 695                 700

Gly Pro Gly Ala Phe Asp Val Asn Thr Gly Pro Asn Trp Ala Thr Phe
705                 710                 715                 720

Ile Lys Arg Phe Pro His Asn Pro Arg Asp Trp Asp Arg Leu Pro Tyr
                725                 730                 735

Leu Asn Leu Pro Tyr Leu Pro Pro Asn Ala Gly Arg Gln Tyr His Leu
            740                 745                 750

Ala Met Ala Ala Ser Glu Phe Lys Glu Thr Pro Glu Leu Glu Ser Ala
            755                 760                 765

Val Arg Ala Met Glu Ala Ala Asn Val Asp Pro Leu Phe Gln Ser
            770                 775                 780

Ala Leu Ser Val Phe Met Trp Leu Glu Glu Asn Gly Ile Val Thr Asp
785                 790                 795                 800

Met Ala Asn Phe Ala Leu Ser Asp Pro Asn Ala His Arg Met Arg Asn
                805                 810                 815

Phe Leu Ala Asn Ala Pro Gln Ala Gly Ser Lys Ser Gln Arg Ala Lys
                820                 825                 830
```

```
Tyr Gly Thr Ala Gly Tyr Gly Val Glu Ala Arg Gly Pro Thr Pro Glu
            835                 840                 845
Glu Ala Gln Arg Glu Lys Asp Thr Arg Ile Ser Lys Lys Met Glu Thr
    850                 855                 860
Met Gly Ile Tyr Phe Ala Thr Pro Glu Trp Val Ala Leu Asn Gly His
865                 870                 875                 880
Arg Gly Pro Ser Pro Gly Gln Leu Lys Tyr Trp Gln Asn Thr Arg Glu
            885                 890                 895
Ile Pro Asp Pro Asn Glu Asp Tyr Leu Asp Tyr Val His Ala Glu Lys
        900                 905                 910
Ser Arg Leu Ala Ser Glu Glu Gln Ile Leu Arg Ala Ala Thr Ser Ile
            915                 920                 925
Tyr Gly Ala Pro Gly Gln Ala Glu Pro Pro Gln Ala Phe Ile Asp Glu
    930                 935                 940
Val Ala Lys Val Tyr Glu Ile Asn His Gly Arg Gly Pro Asn Gln Glu
945                 950                 955                 960
Gln Met Lys Asp Leu Leu Leu Thr Ala Met Glu Met Lys His Arg Asn
            965                 970                 975
Pro Arg Arg Ala Leu Pro Lys Pro Lys Pro Lys Pro Asn Ala Pro Thr
        980                 985                 990
Gln Arg Pro Pro Gly Arg Leu Gly Arg Trp Ile Arg Thr Val Ser Asp
            995                 1000                1005
Glu Asp Leu Glu
    1010

(2) INFORMATION FOR SEQ ID NO:6:

(i) SEQUENCE CHARACTERISTICS:
        (A) LENGTH: 1012 amino acids
        (B) TYPE: amino acid
        (C) STRANDEDNESS:
        (D) TOPOLOGY: unknown (ii) MOLECULE TYPE: protein (vi) ORIGINAL SOURCE:
        (A) ORGANISM: Infectious bursal disease virus
        (B) STRAIN: PBG98

(xi) SEQUENCE DESCRIPTION: SEQ ID NO:6:

Xaa Xaa Xaa Xaa Xaa Xaa Xaa Xaa Xaa Xaa Xaa Xaa Xaa Xaa Xaa Xaa
1               5                   10                  15
Xaa Xaa Xaa Met Pro Thr Thr Gly Pro Ala Ser Ile Pro Asp Asp Thr
            20                  25                  30
Leu Glu Lys His Thr Leu Arg Ser Glu Thr Ser Thr Tyr Asn Leu Thr
        35                  40                  45
Val Gly Asp Thr Gly Ser Gly Leu Ile Val Phe Phe Pro Gly Phe Pro
    50                  55                  60
Gly Ser Ile Val Gly Ala His Tyr Thr Leu Gln Ser Asn Gly Asn Tyr
65                  70                  75                  80
Lys Phe Asp Gln Met Leu Leu Thr Ala Gln Asn Leu Pro Ala Ser Tyr
            85                  90                  95
Asn Tyr Cys Arg Leu Val Ser Arg Ser Leu Thr Val Arg Ser Ser Thr
            100                 105                 110
Leu Pro Gly Gly Val Tyr Ala Leu Asn Gly Thr Ile Asn Ala Val Thr
        115                 120                 125
Phe Gln Gly Ser Leu Ser Glu Leu Thr Asp Val Ser Tyr Asn Gly Leu
    130                 135                 140
```

```
Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
            165                 170                 175

Tyr Val Arg Leu Gly Asp Pro Ile Pro Ala Ile Gly Leu Asp Pro Lys
        180                 185                 190

Met Val Ala Thr Cys Asp Ser Ser Asp Arg Pro Arg Val Tyr Thr Ile
    195                 200                 205

Thr Ala Ala Asp Asp Tyr Gln Phe Ser Gln Tyr Gln Pro Gly Gly
210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Arg Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Thr Gly Leu Thr Thr Gly Thr Asp Asn
        275                 280                 285

Leu Met Pro Phe Asn Leu Val Ile Pro Thr Asn Glu Ile Thr Gln Pro
290                 295                 300

Ile Thr Ser Ile Lys Leu Glu Ile Val Thr Ser Lys Ser Gly Gly Gln
305                 310                 315                 320

Ala Gly Asp Gln Met Leu Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val Pro Val Ser Thr Leu Phe Pro
450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
            500                 505                 510

Ala Asp Lys Gly Tyr Glu Val Val Ala Asn Leu Phe Gln Val Pro Gln
        515                 520                 525

Asn Pro Val Val Asp Gly Ile Leu Ala Ser Pro Gly Val Leu Arg Gly
530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
```

-continued

```
                565                 570                 575
Ser Lys Met Phe Ala Val Ile Glu Gly Val Arg Glu Asp Leu Gln Pro
            580                 585                 590
Pro Ser Gln Arg Gly Ser Phe Ile Arg Thr Leu Ser Gly His Arg Val
            595                 600                 605
Tyr Gly Tyr Ala Pro Asp Gly Val Leu Pro Leu Glu Thr Gly Arg Asp
610                 615                 620
Tyr Thr Val Val Pro Ile Asp Asp Val Trp Asp Ser Ile Met Leu
625                 630                 635                 640
Ser Lys Asp Pro Ile Pro Pro Ile Val Gly Asn Ser Gly Asn Leu Ala
            645                 650                 655
Ile Ala Tyr Met Asp Val Phe Arg Pro Lys Val Pro Ile His Val Ala
            660                 665                 670
Met Thr Gly Ala Leu Asn Ala Cys Gly Glu Ile Glu Lys Val Ser Phe
            675                 680                 685
Arg Ser Thr Lys Leu Ala Thr Ala His Arg Leu Gly Leu Lys Leu Ala
            690                 695                 700
Gly Pro Gly Ala Phe Asp Val Asn Thr Gly Pro Asn Trp Ala Thr Phe
705                 710                 715                 720
Ile Lys Arg Phe Pro His Asn Pro Arg Asp Trp Asp Arg Leu Pro Tyr
            725                 730                 735
Leu Asn Leu Pro Tyr Leu Pro Pro Asn Ala Gly Arg Gln Tyr His Leu
            740                 745                 750
Ala Met Ala Ala Ser Glu Phe Lys Glu Thr Pro Glu Leu Glu Ser Ala
            755                 760                 765
Val Arg Ala Met Glu Ala Ala Asn Val Asp Pro Leu Phe Gln Ser
            770                 775                 780
Ala Leu Ser Val Phe Met Trp Leu Glu Glu Asn Gly Ile Val Thr Asp
785                 790                 795                 800
Met Ala Asn Phe Ala Leu Ser Asp Pro Asn Ala His Arg Met Arg Asn
            805                 810                 815
Phe Leu Ala Asn Ala Pro Gln Ala Gly Ser Lys Ser Gln Arg Ala Lys
            820                 825                 830
Tyr Gly Thr Ala Gly Tyr Gly Val Glu Ala Arg Gly Pro Thr Pro Glu
            835                 840                 845
Glu Ala Gln Arg Glu Lys Asp Thr Arg Ile Ser Lys Lys Met Glu Thr
850                 855                 860
Met Gly Ile Tyr Phe Ala Thr Pro Glu Trp Val Ala Leu Asn Gly His
865                 870                 875                 880
Arg Gly Pro Ser Pro Gly Gln Leu Lys Tyr Trp Gln Asn Thr Arg Glu
            885                 890                 895
Ile Pro Asp Pro Asn Glu Asp Tyr Leu Asp Tyr Val His Ala Glu Lys
            900                 905                 910
Ser Arg Leu Ala Ser Glu Glu Gln Ile Leu Arg Ala Ala Thr Ser Ile
            915                 920                 925
Tyr Gly Ala Pro Gly Gln Ala Glu Pro Gln Ala Phe Ile Asp Glu
            930                 935                 940
Val Ala Lys Val Tyr Glu Ile Asn His Gly Arg Gly Pro Asn Gln Glu
945                 950                 955                 960
Gln Met Lys Asp Leu Leu Thr Ala Met Glu Met Lys His Arg Asn
            965                 970                 975
Pro Arg Arg Ala Leu Pro Lys Pro Lys Pro Lys Pro Asn Ala Pro Thr
            980                 985                 990
```

-continued

Gln Arg Pro Gly Arg Leu Gly Arg Trp Ile Arg Thr Val Ser Asp
    995                 1000                1005

Glu Asp Leu Glu
    1010

(2) INFORMATION FOR SEQ ID NO:7:

(i) SEQUENCE CHARACTERISTICS:
        (A) LENGTH: 1012 amino acids
        (B) TYPE: amino acid
        (C) STRANDEDNESS:
        (D) TOPOLOGY: unknown (ii) MOLECULE TYPE: protein (vi) ORIGINAL SOURCE:
        (A) ORGANISM: Infectious bursal disease virus
        (B) STRAIN: 52/70

(xi) SEQUENCE DESCRIPTION: SEQ ID NO:7:

Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asp Asn Gly Leu Thr Ala Gly Thr Asp Asn
        275                 280                 285

Leu Met Pro Phe Asn Leu Val Ile Pro Thr Asn Glu Ile Thr Gln Pro
290                 295                 300

```
Ile Thr Ser Ile Lys Leu Glu Ile Val Thr Ser Lys Ser Gly Gly Gln
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
                340                 345                 350

Ala Tyr Glu Arg Val Ala Thr Gly Ser Val Val Thr Val Ala Gly Val
            355                 360                 365

Ser Asn Phe Glu Leu Ile Pro Asn Pro Glu Leu Ala Lys Asn Leu Val
370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
                420                 425                 430

Asn Ser Pro Leu Lys Ile Ala Gly Ala Phe Gly Phe Lys Asp Ile Ile
                435                 440                 445

Arg Ala Ile Arg Arg Ile Ala Val Pro Val Val Ser Thr Leu Phe Pro
            450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
                500                 505                 510

Ala Asp Lys Gly Tyr Glu Val Val Ala Asn Leu Phe Gln Val Pro Gln
            515                 520                 525

Asn Pro Val Val Asp Gly Ile Leu Ala Ser Pro Gly Val Leu Arg Gly
530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
                565                 570                 575

Ser Lys Met Phe Ala Val Ile Glu Gly Val Arg Glu Asp Leu Gln Pro
                580                 585                 590

Pro Ser Gln Arg Gly Ser Phe Ile Arg Thr Leu Ser Gly His Arg Val
            595                 600                 605

Tyr Gly Tyr Ala Pro Asp Gly Val Leu Pro Leu Glu Thr Gly Arg Asp
            610                 615                 620

Tyr Thr Val Val Pro Ile Asp Asp Val Trp Asp Ser Ile Met Leu
625                 630                 635                 640

Ser Lys Asp Pro Ile Pro Pro Ile Val Gly Asn Ser Gly Asn Leu Ala
                645                 650                 655

Ile Ala Tyr Met Asp Val Phe Arg Pro Lys Val Pro Ile His Val Ala
                660                 665                 670

Met Thr Gly Ala Pro Asn Ala Cys Gly Glu Ile Glu Lys Ile Ser Phe
                675                 680                 685

Arg Ser Thr Lys Leu Ala Thr Ala His Arg Leu Gly Leu Lys Leu Ala
            690                 695                 700

Gly Pro Gly Ala Phe Asp Val Asn Thr Gly Pro Asn Trp Ala Thr Phe
705                 710                 715                 720

Ile Lys Arg Phe Pro His Asn Pro Arg Asp Trp Asp Arg Leu Pro Tyr
                725                 730                 735
```

-continued

```
Leu Asn Leu Pro Tyr Leu Pro Pro Asn Ala Gly Arg Gln Tyr His Leu
            740                 745                 750

Ala Met Ala Ala Ser Glu Phe Lys Asp Thr Pro Glu Leu Glu Ser Ala
            755                 760                 765

Val Arg Ala Met Glu Ala Ala Asn Val Asp Ser Leu Phe Gln Ser
            770                 775             780

Ala Leu Ser Val Phe Met Trp Leu Glu Glu Asn Gly Ile Val Thr Asp
785                 790                 795                 800

Met Ala Asn Phe Thr Leu Ser Asp Pro Asn Ala His Arg Met Arg Asn
                805                 810                 815

Phe Leu Ala Asn Ala Pro Gln Ala Gly Ser Lys Ser Gln Arg Ala Lys
            820                 825                 830

Tyr Gly Thr Ala Gly Tyr Gly Val Glu Ala Arg Gly Pro Thr Pro Glu
            835                 840                 845

Glu Ala Gln Arg Lys Lys As

-continued

Val Gly Asp Thr Gly Ser Gly Leu Ile Val Phe Phe Pro Gly Phe Pro
 50                     55                  60

Gly Ser Ile Val Gly Ala His Tyr Thr Leu Gln Ser Asn Gly Asn Leu
 65                  70              75                      80

Lys Phe Asp Gln Met Leu Leu Thr Ala Gln Asn Leu Pro Ala Ser Tyr
                 85              90              95

Asn Tyr Cys Arg Leu Val Ser Arg Ser Leu Thr Val Arg Ser Ser Thr
             100             105             110

Leu Pro Gly Gly Val Tyr Ala Leu Asn Gly Thr Ile Asn Ala Val Thr
             115             120             125

Phe Gln Gly Ser Leu Ser Glu Leu Thr Asp Val Ser Tyr Asn Gly Leu
         130             135             140

Met Ser Ala Thr Ala Asn Ile Asn Asp Lys Ile Gly Asn Val Leu Val
 145                 150             155                     160

Gly Glu Gly Val Thr Val Leu Ser Leu Pro Thr Ser Tyr Asp Leu Gly
                 165             170             175

Tyr Val Arg Leu Gly Asp Pro Ile Pro Ala Ile Gly Leu Asp Pro Lys
             180             185             190

Met Val Ala Thr Cys Asp Ser Ser Asp Arg Pro Arg Val Tyr Thr Ile
             195             200             205

Thr Ala Ala Asp Asp Tyr Gln Phe Ser Ser Gln Tyr Gln Pro Gly Gly
 210             215             220

Val Thr Ile Thr Leu Phe Ser Ala Asn Ile Asp Ala Ile Thr Ser Leu
225             230             235             240

Ser Val Gly Gly Glu Leu Val Phe Gln Thr Ser Val Gln Gly Leu Val
             245             250             255

Leu Gly Ala Thr Ile Tyr Phe Ile Gly Phe Asp Gly Thr Thr Val Ile
             260             265             270

Thr Arg Ala Val Ala Ala Asp Asn Gly Leu Thr Ala Gly Thr Asp Asn
     275             280             285

Leu Met Pro Phe Asn Leu Val Ile Pro Thr Asn Glu Ile Thr Gln Pro
 290             295             300

Ile Thr Ser Ile Lys Leu Glu Val Val Thr Ser Lys Ser Gly Gly Gln
305             310             315                     320

Ala Gly Asp Gln Met Ser Trp Ser Ala Ser Gly Ser Leu Ala Val Thr
             325             330             335

Ile His Gly Gly Asn Tyr Pro Gly Ala Leu Arg Pro Val Thr Leu Val
             340             345             350

Ala Tyr Glu Arg Val Ala Thr Gly Ser Val Val Thr Val Ala Gly Val
             355             360             365

Ser Asn Phe Glu Leu Ile Pro Asn Pro Glu Leu Ala Lys Asn Leu Val
 370             375             380

Thr Glu Tyr Gly Arg Phe Asp Pro Gly Ala Met Asn Tyr Thr Lys Leu
385             390             395             400

Ile Leu Ser Glu Arg Asp Arg Leu Gly Ile Lys Thr Val Trp Pro Thr
             405             410             415

Arg Glu Tyr Thr Asp Phe Arg Glu Tyr Phe Met Glu Val Ala Asp Leu
             420             425             430

Asn Ser Pro Leu Lys Ile Ala Gly Ala Phe Gly Phe Lys Asp Ile Ile
             435             440             445

Arg Ala Ile Arg Arg Ile Ala Val Pro Val Val Ser Thr Leu Phe Pro
 450             455             460

Pro Ala Ala Pro Leu Ala His Ala Ile Gly Glu Gly Val Asp Tyr Leu

```
               465                 470                 475                 480
Leu Gly Asp Glu Ala Gln Ala Ala Ser Gly Thr Ala Arg Ala Ala Ser
                        485                 490                 495
Gly Lys Ala Arg Ala Ala Ser Gly Arg Ile Arg Gln Leu Thr Leu Ala
                500                 505                 510
Ala Asp Lys Gly Tyr Glu Val Val Ala Asn Leu Phe Gln Val Pro Gln
                515                 520                 525
Asn Pro Val Val Asp Gly Ile Leu Ala Ser Pro Gly Val Leu Arg Gly
            530                 535                 540
Ala His Asn Leu Asp Cys Val Leu Arg Glu Gly Ala Thr Leu Phe Pro
545                 550                 555                 560
Val Val Ile Thr Thr Val Glu Asp Ala Met Thr Pro Lys Ala Leu Asn
                565                 570                 575
Ser Lys Ile Phe Ala Val Ile Glu Gly Val Arg Glu Asp Leu Gln Pro
                580                 585                 590
Pro Ser Gln Arg Gly Ser Phe Ile Arg Thr Leu Ser Gly His Arg Val
                595                 600                 605
Tyr Gly Tyr Ala Pro Asp Gly Val Leu Pro Leu Glu Thr Gly Arg Asp
            610                 615                 620
Tyr Thr Val Val Pro Ile Asp Asp Val Trp Asp Ser Ile Met Leu
625                 630                 635                 640
Ser Lys Asp Pro Ile Pro Ile Val Gly Asn Ser Gly Asn Leu Ala
                    645                 650                 655
Ile Ala Tyr Met Asp Val Phe Arg Pro Lys Val Pro Ile His Val Ala
                660                 665                 670
Met Thr Gly Ala Leu Asn Ala Phe Gly Glu Ile Glu Lys Val Ser Phe
            675                 680                 685
Arg Ser Thr Lys Leu Ala Thr Ala His Arg Leu Gly Leu Lys Leu Ala
        690                 695                 700
Gly Pro Gly Ala Phe Asp Val Asn Thr Gly Pro Asn Trp Ala Thr Phe
705                 710                 715                 720
Ile Lys Arg Phe Pro His Asn Pro Arg Asp Trp Asp Arg Leu Pro Tyr
                    725                 730                 735
Leu Asn Leu Pro Tyr Leu Pro Pro Asn Ala Gly Arg Gln Tyr His Leu
                740                 745                 750
Ala Met Ala Ala Ser Glu Phe Lys Glu Thr Pro Glu Leu Glu Ser Ala
            755                 760                 765
Val Arg Ala Met Glu Ala Ala Asn Val Asp Pro Leu Phe Gln Ser
        770                 775                 780
Ala Leu Ser Val Phe Met Trp Leu Glu Glu Asn Gly Ile Val Thr Asp
785                 790                 795                 800
Met Ala Asn Phe Ala Leu Ser Asp Pro Asn Ala His Arg Met Arg Asn
                    805                 810                 815
Phe Leu Ala Asn Ala Pro Gln Ala Gly Ser Lys Ser Gln Arg Ala Lys
                820                 825                 830
Tyr Gly Thr Ala Gly Tyr Gly Val Glu Ala Arg Gly Pro Thr Pro Glu
            835                 840                 845
Glu Ala Gln Arg Ala Lys Asp Thr Arg Ile Ser Lys Lys Met Glu Thr
        850                 855                 860
Met Gly Ile Tyr Phe Ala Thr Pro Glu Trp Val Ala Leu Asn Gly His
865                 870                 875                 880
Arg Gly Pro Ser Pro Ala Gln Leu Lys Tyr Trp Gln Asn Thr Arg Glu
                    885                 890                 895
```

```
Ile Pro Asp Pro Asn Glu Asp Tyr Leu Asp Tyr Val His Ala Glu Lys
            900                 905                 910
Ser Arg Leu Ala Ser Glu Glu Gln Ile Leu Lys Ala Ala Thr Ser Ile
            915                 920                 925
Tyr Gly Ala Pro Gly Gln Ala Glu Pro Pro Gln Ala Phe Ile Asp Glu
            930                 935                 940
Val Ala Lys Val Tyr Glu Ile Asn His Gly Arg Gly Pro Asn Gln Glu
945                 950                 955                 960
Gln Met Lys Asp Leu Leu Leu Thr Ala Met Glu Leu Lys His Arg Asn
            965                 970                 975
Pro Arg Arg Ala Pro Pro Lys Pro Lys Pro Lys Pro Asn Ala Pro Thr
            980                 985                 990
Gln Arg Pro Pro Gly Arg Leu Gly Arg Trp Ile Arg Thr Val Ser Asp
            995                 1000                1005
Glu Asp Leu Glu
    1010
```

(2) INFORMATION FOR SEQ ID NO:9:

(i) SEQUENCE CHARACTERISTICS:
        (A) LENGTH: 1012 amino acids
        (B) TYPE: amino acid
        (C) STRANDEDNESS:
        (D) TOPOLOGY: unknown (ii) MOLECULE TYPE: protein (vi) ORIGINAL SOURCE:
        (A) ORGANISM: Infectious bursal disease virus
        (B) STRAIN: 002-73

(xi) SEQUENCE DESCRIPTION: SEQ ID NO:9:

```
Met Thr Asn Leu Ser Asp Gln Thr Gln Gln Ile Val Pro Phe Ile Arg
1               5                   10                  15
Ser Leu Leu Met Pro Thr Thr Gly Pro Ala Ser Ile Pro Asp Asp Thr
            20                  25                  30
Leu Glu Lys His Thr Leu Arg Ser Glu Thr Ser Thr Tyr Asn Leu Thr
            35                  40                  45
Val Gly Asp Thr Gly Ser Gly Leu Ile Val Phe Phe Pro Gly Phe Pro
50                  55                  60
Gly Ser Ile Val Gly Ala His Tyr Met Leu Gln Ser Asn Gly Asn Tyr
65                  70                  75                  80
Lys Phe Asp Gln Met Leu Leu Thr Ala Gln Asn Leu Pro Ala Ser Tyr
            85                  90                  95
Asn Tyr Cys Arg Leu Val Ser Arg Ser Leu Thr Val Arg Ser Ser Thr
            100                 105                 110
Leu Pro Gly Gly Val Tyr Ala Leu Asn Gly Thr Ile Asn Ala Val Thr
            115                 120                 125
Phe Gln Gly Ser Leu Ser Glu Leu Thr Asp Val Ser Tyr Asn Gly Leu
            130                 135                 140
Met Ser Ala Thr Ala Asn Ile Asn Asp Lys Ile Gly Asn Val Leu Val
145                 150                 155                 160
Gly Glu Gly Val Thr Val Leu Ser Leu Pro Thr Ser Tyr Asp Leu Gly
            165                 170                 175
Tyr Val Arg Leu Gly Asp Pro Ile Pro Ala Ile Gly Leu Asp Pro Lys
            180                 185                 190
Met Val Ala Thr Cys Asp Ser Ser Asp Arg Pro Arg Val Tyr Thr Ile
            195                 200                 205
```

-continued

```
Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Asn Ser Leu
225                 230                 235                 240

Ser Val Gly Gly Glu Leu Val Phe Gln Thr Ser Val Gln Gly Leu Val
                245                 250                 255

Leu Asn Ala Thr Ile Tyr Leu Val Gly Phe Asp Gly Thr Thr Val Thr
                260                 265                 270

Thr Arg Ala Val Ala Ala Gly Asn Gly Leu Thr Ala Gly Thr Asp Asn
        275                 280                 285

Leu Met Pro Phe Asn Leu Val Ile Pro Thr Ser Glu Ile Thr Gln Pro
        290                 295                 300

Val Thr Ser Ile Lys Leu Glu Ile Val Thr Ser Lys Ser Gly Gly Gln
305                 310                 315                 320

Ala Gly Asp Gln Met Ser Trp Leu Ala Ser Gly Asn Leu Ala Val Thr
                325                 330                 335

Ile His Gly Gly Asn Tyr Pro Gly Ala Leu Arg Pro Val Thr Leu Val
                340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
        370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
                420                 425                 430

Asn Ser Pro Leu Lys Ile Ala Gly Ala Phe Gly Phe Lys Asp Ile Ile
        435                 440                 445

Arg Ala Ile Arg Arg Ile Ala Val Pro Val Val Ser Thr Leu Phe Pro
450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
                500                 505                 510

Ala Asp Lys Gly Tyr Glu Val Val Ala Asn Leu Phe Gln Val Pro Gln
        515                 520                 525

Asn Pro Val Val Asp Gly Ile Leu Ala Ser Pro Gly Val Leu Arg Gly
        530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
                565                 570                 575

Ser Lys Met Phe Ala Val Ile Glu Gly Val Arg Glu Asp Leu Gln Pro
                580                 585                 590

Pro Ser Gln Arg Gly Ser Phe Ile Arg Thr Leu Ser Gly His Arg Val
        595                 600                 605

Tyr Gly Tyr Ala Pro Asp Gly Val Leu Pro Leu Glu Thr Gly Arg Asp
        610                 615                 620

Tyr Thr Val Val Pro Ile Asp Asp Val Trp Asp Asp Ser Ile Met Leu
625                 630                 635                 640
```

```
Ser Lys Asp Pro Ile Pro Ile Val Gly Asn Ser Gly Asn Leu Ala
            645                 650                 655

Ile Ala Tyr Met Asp Val Phe Arg Pro Lys Val Pro Ile His Val Ala
            660                 665                 670

Met Thr Gly Ala Leu Asn Ala Cys Gly Glu Val Glu Lys Val Ser Phe
            675                 680                 685

Arg Ser Thr Lys Leu Ala Thr Ala His Arg Leu Gly Leu Lys Leu Ala
            690                 695                 700

Gly Pro Gly Ala Phe Asp Ile Asn Thr Gly Pro Asn Trp Ala Thr Phe
705                 710                 715                 720

Ile Lys Arg Phe Pro His Asn Pro Arg Asp Trp Asp Arg Leu Pro Tyr
            725                 730                 735

Leu Asn Leu Pro Tyr Leu Pro Pro Ser Ala Gly Arg Gln Tyr His Leu
            740                 745                 750

Ala Met Ala Ala Ser Glu Phe Lys Glu Thr Pro Glu Leu Glu Ser Ala
            755                 760                 765

Val Arg Ala Met Glu Ala Ala Ala Asp Val Asp Pro Leu Phe Gln Ser
            770                 775                 780

Ala Leu Ser Val Phe Met Trp Leu Glu Glu Asn Gly Ile Val Thr Asp
785                 790                 795                 800

Met Ala Asn Phe Ala Leu Ser Asp Pro Asn Ala His Arg Met Arg Asn
            805                 810                 815

Phe Leu Ala Asn Ala Pro Gln Ala Gly Ser Lys Ser Gln Arg Ala Lys
            820                 825                 830

Tyr Gly Thr Ala Gly Tyr Gly Val Glu Ala Arg Gly Pro Thr Pro Glu
            835                 840                 845

Glu Ala Gln Arg Glu Lys Asp Thr Arg Ile Ser Lys Lys Met Glu Ala
850                 855                 860

Met Gly Ile Tyr Phe Ala Thr Pro Glu Trp Val Ala Leu Asn Gly His
865                 870                 875                 880

Arg Gly Pro Ser Pro Gly Gln Leu Lys Tyr Trp Gln Asn Thr Arg Glu
            885                 890                 895

Ile Pro Asp Pro Asn Glu Asp Tyr Leu Asp Tyr Val His Ala Glu Lys
            900                 905                 910

Ser Arg Leu Ala Ser Glu Glu Gln Ile Leu Arg Ala Ala Thr Ser Ile
            915                 920                 925

Tyr Gly Ala Pro Gly Gln Ala Glu Pro Pro Gln Ala Phe Ile Asp Glu
            930                 935                 940

Val Ala Lys Val Tyr Glu Ile Asn His Gly Arg Gly Pro Asn Gln Glu
945                 950                 955                 960

Gln Met Lys Asp Leu Leu Thr Ala Met Glu Met Lys His Arg Asn
            965                 970                 975

Pro Arg Arg Ala Pro Pro Lys Pro Lys Pro Lys Pro Asn Ala Pro Ser
            980                 985                 990

Gln Arg Pro Gly Arg Leu Gly Arg Trp Ile Arg Thr Val Ser Asp
            995                 1000                1005

Glu Asp Leu Glu
    1010

(2) INFORMATION FOR SEQ ID NO:10:

(i) SEQUENCE CHARACTERISTICS:
        (A) LENGTH: 1012 amino acids
        (B) TYPE: amino acid
        (C) STRANDEDNESS:
```

(D) TOPOLOGY: unknown (ii) MOLECULE TYPE: protein (vi) ORIGINAL SOURCE:
    (A) ORGANISM: Infectious bursal disease virus
    (B) STRAIN: OH (xi) SEQUENCE DESCRIPTION: SEQ ID NO:10:

```
Met Thr Asn Leu Met Asp His Thr Gln Gln Ile Val Pro Phe Ile Arg
  1               5                  10                  15

Ser Leu Leu Met Pro Thr Thr Gly Pro Ala Ser Ile Pro Asp Asp Thr
                 20                  25                  30

Leu Glu Lys His Thr Leu Arg Ser Glu Thr Ser Thr Tyr Asn Leu Thr
             35                  40                  45

Val Gly Asp Thr Gly Ser Gly Leu Ile Val Phe Phe Pro Gly Phe Pro
 50                  55                  60

Gly Ser Val Val Gly Ala His Tyr Thr Leu Gln Ser Asn Gly Ser Tyr
 65                  70                  75                  80

Gln Phe Asp Gln Met Leu Leu Thr Ala Gln Asn Leu Pro Val Ser Tyr
                 85                  90                  95

Asn Tyr Cys Arg Leu Val Ser Arg Ser Leu Thr Val Arg Ser Ser Thr
                100                 105                 110

Leu Pro Gly Gly Val Tyr Ala Leu Asn Gly Thr Ile Asn Ala Val Thr
            115                 120                 125

Phe Gln Gly Ser Leu Ser Glu Leu Thr Asp Tyr Ser Tyr Asn Gly Leu
130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Ser
                165                 170                 175

Tyr Val Arg Leu Gly Asp Pro Ile Pro Ala Ala Gly Leu Asp Pro Lys
                180                 185                 190

Leu Met Ala Thr Cys Asp Ser Ser Asp Arg Pro Arg Val Tyr Thr Val
            195                 200                 205

Thr Ala Ala Asp Glu Tyr Gln Phe Ser Ser Gln Leu Ile Pro Ser Gly
210                 215                 220

Val Lys Thr Thr Leu Phe Thr Ala Asn Ile Asp Ala Leu Thr Ser Leu
225                 230                 235                 240

Ser Val Gly Gly Glu Leu Ile Phe Ser Gln Val Thr Ile His Ser Ile
                245                 250                 255

Glu Val Asp Val Thr Ile Tyr Phe Ile Gly Phe Asp Gly Thr Glu Val
                260                 265                 270

Thr Val Lys Ala Val Ala Thr Asp Phe Gly Leu Thr Thr Gly Thr Asn
            275                 280                 285

Asn Leu Val Pro Phe Asn Leu Gly Gly Pro Thr Ser Glu Ile Thr Gln
290                 295                 300

Pro Ile Thr Ser Met Lys Leu Glu Val Val Thr Tyr Lys Arg Gly Gly
305                 310                 315                 320

Thr Ala Gly Asp Pro Ile Ser Trp Thr Val Ser Gly Thr Leu Ala Val
                325                 330                 335

Thr Ile Val Gly Gly Asn Tyr Pro Gly Ala Leu Arg Pro Val Thr Leu
                340                 345                 350

Val Ala Tyr Glu Arg Val Ala Ala Gly Ser Val Thr Val Ala Gly
            355                 360                 365

Val Ser Asn Phe Glu Leu Ile Pro Asn Pro Glu Leu Ala Lys Asn Leu
```

-continued

```
            370                 375                 380
Val Thr Glu Tyr Gly Arg Phe Asp Pro Gly Ala Met Asn Tyr Thr Lys
385                 390                 395                 400

Leu Ile Leu Ser Glu Arg Asp Arg Leu Gly Ile Lys Thr Val Trp Pro
                405                 410                 415

Thr Arg Glu Tyr Thr Asp Phe Arg Glu Tyr Phe Met Glu Val Ala Asp
                420                 425                 430

Leu Asn Ser Pro Leu Lys Ile Ala Gly Ala Phe Gly Phe Lys Asp Ile
                435                 440                 445

Ile Arg Ala Ile Arg Lys Ile Ala Val Pro Val Val Ser Thr Leu Phe
450                 455                 460

Pro Pro Ala Ala Pro Leu Ala His Ala Asn Arg Glu Gly Val Asp Tyr
465                 470                 475                 480

Leu Leu Gly Asp Glu Ala Gln Ala Ala Ser Gly Thr Ala Arg Gly Ala
                485                 490                 495

Ser Gly Lys Ala Arg Ala Ala Ser Gly Arg Ile Arg Gln Leu Thr Leu
                500                 505                 510

Ala Ala Asp Lys Gly Tyr Glu Val Val Ala Asn Met Phe Gln Val Pro
                515                 520                 525

Gln Asn Pro Ile Val Asp Gly Ile Leu Ala Ser Pro Gly Ile Leu Arg
530                 535                 540

Gly Ala His Asn Leu Asp Cys Val Ser Lys Glu Gly Ala Thr Leu Phe
545                 550                 555                 560

Pro Val Val Ile Thr Thr Leu Glu Asp Glu Leu Thr Pro Lys Ala Leu
                565                 570                 575

Asn Ser Lys Met Phe Ala Val Ile Glu Gly Ala Arg Glu Asp Leu Gln
                580                 585                 590

Pro Pro Ser Gln Arg Gly Ser Phe Ile Arg Thr Leu Ser Gly His Arg
                595                 600                 605

Val Tyr Gly Tyr Ala Pro Asp Gly Val Leu Pro Leu Glu Thr Gly Arg
610                 615                 620

Asp Tyr Thr Val Pro Ile Asp Asp Val Trp Asp Ser Ile Met
625                 630                 635                 640

Leu Ser Gln Asp Pro Ile Pro Pro Ile Val Gly Asn Ser Gly Asn Leu
                645                 650                 655

Ala Ile Ala Tyr Met Asp Val Phe Arg Pro Lys Val Pro Ile His Val
                660                 665                 670

Ala Met Thr Gly Ala Leu Asn Ala Ser Glu Ile Glu Ser Val Ser Phe
                675                 680                 685

Arg Ser Thr Lys Leu Ala Thr Ala His Arg Leu Gly Met Lys Leu Ala
                690                 695                 700

Gly Pro Gly Asp Tyr Asp Ile Asn Thr Gly Pro Asn Trp Ala Thr Phe
705                 710                 715                 720

Ile Lys Arg Phe Pro His Asn Pro Arg Gly Trp Asp Arg Leu Pro Tyr
                725                 730                 735

Leu Asn Leu Pro Tyr Leu Pro Thr Ala Gly Arg Gln Phe His Leu
                740                 745                 750

Ala Leu Ala Ala Ser Glu Phe Lys Glu Thr Pro Glu Leu Glu Asp Ala
                755                 760                 765

Val Arg Ala Met Asp Ala Ala Asn Ala Asp Pro Leu Phe Arg Ser
                770                 775                 780

Ala Leu Gln Val Phe Met Trp Leu Glu Glu Asn Gly Ile Val Thr Asp
785                 790                 795                 800
```

```
Met Ala Asn Phe Ala Leu Ser Asp Pro Asn Ala His Arg Met Lys Asn
                805                 810                 815

Phe Leu Ala Asn Ala Pro Gln Ala Gly Ser Lys Ser Gln Arg Ala Lys
            820                 825                 830

Tyr Gly Thr Ala Gly Tyr Val Glu Ala Arg Gly Pro Thr Pro Glu
        835                 840                 845

Glu Ala Gln Arg Ala Lys Asp Ala Arg Ile Ser Lys Lys Met Glu Thr
    850                 855                 860

Met Gly Ile Tyr Phe Ala Thr Pro Glu Trp Val Ala Leu Asn Gly His
865                 870                 875                 880

Arg Gly Pro Ser Pro Gly Gln Leu Lys Tyr Trp Gln Asn Thr Arg Glu
                885                 890                 895

Ile Pro Glu Pro Asn Glu Asp Tyr Pro Asp Tyr Val His Ala Glu Lys
            900                 905                 910

Ser Arg Leu Ala Ser Glu Glu Gln Ile Leu Arg Ala Ala Thr Ser Ile
        915                 920                 925

Tyr Gly Ala Pro Gly Gln Ala Glu Pro Pro Gln Ala Phe Ile Asp Glu
    930                 935                 940

Val Ala Arg Val Tyr Glu Thr Asn His Gly Arg Val Pro Asn Gln Glu
945                 950                 955                 960

Gln Met Lys Asp Leu Leu Thr Ala Met Glu Met Lys His Arg Asn
                965                 970                 975

Pro Arg Arg Ala Pro Pro Lys Pro Lys Pro Lys Pro Asn Ala Pro Ser
            980                 985                 990

Gln Arg Pro Pro Gly Arg Leu Gly Arg Trp Ile Arg Thr Val Ser Asp
        995                 1000                1005

Glu Asp Leu Glu
    1010

(2) INFORMATION FOR SEQ ID NO:11:

(i) SEQUENCE CHARACTERISTICS:
        (A) LENGTH: 3230 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 114..3149

(xi) SEQUENCE DESCRIPTION: SEQ ID NO:11:

CCCCGGGGGA GTCACCCGGG GACAGGCCGT CAAGGCCTTG TTCCAGGATG GAACTCCCCC      60

TTCTACAATG CTATCATTGA TGGTTAGTAG AGATCGGACA AACGATCGCA GCG ATG        116
                                                         Met
                                                           1

ACA AAC CTG CAA GAT CAA ACC CAA CAG ATT GTT CCG TTC ATA CGG AGC      164
Thr Asn Leu Gln Asp Gln Thr Gln Gln Ile Val Pro Phe Ile Arg Ser
        5                   10                  15

CTT CTG ATG CCA ACA ACC GGA CCG GCG TCC ATT CCG GAC GAC ACC CTG      212
Leu Leu Met Pro Thr Thr Gly Pro Ala Ser Ile Pro Asp Asp Thr Leu
    20                  25                  30

GAG AAG CAC ACT CTC AGG TCA GAG ACC TCG ACC TAC AAT TTG ACT GTG      260
Glu Lys His Thr Leu Arg Ser Glu Thr Ser Thr Tyr Asn Leu Thr Val
35                  40                  45

GGG GAC ACA GGG TCA GGG CTA ATT GTC TTT TTC CCT GGA TTC CCT GGC      308
Gly Asp Thr Gly Ser Gly Leu Ile Val Phe Phe Pro Gly Phe Pro Gly
50                  55                  60                  65
```

```
TCA ATT GTG GGT GCT CAC TAC ACA CTG CAG AGC AAT GGG AAC TAC AAG    356
Ser Ile Val Gly Ala His Tyr Thr Leu Gln Ser Asn Gly Asn Tyr Lys
            70                  75                  80

TTC GAT CAG ATG CTC CTG ACT GCC CAG AAC CTA CCG GCC AGC TAC AAC    404
Phe Asp Gln Met Leu Leu Thr Ala Gln Asn Leu Pro Ala Ser Tyr Asn
        85                  90                  95

TAC TGC AGG CTA GTG AGT CGG AGT CTC ACA GTA AGG TCA AGC ACA CTC    452
Tyr Cys Arg Leu Val Ser Arg Ser Leu Thr Val Arg Ser Ser Thr Leu
                100                 105                 110

CCT GGT GGC GTT TAT GCA CTA AAC GGC ACC ATA AAC GCC GTG ACC TTC    500
Pro Gly Gly Val Tyr Ala Leu Asn Gly Thr Ile Asn Ala Val Thr Phe
        115                 120                 125

CAA GGA AGC CTG AGT GAA CTG ACA GAT GTT AGC TAC AAT GGG TTG ATG    548
Gln Gly Ser Leu Ser Glu Leu Thr Asp Val Ser Tyr Asn Gly Leu Met
130                 135                 140                 145

TCT GCA ACA GCC AAC ATC AAC GAC AAA ATT GGG AAC GTC CTA GTA GGG    596
Ser Ala Thr Ala Asn Ile Asn Asp Lys Ile Gly Asn Val Leu Val Gly
                150                 155                 160

GAA GGG GTT ACT GTC CTC AGC TTA CCC ACA TCA TAT GAT CTT GGG TAT    644
Glu Gly Val Thr Val Leu Ser Leu Pro Thr Ser Tyr Asp Leu Gly Tyr
            165                 170                 175

GTG AGG CTT GGT GAC CCC ATA CCC GCT ATA GGG CTT GAC CCA AAA ATG    692
Val Arg Leu Gly Asp Pro Ile Pro Ala Ile Gly Leu Asp Pro Lys Met
        180                 185                 190

GTA GCA ACA TGT GAC AGC AGT GAC AGG CCC AGA GTC TAC ACC ATA ACT    740
Val Ala Thr Cys Asp Ser Ser Asp Arg Pro Arg Val Tyr Thr Ile Thr
    195                 200                 205

GCA GCT GAT GAT TAC CAA TTC TCA TCA CAG TAC CAA ACA GGT GGG GTA    788
Ala Ala Asp Asp Tyr Gln Phe Ser Ser Gln Tyr Gln Thr Gly Gly Val
210                 215                 220                 225

ACA ATC ACC CTG TTC TCA GCC AAC ATT GAT GCC ATC ACA AGC CTC AGC    836
Thr Ile Thr Leu Phe Ser Ala Asn Ile Asp Ala Ile Thr Ser Leu Ser
                230                 235                 240

GTT GGG GGA GAG CTC GTG TTT AAA ACA AGC GTC CAC AGC CTT GTA CTG    884
Val Gly Gly Glu Leu Val Phe Lys Thr Ser Val His Ser Leu Val Leu
            245                 250                 255

GGC GCC ACC ATC TAC CTT ATA GGC TTT GAT GGG TCT GCG GTA ATC ACT    932
Gly Ala Thr Ile Tyr Leu Ile Gly Phe Asp Gly Ser Ala Val Ile Thr
        260                 265                 270

AGA GCT GTG GCC GCA AAC AAT GGG CTG ACG ACC GGC ACC GAC AAT CTT    980
Arg Ala Val Ala Ala Asn Asn Gly Leu Thr Thr Gly Thr Asp Asn Leu
275                 280                 285

ATG CCA TTC AAT CTT GTG ATT CCA ACC AAC GAG ATA ACC CAG CCA ATC   1028
Met Pro Phe Asn Leu Val Ile Pro Thr Asn Glu Ile Thr Gln Pro Ile
290                 295                 300                 305

ACA TCC ATC AAA CTG GAG ATA GTG ACC TCC AAA AGT GGT GGT CAG GAA   1076
Thr Ser Ile Lys Leu Glu Ile Val Thr Ser Lys Ser Gly Gly Gln Glu
                310                 315                 320

GGG GAC CAG ATG TCA TGG TCG GCA AGT GGG AGC CTA GCA GTG ACG ATT   1124
Gly Asp Gln Met Ser Trp Ser Ala Ser Gly Ser Leu Ala Val Thr Ile
            325                 330                 335

CAT GGT GGC AAC TAT CCA GGG GCC CTC CGT CCC GTC ACA CTA GTA GCC   1172
His Gly Gly Asn Tyr Pro Gly Ala Leu Arg Pro Val Thr Leu Val Ala
        340                 345                 350

TAC GAA AGA GTG GCA ACA GGA TCT GTC GTT ACG GTC GCT GGG GTG AGC   1220
Tyr Glu Arg Val Ala Thr Gly Ser Val Val Thr Val Ala Gly Val Ser
    355                 360                 365

AAC TTC GAG CTG ATC CCA AAT CCT GAA CTA GCA AAG AAC CTG GTT ACA   1268
Asn Phe Glu Leu Ile Pro Asn Pro Glu Leu Ala Lys Asn Leu Val Thr
370                 375                 380                 385
```

```
GAA TAC GGC CGA TTT GAC CCA GGA GCC ATG AAC TAC ACA AAA TTG ATA      1316
Glu Tyr Gly Arg Phe Asp Pro Gly Ala Met Asn Tyr Thr Lys Leu Ile
                390                 395                 400

CTG AGT GAG AGG GAC CGC CTT GGC ATC AAG ACA GTC TGG CCG ACA AGG      1364
Leu Ser Glu Arg Asp Arg Leu Gly Ile Lys Thr Val Trp Pro Thr Arg
            405                 410                 415

GAG TAC ACC GAC TTT CGT GAG TAC TTC ATG GAG GTG GCC GAC CTC AGC      1412
Glu Tyr Thr Asp Phe Arg Glu Tyr Phe Met Glu Val Ala Asp Leu Ser
                420                 425                 430

TCT CCC CTG AAG ATT GCA GGA GCA TTT GGC TTC AAA GAC ATA ATC CGG      1460
Ser Pro Leu Lys Ile Ala Gly Ala Phe Gly Phe Lys Asp Ile Ile Arg
            435                 440                 445

GCC ATA AGG AGG ATA GCT GTG CCG GTG GTC TCC ACA TTG TTC CCA CCT      1508
Ala Ile Arg Arg Ile Ala Val Pro Val Val Ser Thr Leu Phe Pro Pro
450                 455                 460                 465

GCC GCT CCC CTG GCC CAT GCA ATT GGG GAA GGT GTA GAC TAC CTG CTG      1556
Ala Ala Pro Leu Ala His Ala Ile Gly Glu Gly Val Asp Tyr Leu Leu
                470                 475                 480

GGT GAT GAG GCA CAG GCT GCT TCA GGA ACT GCT CGA GCC GCG TCA GGA      1604
Gly Asp Glu Ala Gln Ala Ala Ser Gly Thr Ala Arg Ala Ala Ser Gly
            485                 490                 495

AAA GCA AGG GCT GCC TCA GGC CGC ATA AGG CAG CTG ACT CTC GCC GCC      1652
Lys Ala Arg Ala Ala Ser Gly Arg Ile Arg Gln Leu Thr Leu Ala Ala
                500                 505                 510

GAC AAG GGG TAC GAG GTA GTC GCG AAT CTA TTC CAG GTG CCC CAG AAT      1700
Asp Lys Gly Tyr Glu Val Val Ala Asn Leu Phe Gln Val Pro Gln Asn
            515                 520                 525

CCC GTA GTC GAC GGG ATT CTT GCT TCA CCC GGG ATA CTC CGC GGT GCA      1748
Pro Val Val Asp Gly Ile Leu Ala Ser Pro Gly Ile Leu Arg Gly Ala
530                 535                 540                 545

CAC AAC CTC GAC TGC GTG TTA AGA GAG GGC GCC ACG CTA TTC CCT GTG      1796
His Asn Leu Asp Cys Val Leu Arg Glu Gly Ala Thr Leu Phe Pro Val
                550                 555                 560

GTC ATC ACG ACA GTG GAA GAC GCC ATG ACA CCC AAA GCA CTA AAC AGC      1844
Val Ile Thr Thr Val Glu Asp Ala Met Thr Pro Lys Ala Leu Asn Ser
            565                 570                 575

AAA ATG TTT GCT GTC ATT GAA GGC GTG CGA GAG GAC CTC CAA CCT CCA      1892
Lys Met Phe Ala Val Ile Glu Gly Val Arg Glu Asp Leu Gln Pro Pro
                580                 585                 590

TCT CAA AGA GGA TCC TTC ATA CGA ACT CTC TCC GGA CAC AGA GTC TAT      1940
Ser Gln Arg Gly Ser Phe Ile Arg Thr Leu Ser Gly His Arg Val Tyr
            595                 600                 605

GGA TAT GCT CCA GAT GGG GTA CTT CCA CTG GAG ACT GGG AGA GAC TAC      1988
Gly Tyr Ala Pro Asp Gly Val Leu Pro Leu Glu Thr Gly Arg Asp Tyr
610                 615                 620                 625

ACC GTT GTC CCA ATA GAT GAT GTC TGG GAC GAC AGC ATT ATG CTG TCC      2036
Thr Val Val Pro Ile Asp Asp Val Trp Asp Asp Ser Ile Met Leu Ser
                630                 635                 640

AAA GAC CCC ATA CCT CCT ATT GTG GGA AAC AGT GGA AAC CTA GCC ATA      2084
Lys Asp Pro Ile Pro Pro Ile Val Gly Asn Ser Gly Asn Leu Ala Ile
            645                 650                 655

GCT TAC ATG GAT GTG TTT CGA CCC AAA GTC CCC ATC CAT GTG GCC ATG      2132
Ala Tyr Met Asp Val Phe Arg Pro Lys Val Pro Ile His Val Ala Met
                660                 665                 670

ACG GGA GCC CTC AAC GCT TGT GGC GAG ATT GAG AAA ATA AGC TTT AGA      2180
Thr Gly Ala Leu Asn Ala Cys Gly Glu Ile Glu Lys Ile Ser Phe Arg
            675                 680                 685

AGC ACC AAG CTC GCC ACC GCA CAC CGG CTT GGC CTC AAG TTG GCT GGT      2228
Ser Thr Lys Leu Ala Thr Ala His Arg Leu Gly Leu Lys Leu Ala Gly
690                 695                 700                 705
```

```
CCC GGA GCA TTT GAT GTA AAC ACC GGG CCC AAC TGG GCA ACG TTC ATC      2276
Pro Gly Ala Phe Asp Val Asn Thr Gly Pro Asn Trp Ala Thr Phe Ile
                710                 715                 720

AAA CGT TTC CCT CAC AAT CCA CGC GAC TGG GAC AGG CTC CCC TAC CTC      2324
Lys Arg Phe Pro His Asn Pro Arg Asp Trp Asp Arg Leu Pro Tyr Leu
            725                 730                 735

AAC CTT CCA TAC CTT CCA CCC AAT GCA GGA CGC CAG TAC CAC CTC GCC      2372
Asn Leu Pro Tyr Leu Pro Pro Asn Ala Gly Arg Gln Tyr His Leu Ala
        740                 745                 750

ATG GCC GCA TCA GAG TTC AAG GAG ACC CCT GAA CTC GAG AGC GCC GTC      2420
Met Ala Ala Ser Glu Phe Lys Glu Thr Pro Glu Leu Glu Ser Ala Val
    755                 760                 765

AGG GCC ATG GAA GCA GCA GCC AGT GTA GAC CCA CTG TTC CAA TCT GCA      2468
Arg Ala Met Glu Ala Ala Ala Ser Val Asp Pro Leu Phe Gln Ser Ala
770                 775                 780                 785

CTC AGT GTG TTC ATG TGG CTG GAA GAG AAT GGG ATT GTG ACT GAC ATG      2516
Leu Ser Val Phe Met Trp Leu Glu Glu Asn Gly Ile Val Thr Asp Met
                790                 795                 800

GCC AAC TTC GCA CTC AGC GAC CCG AAC GCC CAT CGG ATG CGA AAC TTT      2564
Ala Asn Phe Ala Leu Ser Asp Pro Asn Ala His Arg Met Arg Asn Phe
            805                 810                 815

CTT GCA AAC GCA CCA CAA GCA GGT AGC AAG TCT CAA AGG GCC AAA TAC      2612
Leu Ala Asn Ala Pro Gln Ala Gly Ser Lys Ser Gln Arg Ala Lys Tyr
        820                 825                 830

GGG ACA GCA GGC TAC GGA GTG GAG GCC CGG GGC CCC ACA CCA GAA GAA      2660
Gly Thr Ala Gly Tyr Gly Val Glu Ala Arg Gly Pro Thr Pro Glu Glu
    835                 840                 845

GCA CAG AGG GAA AAA GAC ACA CGG ATC TCA AAG AAG ATG GAG ACC ATG      2708
Ala Gln Arg Glu Lys Asp Thr Arg Ile Ser Lys Lys Met Glu Thr Met
850                 855                 860                 865

GGC ATC TAC TTT GCA ACA CCA GAA TGG GTA GCA CTC AAT GGG CAC CGA      2756
Gly Ile Tyr Phe Ala Thr Pro Glu Trp Val Ala Leu Asn Gly His Arg
                870                 875                 880

GGG CCA AGC CCC GGC CAG CTA AAG TAC TGG CAG AAC ACA CGA GAA ATA      2804
Gly Pro Ser Pro Gly Gln Leu Lys Tyr Trp Gln Asn Thr Arg Glu Ile
            885                 890                 895

CCG GAC CCA AAC GAG GAC TAT CTA GAC TAC GTG CAT GCA GAG AAG AGC      2852
Pro Asp Pro Asn Glu Asp Tyr Leu Asp Tyr Val His Ala Glu Lys Ser
        900                 905                 910

CGG TTG GCA TCA GAA GAA CAA ATC CTA AGG GCA GCT ACG TCG ATC TAC      2900
Arg Leu Ala Ser Glu Glu Gln Ile Leu Arg Ala Ala Thr Ser Ile Tyr
    915                 920                 925

GGG GCT CCA GGA CAG GCA GAG CCA CCC CAA GCT TTC ATA GAC GAA GTT      2948
Gly Ala Pro Gly Gln Ala Glu Pro Pro Gln Ala Phe Ile Asp Glu Val
930                 935                 940                 945

GCC AAA GTC TAT GAA ATC AAC CAT GGA CGT GGC CCA AAC CAA GAA CAG      2996
Ala Lys Val Tyr Glu Ile Asn His Gly Arg Gly Pro Asn Gln Glu Gln
                950                 955                 960

ATG AAA GAT CTG CTC TTG ACT GCG ATG GAG ATG AAG CAT CGC AAT CCC      3044
Met Lys Asp Leu Leu Leu Thr Ala Met Glu Met Lys His Arg Asn Pro
            965                 970                 975

AGG CGG GCT CCA CCA AAG CCC AAG CCA AGA CCC AAC GCT CCA ACG CAG      3092
Arg Arg Ala Pro Pro Lys Pro Lys Pro Arg Pro Asn Ala Pro Thr Gln
        980                 985                 990

AGA CCC CCT GGT CGG CTG GGC CGC TGG ATC AGG ACT GTC TCT GAT GAG      3140
Arg Pro Pro Gly Arg Leu Gly Arg Trp Ile Arg Thr Val Ser Asp Glu
    995                 1000                1005

GAC CTT GAG TGAGGCTCCT GGGAGTCTCC CGACACCACC CGCGCAGGCG             3189
Asp Leu Glu
1010
```

```
TGGACACCAA TTCGGCCTTA CAACATCCCA AATTGGATCC G                              3230
```

(2) INFORMATION FOR SEQ ID NO:12:

(i) SEQUENCE CHARACTERISTICS:
        (A) LENGTH: 1012 amino acids
        (B) TYPE: amino acid
        (D) TOPOLOGY: linear (ii) MOLECULE TYPE: protein (xi) SEQUENCE DESCRIPTION: SEQ ID NO:12:

```
Met Thr Asn Leu Gln Asp Gln Thr Gln Gln Ile Val Pro Phe Ile Arg
  1               5                  10                  15

Ser Leu Leu Met Pro Thr Thr Gly Pro Ala Ser Ile Pro Asp Asp Thr
             20                  25                  30

Leu Glu Lys His Thr Leu Arg Ser Glu Thr Ser Thr Tyr Asn Leu Thr
         35                  40                  45

Val Gly Asp Thr Gly Ser Gly Leu Ile Val Phe Phe Pro Gly Phe Pro
 50                  55                  60

Gly Ser Ile Val Gly Ala His Tyr Thr Leu Gln Ser Asn Gly Asn Tyr
 65                  70                  75                  80

Lys Phe Asp Gln Met Leu Leu Thr Ala Gln Asn Leu Pro Ala Ser Tyr
             85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
            165                 170                 175

Tyr Val Arg Leu Gly Asp Pro Ile Pro Ala Ile Gly Leu Asp Pro Lys
        180                 185                 190

Met Val Ala Thr Cys Asp Ser Ser Asp Arg Pro Arg Val Tyr Thr Ile
    195                 200                 205

Thr Ala Ala Asp Asp Tyr Gln Phe Ser Ser Gln Tyr Gln Thr Gly Gly
210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val His Ser Leu Val
            245                 250                 255

Leu Gly Ala Thr Ile Tyr Leu Ile Gly Phe Asp Gly Ser Ala Val Ile
        260                 265                 270

Thr Arg Ala Val Ala Ala Asn Asn Gly Leu Thr Thr Gly Thr Asp Asn
    275                 280                 285

Leu Met Pro Phe Asn Leu Val Ile Pro Thr Asn Glu Ile Thr Gln Pro
290                 295                 300

Ile Thr Ser Ile Lys Leu Glu Ile Val Thr Ser Lys Ser Gly Gly Gln
305                 310                 315                 320

Glu Gly Asp Gln Met Ser Trp Ser Ala Ser Gly Ser Leu Ala Val Thr
            325                 330                 335

Ile His Gly Gly Asn Tyr Pro Gly Ala Leu Arg Pro Val Thr Leu Val
        340                 345                 350
```

```
Ala Tyr Glu Arg Val Ala Thr Gly Ser Val Val Thr Val Ala Gly Val
            355                 360                 365

Ser Asn Phe Glu Leu Ile Pro Asn Pro Glu Leu Ala Lys Asn Leu Val
        370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Ser Ser Pro Leu Lys Ile Ala Gly Ala Phe Gly Phe Lys Asp Ile Ile
            435                 440                 445

Arg Ala Ile Arg Arg Ile Ala Val Pro Val Val Ser Thr Leu Phe Pro
            450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
                500                 505                 510

Ala Asp Lys Gly Tyr Glu Val Val Ala Asn Leu Phe Gln Val Pro Gln
            515                 520                 525

Asn Pro Val Val Asp Gly Ile Leu Ala Ser Pro Gly Ile Leu Arg Gly
            530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
                565                 570                 575

Ser Lys Met Phe Ala Val Ile Glu Gly Val Arg Glu Asp Leu Gln Pro
            580                 585                 590

Pro Ser Gln Arg Gly Ser Phe Ile Arg Thr Leu Ser Gly His Arg Val
            595                 600                 605

Tyr Gly Tyr Ala Pro Asp Gly Val Leu Pro Leu Glu Thr Gly Arg Asp
            610                 615                 620

Tyr Thr Val Val Pro Ile Asp Asp Val Trp Asp Ser Ile Met Leu
625                 630                 635                 640

Ser Lys Asp Pro Ile Pro Pro Val Gly Asn Ser Gly Asn Leu Ala
                645                 650                 655

Ile Ala Tyr Met Asp Val Phe Arg Pro Lys Val Pro Ile His Val Ala
                660                 665                 670

Met Thr Gly Ala Leu Asn Ala Cys Gly Glu Ile Glu Lys Ile Ser Phe
            675                 680                 685

Arg Ser Thr Lys Leu Ala Thr His Arg Leu Gly Leu Lys Leu Ala
            690                 695                 700

Gly Pro Gly Ala Phe Asp Val Asn Thr Gly Pro Asn Trp Ala Thr Phe
705                 710                 715                 720

Ile Lys Arg Phe Pro His Asn Pro Arg Asp Trp Asp Arg Leu Pro Tyr
                725                 730                 735

Leu Asn Leu Pro Tyr Leu Pro Pro Asn Ala Gly Arg Gln Tyr His Leu
            740                 745                 750

Ala Met Ala Ala Ser Glu Phe Lys Glu Thr Pro Glu Leu Glu Ser Ala
            755                 760                 765

Val Arg Ala Met Glu Ala Ala Ala Ser Val Asp Pro Leu Phe Gln Ser
```

```
                 770                 775                 780
Ala Leu Ser Val Phe Met Trp Leu Glu Glu Asn Gly Ile Val Thr Asp
785                 790                 795                 800

Met Ala Asn Phe Ala Leu Ser Asp Pro Asn Ala His Arg Met Arg Asn
            805                 810                 815

Phe Leu Ala Asn Ala Pro Gln Ala Gly Ser Lys Ser Gln Arg Ala Lys
            820                 825                 830

Tyr Gly Thr Ala Gly Tyr Gly Val Glu Ala Arg Gly Pro Thr Pro Glu
            835                 840                 845

Glu Ala Gln Arg Glu Lys Asp Thr Arg Ile Ser Lys Lys Met Glu Thr
850                 855                 860

Met Gly Ile Tyr Phe Ala Thr Pro Glu Trp Val Ala Leu Asn Gly His
865                 870                 875                 880

Arg Gly Pro Ser Pro Gly Gln Leu Lys Tyr Trp Gln Asn Thr Arg Glu
            885                 890                 895

Ile Pro Asp Pro Asn Glu Asp Tyr Leu Asp Tyr Val His Ala Glu Lys
            900                 905                 910

Ser Arg Leu Ala Ser Glu Glu Gln Ile Leu Arg Ala Ala Thr Ser Ile
            915                 920                 925

Tyr Gly Ala Pro Gly Gln Ala Glu Pro Pro Gln Ala Phe Ile Asp Glu
            930                 935                 940

Val Ala Lys Val Tyr Glu Ile Asn His Gly Arg Gly Pro Asn Gln Glu
945                 950                 955                 960

Gln Met Lys Asp Leu Leu Leu Thr Ala Met Glu Met Lys His Arg Asn
                965                 970                 975

Pro Arg Arg Ala Pro Pro Lys Pro Lys Pro Arg Pro Asn Ala Pro Thr
            980                 985                 990

Gln Arg Pro Pro Gly Arg Leu Gly Arg Trp Ile Arg Thr Val Ser Asp
            995                 1000                1005

Glu Asp Leu Glu
    1010

(2) INFORMATION FOR SEQ ID NO:13:

(i) SEQUENCE CHARACTERISTICS:
        (A) LENGTH: 3180 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 64..3099

(xi) SEQUENCE DESCRIPTION: SEQ ID NO:13:

GAATTCCTCC TTCTACAACG CTATCATTGA TGGTTAGTAG AGATCAGACA AACGATCGCA       60

GCG ATG ACA AAC CTG CAA GAT CAA ACC CAC CAG ATT GTT CCG TTC ATA      108
    Met Thr Asn Leu Gln Asp Gln Thr His Gln Ile Val Pro Phe Ile
        1015                1020                1025

CGG AGC CTT CTG ATG CCA ACA ACC GGA CCG GCG TCC ATT CCG GAC GAC      156
Arg Ser Leu Leu Met Pro Thr Thr Gly Pro Ala Ser Ile Pro Asp Asp
    1030                1035                1040

ACC CTG GAG AAG CAC ACT CTC AGG TCA GAG ACC TCG ACC TAC AAT TTG      204
Thr Leu Glu Lys His Thr Leu Arg Ser Glu Thr Ser Thr Tyr Asn Leu
    1045                1050                1055

ACT GTG GGG GAC ACA GGG TCA GGG CTA ATT GTC TTT TTC CCT GGA TTC      252
Thr Val Gly Asp Thr Gly Ser Gly Leu Ile Val Phe Phe Pro Gly Phe
```

-continued

```
       1060                1065                1070                1075

CCT GGC TCA ATT GTG GGT GCT CAC TAC ACA CTG CAG AGC AGT GGG AAC        300
Pro Gly Ser Ile Val Gly Ala His Tyr Thr Leu Gln Ser Ser Gly Asn
                 1080                1085                1090

TAC AAG TTC GAT CAG ATG CTC CTG ACT GCC CAG AAC CTA CCG GCC AGC        348
Tyr Lys Phe Asp Gln Met Leu Leu Thr Ala Gln Asn Leu Pro Ala Ser
                 1095                1100                1105

TAC AAC TAC TGC AGG CTA GTG AGT CGG AGT CTC ACA GTA AGG TCA AGC        396
Tyr Asn Tyr Cys Arg Leu Val Ser Arg Ser Leu Thr Val Arg Ser Ser
                 1110                1115                1120

ACA CTC CCT GGT GGC GTT TAT GCA CTA AAC GGC ACC ATA AAC GCC GTG        444
Thr Leu Pro Gly Gly Val Tyr Ala Leu Asn Gly Thr Ile Asn Ala Val
                 1125                1130                1135

ACC TTC CAA GGA AGC CTG AGT GAA CTG ACA GAT GTT AGC TAC AAC GGG        492
Thr Phe Gln Gly Ser Leu Ser Glu Leu Thr Asp Val Ser Tyr Asn Gly
1140                1145                1150                1155

TTG ATG TCT GCA ACA GCC AAC ATC AAC GAC AAA ATT GGG AAC GTC CTA        540
Leu Met Ser Ala Thr Ala Asn Ile Asn Asp Lys Ile Gly Asn Val Leu
                 1160                1165                1170

GTA GGG GAA GGG GTA ACC GTC CTC AGC TTA CCC ACA TCA TAT GAT CTT        588
Val Gly Glu Gly Val Thr Val Leu Ser Leu Pro Thr Ser Tyr Asp Leu
                 1175                1180                1185

GGG TAT GTG AGG CTT GGT GAC CCC ATA CCC GCT ATA GGG CTT GAC CCA        636
Gly Tyr Val Arg Leu Gly Asp Pro Ile Pro Ala Ile Gly Leu Asp Pro
                 1190                1195                1200

AAA ATG GTA GCA ACA TGT GAC AGC AGT GAC AGG CCC AGA GTC TAC ACC        684
Lys Met Val Ala Thr Cys Asp Ser Ser Asp Arg Pro Arg Val Tyr Thr
                 1205                1210                1215

ATA ACT GCA GCC GAT AAT TAC CAA TTC TCA TCA CAG TAC CAA ACA GGT        732
Ile Thr Ala Ala Asp Asn Tyr Gln Phe Ser Ser Gln Tyr Gln Thr Gly
1220                1225                1230                1235

GGG GTA ACA ATC ACA CTG TTC TCA GCC AAC ATT GAT GCC ATC ACA AGT        780
Gly Val Thr Ile Thr Leu Phe Ser Ala Asn Ile Asp Ala Ile Thr Ser
                 1240                1245                1250

CTC AGC GTT GGG GGA GAG CTC GTG TTC AAA ACA AGC GTC CAA AGC CTT        828
Leu Ser Val Gly Gly Glu Leu Val Phe Lys Thr Ser Val Gln Ser Leu
                 1255                1260                1265

GTA CTG GGC GCC ACC ATC TAC CTT ATA GGC TTT GAT GGG ACT GCG GTA        876
Val Leu Gly Ala Thr Ile Tyr Leu Ile Gly Phe Asp Gly Thr Ala Val
                 1270                1275                1280

ATC ACC AGA GCT GTG GCC GCA AAC AAT GGG CTG ACG GCC GGC ATC GAC        924
Ile Thr Arg Ala Val Ala Ala Asn Asn Gly Leu Thr Ala Gly Ile Asp
                 1285                1290                1295

AAT CTT ATG CCA TTC AAT CTT GTG ATT CCA ACC AAT GAG ATA ACC CAG        972
Asn Leu Met Pro Phe Asn Leu Val Ile Pro Thr Asn Glu Ile Thr Gln
1300                1305                1310                1315

CCA ATC ACA TCC ATC ATA CTG GAG ATA GTG ACC TCC AAA AGT GAT GGT       1020
Pro Ile Thr Ser Ile Ile Leu Glu Ile Val Thr Ser Lys Ser Asp Gly
                 1320                1325                1330

CAG GCA GGG GAA CAG ATG TCA TGG TCG GCA AGT GGG AGC CTA GCA GTG       1068
Gln Ala Gly Glu Gln Met Ser Trp Ser Ala Ser Gly Ser Leu Ala Val
                 1335                1340                1345

ACG ATC CAT GGT GGC AAC TAT CCA GGA GCC CTC CGT CCC GTC ACA CTA       1116
Thr Ile His Gly Gly Asn Tyr Pro Gly Ala Leu Arg Pro Val Thr Leu
                 1350                1355                1360

GTG GCC TAC GAA AGA GTG GCA ACA GGA TCT GTC GTT ACG GTC GCT GGG       1164
Val Ala Tyr Glu Arg Val Ala Thr Gly Ser Val Val Thr Val Ala Gly
                 1365                1370                1375

GTG AGC AAC TTC GAG CTG ATC CCA AAT CCT GAA CTA GCA AAG AAC CTG       1212
Val Ser Asn Phe Glu Leu Ile Pro Asn Pro Glu Leu Ala Lys Asn Leu
```

```
                    1380           1385            1390          1395
GTT ACA GAA TAC GGC CGA TTT GAC CCA GGA GCC ATG AAC TAC ACG AAA         1260
Val Thr Glu Tyr Gly Arg Phe Asp Pro Gly Ala Met Asn Tyr Thr Lys
                1400            1405            1410

TTG ATA CTG AGT GAG AGG GAC CAC CTT GGC ATC AAG ACC GTC TGG CCA         1308
Leu Ile Leu Ser Glu Arg Asp His Leu Gly Ile Lys Thr Val Trp Pro
                1415            1420            1425

ACA AGG GAG TAC ACT GAC TTT CGT GAG TAC TTC ATG GAG GTG GCC GAC         1356
Thr Arg Glu Tyr Thr Asp Phe Arg Glu Tyr Phe Met Glu Val Ala Asp
                1430            1435            1440

CTC AAC TCT CCC CTG AAG ATT GCA GGA GCA TTT GGC TTC AAA GAC ATA         1404
Leu Asn Ser Pro Leu Lys Ile Ala Gly Ala Phe Gly Phe Lys Asp Ile
                1445            1450            1455

ATC CGG GCC ATA AGG AGG ATA GCT GTA CCG GTG GTC TCT ACA TTG TTC         1452
Ile Arg Ala Ile Arg Arg Ile Ala Val Pro Val Val Ser Thr Leu Phe
1460            1465            1470            1475

CCA CCT GCC GCT CCT CTA GCC CAT GCA ATT GGG GAA GGT GTA GAC TAC         1500
Pro Pro Ala Ala Pro Leu Ala His Ala Ile Gly Glu Gly Val Asp Tyr
                1480            1485            1490

CTA CTG GGC GAT GAG GCA CAG GCT GCT TCA GGA ACC GCT CGA GCC GCG         1548
Leu Leu Gly Asp Glu Ala Gln Ala Ala Ser Gly Thr Ala Arg Ala Ala
                1495            1500            1505

TCA GGA AAA GCA AGG GCT GCC TCA GGC CGC ATA AGG CAG CTG ACT CTC         1596
Ser Gly Lys Ala Arg Ala Ala Ser Gly Arg Ile Arg Gln Leu Thr Leu
                1510            1515            1520

GCC GCC GAC AAG GGG TAC GAG GTA GTC GCG AAT CTA TTC CAG GTG CCC         1644
Ala Ala Asp Lys Gly Tyr Glu Val Val Ala Asn Leu Phe Gln Val Pro
                1525            1530            1535

CAG AAT CCC GTA GTC GAC GGG ATT CTT GCT TCA CCC GGG ATA CTT CGC         1692
Gln Asn Pro Val Val Asp Gly Ile Leu Ala Ser Pro Gly Ile Leu Arg
1540            1545            1550            1555

GGT GCA CAC AAC CTC GAC TGC GTG CTA AGA GAG GGT GCC ACG CTA TTC         1740
Gly Ala His Asn Leu Asp Cys Val Leu Arg Glu Gly Ala Thr Leu Phe
                1560            1565            1570

CCT GTG GTC ATT ACG ACA GTG GAA GAC GCC ATG ACA CCC AAA GCA CTG         1788
Pro Val Val Ile Thr Thr Val Glu Asp Ala Met Thr Pro Lys Ala Leu
                1575            1580            1585

AAC AGC AAA ATG TTT GCT GTC ATT GAA GGC GTG CGA GAA GAC CTC CAA         1836
Asn Ser Lys Met Phe Ala Val Ile Glu Gly Val Arg Glu Asp Leu Gln
                1590            1595            1600

CCT CCA TCT CAA AGA GGA TCC TTC ATA CGA ACT CTC TCC GGA CAC AGA         1884
Pro Pro Ser Gln Arg Gly Ser Phe Ile Arg Thr Leu Ser Gly His Arg
                1605            1610            1615

GTC TAT GGA TAT GCT CCA GAT GGG GTA CTT CCA CTG GAG ACT GGG AGA         1932
Val Tyr Gly Tyr Ala Pro Asp Gly Val Leu Pro Leu Glu Thr Gly Arg
1620            1625            1630            1635

GAC TAC ACC GTT GTC CCA ATA GAT GAT GTC TGG GAC GAC AGC ATT ATG         1980
Asp Tyr Thr Val Val Pro Ile Asp Asp Val Trp Asp Asp Ser Ile Met
                1640            1645            1650

CTG TCC AAG GAC CCC ATA CCT CCT ATT GTG GGA AAC AGT GGA AAC CTA         2028
Leu Ser Lys Asp Pro Ile Pro Pro Ile Val Gly Asn Ser Gly Asn Leu
                1655            1660            1665

GCC ATA GCT TAC ATG GAT GTG TTT CGA CCC AAA GTC CCC ATC CAT GTG         2076
Ala Ile Ala Tyr Met Asp Val Phe Arg Pro Lys Val Pro Ile His Val
                1670            1675            1680

GCC ATG ACG GGA GCC CTC AAC GCT TGT GGC GAG ATT GAG AAA ATA AGC         2124
Ala Met Thr Gly Ala Leu Asn Ala Cys Gly Glu Ile Glu Lys Ile Ser
                1685            1690            1695

TTC AGA AGC ACC AAG CTC GCC ACC GCA CAC CGG CTT GGC CTC AAG TTG         2172
Phe Arg Ser Thr Lys Leu Ala Thr Ala His Arg Leu Gly Leu Lys Leu
```

-continued

```
        1700              1705              1710              1715

GCT GGT CCC GGA GCA TTC GAT GTA AAC ACC GGG CCC AAC TGG GCA ACG    2220
Ala Gly Pro Gly Ala Phe Asp Val Asn Thr Gly Pro Asn Trp Ala Thr
            1720              1725              1730

TTC ATC AAA CGT TTC CCT CAC AAT CCA CGC GAC TGG GAC AGG CTC CCC    2268
Phe Ile Lys Arg Phe Pro His Asn Pro Arg Asp Trp Asp Arg Leu Pro
        1735              1740              1745

TAC CTC AAC CTT CCA TAC CTT CCA CCC AAT GCA GGA CGC CAG TAC CAC    2316
Tyr Leu Asn Leu Pro Tyr Leu Pro Pro Asn Ala Gly Arg Gln Tyr His
        1750              1755              1760

CTT GCC ATG GCT GCA TCA GAG TTT AAA GAG ACC CCT GAA CTC GAG AGC    2364
Leu Ala Met Ala Ala Ser Glu Phe Lys Glu Thr Pro Glu Leu Glu Ser
        1765              1770              1775

GCC GTC AGA GCC ATG GAA GCA GCA GCC AAT GTG GAC CCA CTG TTC CAA    2412
Ala Val Arg Ala Met Glu Ala Ala Ala Asn Val Asp Pro Leu Phe Gln
1780              1785              1790              1795

TCT GCA CTC AGT GTG TTC ATG TGG CTG GAA GAG AAT GGG ATT GTG GCT    2460
Ser Ala Leu Ser Val Phe Met Trp Leu Glu Glu Asn Gly Ile Val Ala
                1800              1805              1810

GAC ATG GCC AAT TTC GCA CTC AGC GAC CCG AAC GCC CAT CGG ATG CGA    2508
Asp Met Ala Asn Phe Ala Leu Ser Asp Pro Asn Ala His Arg Met Arg
            1815              1820              1825

AAT TTT CTT GCA AAC GCA CCA CAA GCA GGC AGC AAG TCG CAA AGG GCC    2556
Asn Phe Leu Ala Asn Ala Pro Gln Ala Gly Ser Lys Ser Gln Arg Ala
        1830              1835              1840

AAG TAC GGG ACA GCA GGC TAC GGA GTG GAG GCC CGG GGC CCC ACA CCA    2604
Lys Tyr Gly Thr Ala Gly Tyr Gly Val Glu Ala Arg Gly Pro Thr Pro
        1845              1850              1855

GAG GAA GCA CAG AGG GAA AAA GAC ACA CGG ATC TCA AAG AAG ATG GAG    2652
Glu Glu Ala Gln Arg Glu Lys Asp Thr Arg Ile Ser Lys Lys Met Glu
1860              1865              1870              1875

ACC ATG GGC ATC TAC TTT GCA ACA CCA GAA TGG GTA GCA CTC AAT GGG    2700
Thr Met Gly Ile Tyr Phe Ala Thr Pro Glu Trp Val Ala Leu Asn Gly
                1880              1885              1890

CAC CGA GGG CCA AGC CCC GGC CAG CTA AAG TAC TGG CAG AAC ACA CGA    2748
His Arg Gly Pro Ser Pro Gly Gln Leu Lys Tyr Trp Gln Asn Thr Arg
            1895              1900              1905

GAA ATA CCG GAC CCA AAC GAG GAC TAT CTA GAC TAC GTG CAT GCA GAG    2796
Glu Ile Pro Asp Pro Asn Glu Asp Tyr Leu Asp Tyr Val His Ala Glu
            1910              1915              1920

AAG AGC CGG TTG GCA TCA GAA GAA CAA ATC CTA AAG GCA GCT ACG TCG    2844
Lys Ser Arg Leu Ala Ser Glu Glu Gln Ile Leu Lys Ala Ala Thr Ser
        1925              1930              1935

ATC TAC GGG GCT CCA GGA CAG GCA GAG CCA CCC CAA GCT TTC ATA GAC    2892
Ile Tyr Gly Ala Pro Gly Gln Ala Glu Pro Pro Gln Ala Phe Ile Asp
1940              1945              1950              1955

GAA GTT GCC AAA GTC TAT GAA ATC AAC CAT GGA CGT GGC CCT AAC CAA    2940
Glu Val Ala Lys Val Tyr Glu Ile Asn His Gly Arg Gly Pro Asn Gln
                1960              1965              1970

GAA CAG ATG AAA GAT CTG CTC TTG ACT GCA ATG GAG ATG AAG CAT CGC    2988
Glu Gln Met Lys Asp Leu Leu Leu Thr Ala Met Glu Met Lys His Arg
            1975              1980              1985

AAC CCC AGG CGG GCT CCA CCA AAG CCC AAG CCA AAA CCC AAT GCT CCA    3036
Asn Pro Arg Arg Ala Pro Pro Lys Pro Lys Pro Lys Pro Asn Ala Pro
        1990              1995              2000

ACA CAG AGA CCC CCT GGT CGG CTG GGC CGC TGG ATC AGG ACC GTC TCT    3084
Thr Gln Arg Pro Pro Gly Arg Leu Gly Arg Trp Ile Arg Thr Val Ser
        2005              2010              2015

GAT GAG GAC CTT GAG TGAGGCCCCT GGGGGTCTCC CGACACCACC CGCGCAGGCG    3139
Asp Glu Asp Leu Glu
```

2020

TGGACACCAA TTCGGCCTTA CAACATCCCA AATTGGATCC G                3180

(2) INFORMATION FOR SEQ ID NO:14:

(i) SEQUENCE CHARACTERISTICS:
        (A) LENGTH: 1012 amino acids
        (B) TYPE: amino acid
        (D) TOPOLOGY: linear (ii) MOLECULE TYPE: protein (xi) SEQUENCE DESCRIPTION: SEQ ID NO:14:

```
Met Thr Asn Leu Gln Asp Gln Thr His Gln Ile Val Pro Phe Ile Arg
 1               5                  10                  15

Ser Leu Leu Met Pro Thr Thr Gly Pro Ala Ser Ile Pro Asp Asp Thr
                20                  25                  30

Leu Glu Lys His Thr Leu Arg Ser Glu Thr Ser Thr Tyr Asn Leu Thr
            35                  40                  45

Val Gly Asp Thr Gly Ser Gly Leu Ile Val Phe Phe Pro Gly Phe Pro
        50                  55                  60

Gly Ser Ile Val Gly Ala His Tyr Thr Leu Gln Ser Ser Gly Asn Tyr
 65                 70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
        210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asn Asn Gly Leu Thr Ala Gly Ile Asp Asn
        275                 280                 285

Leu Met Pro Phe Asn Leu Val Ile Pro Thr Asn Glu Ile Thr Gln Pro
        290                 295                 300

Ile Thr Ser Ile Ile Leu Glu Ile Val Thr Ser Lys Ser Asp Gly Gln
305                 310                 315                 320

Ala Gly Glu Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
```

-continued

```
            340                 345                 350
Ala Tyr Glu Arg Val Ala Thr Gly Ser Val Val Thr Val Ala Gly Val
            355                 360                 365
Ser Asn Phe Glu Leu Ile Pro Asn Pro Glu Leu Ala Lys Asn Leu Val
    370                 375                 380
Thr Glu Tyr Gly Arg Phe Asp Pro Gly Ala Met Asn Tyr Thr Lys Leu
385                 390                 395                 400
Ile Leu Ser Glu Arg Asp His Leu Gly Ile Lys Thr Val Trp Pro Thr
                405                 410                 415
Arg Glu Tyr Thr Asp Phe Arg Glu Tyr Phe Met Glu Val Ala Asp Leu
            420                 425                 430
Asn Ser Pro Leu Lys Ile Ala Gly Ala Phe Gly Phe Lys Asp Ile Ile
        435                 440                 445
Arg Ala Ile Arg Arg Ile Ala Val Pro Val Val Ser Thr Leu Phe Pro
    450                 455                 460
Pro Ala Ala Pro Leu Ala His Ala Ile Gly Glu Gly Val Asp Tyr Leu
465                 470                 475                 480
Leu Gly Asp Glu Ala Gln Ala Ala Ser Gly Thr Ala Arg Ala Ala Ser
                485                 490                 495
Gly Lys Ala Arg Ala Ala Ser Gly Arg Ile Arg Gln Leu Thr Leu Ala
            500                 505                 510
Ala Asp Lys Gly Tyr Glu Val Val Ala Asn Leu Phe Gln Val Pro Gln
        515                 520                 525
Asn Pro Val Val Asp Gly Ile Leu Ala Ser Pro Gly Ile Leu Arg Gly
    530                 535                 540
Ala His Asn Leu Asp Cys Val Leu Arg Glu Gly Ala Thr Leu Phe Pro
545                 550                 555                 560
Val Val Ile Thr Thr Val Glu Asp Ala Met Thr Pro Lys Ala Leu Asn
                565                 570                 575
Ser Lys Met Phe Ala Val Ile Glu Gly Val Arg Glu Asp Leu Gln Pro
            580                 585                 590
Pro Ser Gln Arg Gly Ser Phe Ile Arg Thr Leu Ser Gly His Arg Val
        595                 600                 605
Tyr Gly Tyr Ala Pro Asp Gly Val Leu Pro Leu Glu Thr Gly Arg Asp
    610                 615                 620
Tyr Thr Val Val Pro Ile Asp Asp Val Trp Asp Ser Ile Met Leu
625                 630                 635                 640
Ser Lys Asp Pro Ile Pro Pro Ile Val Gly Asn Ser Gly Asn Leu Ala
                645                 650                 655
Ile Ala Tyr Met Asp Val Phe Arg Pro Lys Val Pro Ile His Val Ala
            660                 665                 670
Met Thr Gly Ala Leu Asn Ala Cys Gly Glu Ile Glu Lys Ile Ser Phe
        675                 680                 685
Arg Ser Thr Lys Leu Ala Thr Ala His Arg Leu Gly Leu Lys Leu Ala
    690                 695                 700
Gly Pro Gly Ala Phe Asp Val Asn Thr Gly Pro Asn Trp Ala Thr Phe
705                 710                 715                 720
Ile Lys Arg Phe Pro His Asn Pro Arg Asp Trp Asp Arg Leu Pro Tyr
                725                 730                 735
Leu Asn Leu Pro Tyr Leu Pro Pro Asn Ala Gly Arg Gln Tyr His Leu
            740                 745                 750
Ala Met Ala Ala Ser Glu Phe Lys Glu Thr Pro Glu Leu Glu Ser Ala
        755                 760                 765
```

```
Val Arg Ala Met Glu Ala Ala Ala Asn Val Asp Pro Leu Phe Gln Ser
    770             775             780

Ala Leu Ser Val Phe Met Trp Leu Glu Glu Asn Gly Ile Val Ala Asp
785             790             795                         800

Met Ala Asn Phe Ala Leu Ser Asp Pro Asn Ala His Arg Met Arg Asn
            805             810              815

Phe Leu Ala Asn Ala Pro Gln Ala Gly Ser Lys Ser Gln Arg Ala Lys
            820             825             830

Tyr Gly Thr Ala Gly Tyr Gly Val Glu Ala Arg Gly Pro Thr Pro Glu
            835             840             845

Glu Ala Gln Arg Glu Lys Asp Thr Arg Ile Ser Lys Lys Met Glu Thr
    850             855             860

Met Gly Ile Tyr Phe Ala Thr Pro Glu Trp Val Ala Leu Asn Gly His
865             870             875             880

Arg Gly Pro Ser Pro Gly Gln Leu Lys Tyr Trp Gln Asn Thr Arg Glu
            885             890             895

Ile Pro Asp Pro Asn Glu Asp Tyr Leu Asp Tyr Val His Ala Glu Lys
            900             905             910

Ser Arg Leu Ala Ser Glu Glu Gln Ile Leu Lys Ala Ala Thr Ser Ile
    915             920             925

Tyr Gly Ala Pro Gly Gln Ala Glu Pro Pro Gln Ala Phe Ile Asp Glu
    930             935             940

Val Ala Lys Val Tyr Glu Ile Asn His Gly Arg Gly Pro Asn Gln Glu
945             950             955             960

Gln Met Lys Asp Leu Leu Leu Thr Ala Met Glu Met Lys His Arg Asn
            965             970             975

Pro Arg Arg Ala Pro Pro Lys Pro Lys Pro Lys Pro Asn Ala Pro Thr
            980             985             990

Gln Arg Pro Pro Gly Arg Leu Gly Arg Trp Ile Arg Thr Val Ser Asp
    995             1000            1005

Glu Asp Leu Glu
    1010

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

Ser Trp Ser Ala Ser Gly Ser
1               5
```